US011224519B2

(12) United States Patent
Wentorf et al.

(10) Patent No.: US 11,224,519 B2
(45) Date of Patent: *Jan. 18, 2022

(54) ASYMMETRIC TIBIAL COMPONENTS FOR A KNEE PROSTHESIS

(71) Applicant: Zimmer, Inc., Warsaw, IN (US)

(72) Inventors: Mary S. S. Wentorf, Warsaw, IN (US); Jeffrey E. Bischoff, Warsaw, IN (US); Raymond C. Parisi, Wakarusa, IN (US); Katherine M. Rettig, Cincinnati, OH (US)

(73) Assignee: Zimmer, Inc., Warsaw, IN (US)

( * ) Notice: Subject to any disclaimer, the term of this patent is extended or adjusted under 35 U.S.C. 154(b) by 38 days.

This patent is subject to a terminal disclaimer.

(21) Appl. No.: 16/596,194

(22) Filed: Oct. 8, 2019

(65) Prior Publication Data

US 2020/0030106 A1    Jan. 30, 2020

Related U.S. Application Data

(63) Continuation of application No. 15/827,654, filed on Nov. 30, 2017, now Pat. No. 10,470,889, which is a
(Continued)

(51) Int. Cl.
*A61F 2/38* (2006.01)
*A61F 2/30* (2006.01)

(52) U.S. Cl.
CPC ............ *A61F 2/389* (2013.01); *A61F 2/3868* (2013.01); *A61F 2/3886* (2013.01);
(Continued)

(58) Field of Classification Search
CPC ................. A61F 2/389; A61F 2002/30326
See application file for complete search history.

(56) References Cited

U.S. PATENT DOCUMENTS 3,774,244 A    11/1973   Walker
4,016,606 A    4/1977    Murray et al.
(Continued)

FOREIGN PATENT DOCUMENTS

AU    2011343440 B2    4/2014
AU    2011286306 B2    10/2014
(Continued)

OTHER PUBLICATIONS

"U.S. Appl. No. 13/087,610, Non Final Office Action dated Feb. 26, 2013", 7 pgs.
(Continued)

*Primary Examiner* — Javier G Blanco
(74) *Attorney, Agent, or Firm* — Schwegman Lundberg & Woessner, P.A.

(57) ABSTRACT

An orthopaedic tibial prosthesis includes a tibial baseplate with an asymmetric periphery which promotes proper positioning and orientation on a resected tibia, while also facilitating enhanced kinematics, soft-tissue interaction, and long-term fixation of the complete knee prosthesis. The asymmetric baseplate periphery is sized and shaped to substantially match portions of the periphery of a typical resected proximal tibial surface, such that proper location and orientation is evident by resting the baseplate on the tibia. The baseplate periphery provides strategically positioned relief and/or clearance between the baseplate periphery and bone periphery, such as in the posterior-medial portion to prevent deep-flexion component impingement, and in the anterior-lateral portion to avoid undue interaction between the anatomic iliotibial band and prosthesis components.

18 Claims, 12 Drawing Sheets

Related U.S. Application Data continuation of application No. 14/034,937, filed on Sep. 24, 2013, now Pat. No. 9,861,490, which is a continuation of application No. 13/189,336, filed on Jul. 22, 2011, now Pat. No. 8,613,775.

(60) Provisional application No. 61/381,800, filed on Sep. 10, 2010, provisional application No. 61/367,375, filed on Jul. 24, 2010.

(52) U.S. Cl.
CPC .............. *A61F 2002/30326* (2013.01); *A61F 2002/30387* (2013.01); *A61F 2002/30616* (2013.01); *A61F 2002/30883* (2013.01); *A61F 2220/0025* (2013.01)

(56) References Cited

U.S. PATENT DOCUMENTS

| | | |
|---|---|---|
| 4,257,129 A | 3/1981 | Volz |
| 4,340,978 A | 7/1982 | Buechel et al. |
| 4,501,266 A | 2/1985 | McDaniel |
| 4,568,348 A | 2/1986 | Johnson et al. |
| 4,711,639 A | 12/1987 | Grundei |
| 4,714,474 A | 12/1987 | Brooks, Jr. et al. |
| 4,759,767 A | 7/1988 | Lacey |
| 4,769,040 A | 9/1988 | Wevers |
| 4,770,661 A | 9/1988 | Oh |
| 4,795,468 A | 1/1989 | Hodorek et al. |
| 4,822,365 A | 4/1989 | Walker et al. |
| 4,936,853 A | 6/1990 | Fabian et al. |
| 4,944,756 A | 7/1990 | Kenna |
| 4,944,757 A | 7/1990 | Martinez et al. |
| 4,950,298 A | 8/1990 | Gustilo et al. |
| 4,959,071 A | 9/1990 | Brown et al. |
| 4,963,152 A | 10/1990 | Hofmann et al. |
| 5,007,933 A | 4/1991 | Sidebotham et al. |
| 5,047,057 A | 9/1991 | Lawes |
| 5,047,058 A | 9/1991 | Roberts et al. |
| 5,059,216 A | 10/1991 | Winters |
| 5,061,271 A | 10/1991 | Van Zile |
| 5,071,438 A | 12/1991 | Jones et al. |
| 5,108,442 A | 4/1992 | Smith |
| 5,116,375 A | 5/1992 | Hofmann |
| 5,133,758 A | 7/1992 | Hollister |
| 5,137,536 A | 8/1992 | Koshino |
| 5,147,405 A | 9/1992 | Van Zile |
| 5,171,283 A | 12/1992 | Pappas et al. |
| 5,192,328 A | 3/1993 | Winters |
| 5,194,066 A | 3/1993 | Van Zile |
| 5,197,488 A | 3/1993 | Kovacevic |
| 5,219,362 A | 6/1993 | Tuke et al. |
| 5,226,915 A | 7/1993 | Bertin |
| 5,236,461 A | 8/1993 | Forte |
| 5,246,459 A | 9/1993 | Elias |
| 5,271,737 A | 12/1993 | Baldwin et al. |
| 5,275,603 A | 1/1994 | Ferrante et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,344,461 A | 9/1994 | Phlipot |
| 5,360,016 A | 11/1994 | Kovacevic |
| 5,364,402 A | 11/1994 | Mumme et al. |
| 5,370,699 A | 12/1994 | Hood et al. |
| 5,387,239 A | 2/1995 | Bianco et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,413,605 A | 5/1995 | Ashby et al. |
| 5,425,775 A | 6/1995 | Kovacevic et al. |
| 5,445,642 A | 8/1995 | McNulty et al. |
| 5,458,637 A | 10/1995 | Hayes |
| 5,470,354 A | 11/1995 | Hershberger et al. |
| 5,489,311 A | 2/1996 | Cipolletti |
| 5,507,820 A | 4/1996 | Pappas |
| 5,549,688 A | 8/1996 | Ries et al. |
| 5,556,433 A | 9/1996 | Gabriel et al. |
| 5,571,194 A | 11/1996 | Gabriel |
| 5,609,639 A | 3/1997 | Walker |
| 5,609,641 A | 3/1997 | Johnson et al. |
| 5,609,643 A | 3/1997 | Colleran et al. |
| 5,609,645 A | 3/1997 | Vinciuerra |
| 5,613,970 A | 3/1997 | Houston et al. |
| 5,656,785 A | 8/1997 | Trainor et al. |
| 5,658,341 A | 8/1997 | Delfosse |
| 5,658,342 A | 8/1997 | Draganich et al. |
| 5,658,344 A | 8/1997 | Hurlburt |
| 5,683,470 A | 11/1997 | Johnson et al. |
| 5,702,463 A | 12/1997 | Pothier et al. |
| 5,702,464 A | 12/1997 | Lackey et al. |
| 5,733,292 A | 3/1998 | Gustilo et al. |
| 5,755,801 A | 5/1998 | Walker et al. |
| 5,755,802 A | 5/1998 | Gerber |
| 5,776,200 A | 7/1998 | Johnson et al. |
| 5,782,925 A | 7/1998 | Collazo et al. |
| 5,824,100 A | 10/1998 | Kester et al. |
| 5,824,102 A | 10/1998 | Buscayret |
| 5,824,103 A | 10/1998 | Williams et al. |
| 5,871,539 A | 2/1999 | Pappas |
| 5,871,541 A | 2/1999 | Gerber |
| 5,871,543 A | 2/1999 | Hofmann |
| 5,871,545 A | 2/1999 | Goodfellow et al. |
| 5,879,394 A | 3/1999 | Ashby et al. |
| 5,906,643 A | 5/1999 | Walker |
| 5,911,723 A | 6/1999 | Ashby et al. |
| 5,928,286 A | 7/1999 | Ashby et al. |
| 5,964,808 A | 10/1999 | Blaha et al. |
| 5,968,099 A | 10/1999 | Badorf et al. |
| 5,976,147 A | 11/1999 | LaSalle et al. |
| 6,004,351 A | 12/1999 | Tomita et al. |
| 6,004,352 A | 12/1999 | Buni |
| 6,010,534 A | 1/2000 | O'neil et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,080,195 A | 6/2000 | Colleran et al. |
| 6,090,144 A | 7/2000 | Letot et al. |
| 6,102,954 A | 8/2000 | Albrektsson et al. |
| 6,102,955 A | 8/2000 | Mendes et al. |
| 6,123,729 A | 9/2000 | Insall et al. |
| 6,126,692 A | 10/2000 | Robie et al. |
| 6,143,034 A | 11/2000 | Burrows |
| 6,197,064 B1 | 3/2001 | Haines et al. |
| 6,203,576 B1 | 3/2001 | Afriat et al. |
| 6,206,927 B1 | 3/2001 | Fell et al. |
| 6,210,443 B1 | 4/2001 | Marceaux et al. |
| 6,217,618 B1 | 4/2001 | Hileman |
| RE37,277 E | 7/2001 | Baldwin et al. |
| 6,258,127 B1 | 7/2001 | Schmotzer |
| 6,306,172 B1 | 10/2001 | O'Neil et al. |
| 6,325,828 B1 | 12/2001 | Dennis et al. |
| 6,379,388 B1 | 4/2002 | Ensign et al. |
| 6,406,497 B2 | 6/2002 | Takei et al. |
| 6,413,279 B1 | 7/2002 | Metzger et al. |
| 6,428,577 B1 | 8/2002 | Evans |
| 6,436,145 B1 | 8/2002 | Miller |
| 6,491,726 B2 | 12/2002 | Pappas |
| 6,506,215 B1 | 1/2003 | Letot et al. |
| 6,506,216 B1 | 1/2003 | McCue et al. |
| 6,558,426 B1 | 5/2003 | Masini |
| 6,607,559 B2 | 8/2003 | Ralph et al. |
| 6,623,526 B1 | 9/2003 | Lloyd |
| 6,632,225 B2 | 10/2003 | Sanford et al. |
| 6,660,039 B1 | 12/2003 | Evans et al. |
| 6,702,821 B2 | 3/2004 | Bonutti |
| 6,709,461 B2 | 3/2004 | O'neil et al. |
| 6,743,258 B1 | 6/2004 | Keller |

(56) References Cited

U.S. PATENT DOCUMENTS

| | | |
|---|---|---|
| 6,755,864 B1 | 6/2004 | Brack et al. |
| 6,770,078 B2 | 8/2004 | Bonutti |
| 6,869,448 B2 | 3/2005 | Tuke |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,974,481 B1 | 12/2005 | Carson |
| 6,986,791 B1 | 1/2006 | Metzger |
| 7,025,788 B2 | 4/2006 | Metzger et al. |
| 7,060,074 B2 | 6/2006 | Rosa et al. |
| 7,081,137 B1 | 7/2006 | Servidio |
| 7,083,652 B2 | 8/2006 | McCUe et al. |
| 7,153,326 B1 | 12/2006 | Metzger |
| 7,160,330 B2 | 1/2007 | Axelson, Jr. et al. |
| 7,189,262 B2 | 3/2007 | Hayes, Jr. et al. |
| 7,261,740 B2 | 8/2007 | Tuttle |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,141,437 B2 | 3/2012 | Amirouche et al. |
| 8,163,028 B2 | 4/2012 | Metzger et al. |
| 8,187,280 B2 | 5/2012 | May et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,268,006 B2 | 9/2012 | Meyers et al. |
| 8,317,870 B2 | 11/2012 | Wagner et al. |
| 8,328,873 B2 | 12/2012 | Metzger et al. |
| 8,366,782 B2 | 2/2013 | Wright |
| 8,491,589 B2 | 7/2013 | Fisher et al. |
| 8,506,571 B2 | 8/2013 | Chana et al. |
| RE44,476 E | 9/2013 | Meyers et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 | 12/2013 | Claypool et al. |
| 8,613,775 B2 | 12/2013 | Wentorf et al. |
| 8,617,250 B2 | 12/2013 | Metzger |
| 8,628,580 B2 | 1/2014 | Sanford et al. |
| 8,690,954 B2 | 4/2014 | Parisi et al. |
| 8,740,984 B2 | 6/2014 | Hartdegen et al. |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,795,282 B2 | 8/2014 | Earl et al. |
| 8,808,387 B2 | 8/2014 | Hawkins et al. |
| 8,858,643 B2 | 10/2014 | Parisi |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 8,979,936 B2 | 3/2015 | White et al. |
| 8,998,997 B2 | 4/2015 | Ries et al. |
| 9,011,459 B2 | 4/2015 | Claypool et al. |
| 9,072,607 B2 | 7/2015 | Parisi et al. |
| 9,131,945 B2 | 9/2015 | Aram et al. |
| 9,149,206 B2 | 10/2015 | Claypool et al. |
| 9,173,744 B2 | 11/2015 | Donno et al. |
| 9,186,255 B2 | 11/2015 | Parisi |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,095 B2 | 4/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,707,089 B2 | 7/2017 | Grey et al. |
| 9,763,794 B2 | 9/2017 | Sanford et al. |
| 9,763,795 B2 | 9/2017 | Parisi et al. |
| 9,763,796 B2 | 9/2017 | Wentorf et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 9,925,050 B2 | 3/2018 | Parisi et al. |
| 9,925,052 B2 | 3/2018 | Dai et al. |
| 10,010,330 B2 | 7/2018 | Claypool et al. |
| 10,092,407 B2 | 10/2018 | Faccioli et al. |
| 10,188,530 B2 | 1/2019 | Claypool et al. |
| 10,195,041 B2 | 2/2019 | Wentorf et al. |
| 10,265,181 B2 | 4/2019 | Wentorf et al. |
| 10,278,827 B2 | 5/2019 | Drury |
| 10,413,415 B2 | 9/2019 | Parisi et al. |
| 10,470,889 B2 | 11/2019 | Wentorf et al. |
| 10,500,054 B2 | 12/2019 | Croll |
| 10,543,099 B2 | 1/2020 | Sanford et al. |
| 10,575,956 B2 | 3/2020 | Dai et al. |
| 10,675,153 B2 | 6/2020 | Byrd et al. |
| 10,835,380 B2 | 11/2020 | Drury et al. |
| 2001/0047210 A1 | 11/2001 | Wolf |
| 2002/0058997 A1 | 5/2002 | O'connor et al. |
| 2002/0072802 A1 | 6/2002 | O'Neil et al. |
| 2002/0120340 A1 | 8/2002 | Metzger et al. |
| 2002/0161448 A1 | 10/2002 | Hayes, Jr. et al. |
| 2003/0055509 A1 | 3/2003 | Mccue et al. |
| 2004/0019382 A1 | 1/2004 | Amirouche et al. |
| 2004/0019383 A1 | 1/2004 | Beguec |
| 2004/0034432 A1 | 2/2004 | Hughes et al. |
| 2004/0059340 A1 | 3/2004 | Serra et al. |
| 2004/0064191 A1 | 4/2004 | Wasielewski |
| 2004/0122441 A1 | 6/2004 | Muratsu |
| 2004/0153066 A1 | 8/2004 | Coon et al. |
| 2004/0162620 A1 | 8/2004 | Wyss |
| 2004/0167537 A1 | 8/2004 | Errico et al. |
| 2004/0186582 A1 | 9/2004 | Yasuda et al. |
| 2004/0204765 A1 | 10/2004 | Fenning et al. |
| 2004/0225368 A1 | 11/2004 | Plumet et al. |
| 2004/0236429 A1 | 11/2004 | Ensign et al. |
| 2004/0243244 A1 | 12/2004 | Otto et al. |
| 2004/0267371 A1 | 12/2004 | Hayes, Jr. et al. |
| 2005/0055102 A1 | 3/2005 | Tornier et al. |
| 2005/0096747 A1 | 5/2005 | Tuttle et al. |
| 2005/0143831 A1 | 6/2005 | Justin et al. |
| 2005/0143832 A1 | 6/2005 | Carson |

(56) References Cited

U.S. PATENT DOCUMENTS

| | | |
|---|---|---|
| 2005/0177170 A1 | 8/2005 | Fisher et al. |
| 2005/0019771 A1 | 9/2005 | Naegerl |
| 2005/0209701 A1 | 9/2005 | Suguro et al. |
| 2005/0209702 A1 | 9/2005 | Todd et al. |
| 2005/0246030 A1 | 11/2005 | Yao |
| 2005/0267485 A1 | 12/2005 | Cordes et al. |
| 2005/0267584 A1 | 12/2005 | Burdulis, Jr. et al. |
| 2005/0278035 A1 | 12/2005 | Wyss et al. |
| 2006/0004460 A1 | 1/2006 | Engh et al. |
| 2006/0020343 A1 | 1/2006 | Ek |
| 2006/0030945 A1 | 2/2006 | Wright |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0142869 A1 | 6/2006 | Gross |
| 2006/0161259 A1 | 7/2006 | Cheng et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor |
| 2006/0195195 A1 | 8/2006 | Burstein et al. |
| 2006/0111726 A1 | 10/2006 | Felt et al. |
| 2006/0224244 A1 | 10/2006 | Thomas et al. |
| 2006/0265080 A1 | 11/2006 | Mcminn |
| 2007/0010890 A1 | 1/2007 | Collazo |
| 2007/0123992 A1 | 5/2007 | Sanford |
| 2007/0129808 A1 | 6/2007 | Justin et al. |
| 2007/0135924 A1 | 6/2007 | Verhoogen |
| 2007/0135926 A1 | 6/2007 | Walker |
| 2007/0185581 A1 | 8/2007 | Akizuki et al. |
| 2007/0198022 A1 | 8/2007 | Lang et al. |
| 2007/0233269 A1 | 10/2007 | Steines et al. |
| 2007/0234819 A1 | 10/2007 | Amirouche et al. |
| 2007/0239165 A1 | 10/2007 | Amirouche |
| 2008/0021566 A1 | 1/2008 | Peters et al. |
| 2008/0051908 A1 | 2/2008 | Angibaud et al. |
| 2008/0058947 A1 | 3/2008 | Earl et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0103603 A1 | 5/2008 | Hlntermann |
| 2008/0114462 A1 | 5/2008 | Guidera et al. |
| 2008/0119938 A1 | 5/2008 | Oh |
| 2008/0119940 A1 | 5/2008 | Otto et al. |
| 2008/0140212 A1 | 6/2008 | Metzger et al. |
| 2008/0161918 A1 | 7/2008 | Fankhauser et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0262624 A1 | 10/2008 | White et al. |
| 2008/0281426 A1 | 11/2008 | Fitz et al. |
| 2008/0288080 A1 | 11/2008 | Sancheti |
| 2008/0300689 A1 | 12/2008 | Mc Kinnon et al. |
| 2008/0300690 A1 | 12/2008 | Burstein et al. |
| 2009/0005708 A1 | 1/2009 | Johanson et al. |
| 2009/0036992 A1 | 2/2009 | Tsakonas |
| 2009/0043395 A1 | 2/2009 | Hotokebuchi et al. |
| 2009/0062806 A1 | 3/2009 | Scott et al. |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204221 A1 | 8/2009 | Walker |
| 2009/0204222 A1 | 8/2009 | Burstein et al. |
| 2009/0210066 A1 | 8/2009 | Jasty |
| 2009/0222103 A1 | 9/2009 | Fitz et al. |
| 2009/0259314 A1 | 10/2009 | Linder-ganz et al. |
| 2009/0264894 A1 | 10/2009 | Wasielewski |
| 2009/0265011 A1 | 10/2009 | Mandell |
| 2009/0265013 A1 | 10/2009 | Mandell |
| 2009/0028731 A1 | 11/2009 | Fisher et al. |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0010494 A1 | 1/2010 | Quirno |
| 2010/0016976 A1 | 1/2010 | Siebel |
| 2010/0016977 A1 | 1/2010 | Masini |
| 2010/0016978 A1 | 1/2010 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0063594 A1 | 3/2010 | Hazebrouck et al. |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0100189 A1 | 4/2010 | Metzger |
| 2010/0100191 A1 | 4/2010 | May et al. |
| 2010/0125339 A1 | 5/2010 | Earl et al. |
| 2010/0152858 A1 | 6/2010 | Lu et al. |
| 2010/0191298 A1 | 7/2010 | Earl et al. |
| 2010/0191341 A1 | 7/2010 | Byrd |
| 2010/0198275 A1 | 8/2010 | Chana et al. |
| 2010/0222890 A1 | 9/2010 | Barnett et al. |
| 2010/0249660 A1 | 9/2010 | Sherman et al. |
| 2010/0249789 A1 | 9/2010 | Rock et al. |
| 2010/0262253 A1 | 10/2010 | Cipolletti et al. |
| 2010/0286788 A1 | 11/2010 | Komistek |
| 2010/0292804 A1 | 11/2010 | Samuelson |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0040387 A1 | 2/2011 | Ries et al. |
| 2011/0082558 A1 | 4/2011 | Kim et al. |
| 2011/0082559 A1 | 4/2011 | Hartdegen et al. |
| 2011/0087332 A1 | 4/2011 | Bojarski et al. |
| 2011/0098824 A1 | 4/2011 | Jukes et al. |
| 2011/0100011 A1 | 5/2011 | Staffend |
| 2011/0125278 A1 | 5/2011 | Bercovy et al. |
| 2011/0144760 A1 | 6/2011 | Wong et al. |
| 2011/0153026 A1 | 6/2011 | Heggendorn et al. |
| 2011/0190898 A1 | 8/2011 | Lenz et al. |
| 2011/0202139 A1 | 8/2011 | Metzger et al. |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0095563 A1 | 4/2012 | Sanford et al. |
| 2012/0101585 A1 | 4/2012 | Parisi et al. |
| 2012/0158152 A1 | 6/2012 | Claypool et al. |
| 2012/0179069 A1 | 7/2012 | Amirouche |
| 2012/0185054 A1 | 7/2012 | Maloney et al. |
| 2012/0185055 A1 | 7/2012 | Maloney et al. |
| 2012/0232429 A1 | 9/2012 | Fischer et al. |
| 2012/0290088 A1 | 11/2012 | Amirouche et al. |
| 2012/0296437 A1 | 11/2012 | Wyss et al. |
| 2012/0310246 A1 | 12/2012 | Belcher et al. |
| 2012/0310361 A1 | 12/2012 | Zubok et al. |
| 2012/0323335 A1 | 12/2012 | Parisi et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi |
| 2013/0131820 A1 | 5/2013 | Wentorf et al. |
| 2013/0017301 A1 | 7/2013 | Irwin |
| 2013/0226305 A1 | 8/2013 | Donno et al. |
| 2013/0253378 A1 | 9/2013 | Claypool et al. |
| 2013/0261504 A1 | 10/2013 | Claypool et al. |

(56) References Cited

U.S. PATENT DOCUMENTS

| | | |
|---|---|---|
| 2013/0261757 A1 | 10/2013 | Claypool et al. |
| 2013/0261758 A1 | 10/2013 | Claypool et al. |
| 2013/0345820 A1 | 12/2013 | Maloney et al. |
| 2014/0025175 A1 | 1/2014 | Wentorf et al. |
| 2014/0025176 A1 | 1/2014 | Wentorf |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0025644 A1 | 1/2015 | Heggendorn et al. |
| 2015/0066150 A1 | 3/2015 | Dai et al. |
| 2015/0088140 A1 | 3/2015 | Toler et al. |
| 2015/0190243 A1 | 7/2015 | Claypool et al. |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0030053 A1 | 2/2016 | Yager et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2017/0231773 A1 | 8/2017 | Lu |
| 2017/0266011 A1 | 9/2017 | Wentorf et al. |
| 2017/0281354 A1 | 10/2017 | Soffiatti et al. |
| 2018/0000601 A1 | 1/2018 | Sanford et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0161166 A1 | 6/2018 | Dai et al. |
| 2018/0256346 A1 | 9/2018 | Byrd et al. |
| 2018/0325684 A1 | 11/2018 | Croll |
| 2019/0142594 A1 | 5/2019 | Yager |
| 2019/0209333 A1 | 7/2019 | Drury et al. |
| 2019/0328535 A1 | 10/2019 | Drury et al. |
| 2019/0350718 A1 | 11/2019 | Parisi et al. |
| 2020/0069433 A1 | 3/2020 | Croll |
| 2020/0113702 A1 | 4/2020 | Sanford et al. |
| 2020/0146830 A1 | 5/2020 | Dai et al. |
| 2020/0237518 A1 | 7/2020 | Byrd et al. |
| 2021/0022875 A1 | 1/2021 | Drury et al. |

FOREIGN PATENT DOCUMENTS

| | | | |
|---|---|---|---|
| CA | 2190029 A1 | 11/1995 | |
| CA | 2856070 C | 7/2016 | |
| CH | 687584 A5 | 1/1997 | |
| CN | 1087506 A | 6/1994 | |
| CN | 1174498 A | 2/1998 | |
| CN | 1179709 A | 4/1998 | |
| CN | 1440262 A | 9/2003 | |
| CN | 1549695 A | 11/2004 | |
| CN | 2768715 Y | 4/2006 | |
| CN | 1780594 A | 5/2006 | |
| CN | 1874738 A | 12/2006 | |
| CN | 101214175 A | 7/2008 | |
| CN | 101222886 A | 7/2008 | |
| CN | 101288597 A | 10/2008 | |
| CN | 101347359 A | 1/2009 | |
| CN | 201175391 Y | 1/2009 | |
| CN | 101361684 A | 2/2009 | |
| CN | 101401750 A | 4/2009 | |
| CN | 101426453 A | 5/2009 | |
| CN | 101522136 A | 9/2009 | |
| CN | 101646392 A | 2/2010 | |
| CN | 101658446 A | 3/2010 | |
| CN | 101683289 A | 3/2010 | |
| CN | 101711701 A | 5/2010 | |
| CN | 101795643 A | 8/2010 | |
| CN | 101835441 A | 9/2010 | |
| CN | 102018584 A | 4/2011 | |
| CN | 102048594 A | 5/2011 | |
| CN | 102058446 A | 5/2011 | |
| CN | 102058448 A | 5/2011 | |
| CN | 102917670 A | 2/2013 | |
| CN | 103118634 A | 5/2013 | |
| CN | 103118635 A | 5/2013 | |
| CN | 103118636 A | 5/2013 | |
| CN | 103370025 A | 10/2013 | |
| CN | 103379880 A | 10/2013 | |
| CN | 103732186 A | 4/2014 | |
| CN | 104039273 A | 9/2014 | |
| CN | 104066402 A | 9/2014 | |
| CN | 104093380 A | 10/2014 | |
| CN | 104135969 A | 11/2014 | |
| CN | 104203160 A | 12/2014 | |
| CN | 104321263 A | 1/2015 | |
| CN | 104379094 A | 2/2015 | |
| CN | 104736105 A | 6/2015 | |
| CN | 105055052 A | 11/2015 | |
| CN | 105167889 A | 12/2015 | |
| CN | 103118634 B | 8/2016 | |
| CN | 103118636 B | 8/2016 | |
| CN | 104093380 B | 8/2016 | |
| CN | 103370025 B | 11/2016 | |
| CN | 106073949 A | 11/2016 | |
| CN | 106214292 A | 12/2016 | |
| CN | 108135701 A | 6/2018 | |
| CN | 106073949 B | 12/2018 | |
| CN | 109310504 A | 2/2019 | |
| CN | 110022798 A | 7/2019 | |
| CN | 110402123 A | 11/2019 | |
| CN | 110636818 A | 12/2019 | |
| EP | 0021421 A1 | 1/1981 | |
| EP | 0327495 A2 | 8/1989 | |
| EP | 340919 A1 | 11/1989 | |
| EP | 0340919 A1 | 11/1989 | |
| EP | 0372811 A1 | 6/1990 | |
| EP | 0306744 B1 | 4/1992 | |
| EP | 0495340 A1 | 7/1992 | |
| EP | 0636353 A1 | 2/1995 | |
| EP | 0672397 A1 | 9/1995 | |
| EP | 0552950 B1 | 9/1996 | |
| EP | 0536457 B1 | 1/1997 | |
| EP | 0642328 B1 | 12/1998 | |
| EP | 0592750 B1 | 1/1999 | |
| EP | 0903125 A1 | 3/1999 | |
| EP | 0956836 A1 | 11/1999 | |
| EP | 0956836 B1 | 11/1999 | |
| EP | 1025818 A2 | 8/2000 | |
| EP | 1097679 A1 | 5/2001 | |
| EP | 0709074 B1 | 12/2002 | |
| EP | 1327424 A1 | 7/2003 | |
| EP | 1378216 A2 | 1/2004 | |
| EP | 1477143 A1 | 11/2004 | |
| EP | 1568336 A1 | 8/2005 | |
| EP | 1719478 A2 | 11/2006 | |
| EP | 1722721 A1 | 11/2006 | |
| EP | 1354571 B1 | 6/2007 | |
| EP | 1396240 B1 | 4/2008 | |
| EP | 1604623 B1 | 6/2008 | |
| EP | 1996122 A1 | 12/2008 | |
| EP | 0927009 B1 | 1/2009 | |
| EP | 2011455 A1 | 1/2009 | |
| EP | 1696835 B1 | 2/2009 | |
| EP | 1132063 A2 | 9/2009 | |
| EP | 1591082 B1 | 9/2009 | |
| EP | 2140838 A2 | 1/2010 | |
| EP | 2140839 A1 | 1/2010 | |
| EP | 2143403 A1 | 1/2010 | |
| EP | 2237177 A1 | 10/2010 | |

(56) References Cited

FOREIGN PATENT DOCUMENTS

| | | |
|---|---|---|
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| EP | 2830543 A1 | 2/2015 |
| EP | 2830544 A1 | 2/2015 |
| EP | 2830544 B1 | 9/2016 |
| EP | 2918235 B1 | 1/2017 |
| EP | 3143964 A2 | 3/2017 |
| EP | 2595574 B1 | 5/2017 |
| EP | 3111894 B1 | 12/2018 |
| FR | 2728782 A1 | 7/1996 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2824260 A1 | 11/2002 |
| FR | 2852819 A1 | 10/2004 |
| FR | 2926719 A1 | 7/2009 |
| GB | 225347 A | 12/1924 |
| GB | 2253147 A | 9/1992 |
| GB | 2345446 A | 7/2000 |
| IN | 7145DELNP2014 A | 4/2015 |
| JP | 61247449 A | 11/1986 |
| JP | 62270153 A | 11/1987 |
| JP | 06203576 A | 7/1994 |
| JP | 09289998 A | 11/1997 |
| JP | 09511668 A | 11/1997 |
| JP | 2000000255 A | 1/2000 |
| JP | 2000245758 A | 9/2000 |
| JP | 2003516183 A | 5/2003 |
| JP | 2004166802 A | 6/2004 |
| JP | 2004254811 A | 9/2004 |
| JP | 3734270 B2 | 1/2006 |
| JP | 2007054488 A | 3/2007 |
| JP | 2007509709 A | 4/2007 |
| JP | 2007222616 A | 9/2007 |
| JP | 2009082713 A | 4/2009 |
| JP | 2009245619 A | 10/2009 |
| JP | 2010022827 A | 2/2010 |
| JP | 2010188051 A | 9/2010 |
| JP | 2010240406 A | 10/2010 |
| JP | 2010259808 A | 11/2010 |
| JP | 2011092738 A | 5/2011 |
| JP | 2012500667 A | 1/2012 |
| JP | 2012531265 A | 12/2012 |
| JP | 2015512307 A | 4/2013 |
| JP | 2013535276 A | 9/2013 |
| JP | 2013536005 A | 9/2013 |
| JP | 2013536006 A | 9/2013 |
| JP | 2013536007 A | 9/2013 |
| JP | 2014505517 A | 3/2014 |
| JP | 2014508554 A | 4/2014 |
| JP | 2014522292 A | 9/2014 |
| JP | 2014239900 A | 12/2014 |
| JP | 2015502203 A | 1/2015 |
| JP | 2015504333 A | 2/2015 |
| JP | 2015504759 A | 2/2015 |
| JP | 2015513966 A | 5/2015 |
| JP | 2015231566 A | 12/2015 |
| JP | 2016028729 A | 3/2016 |
| JP | 5980341 B2 | 8/2016 |
| JP | 2016195841 A | 11/2016 |
| JP | 2017221732 A | 12/2017 |
| WO | WO-9305729 A2 | 4/1993 |
| WO | WO-9409725 A1 | 5/1994 |
| WO | WO-9514444 A1 | 6/1995 |
| WO | WO-9514446 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-200141680 A1 | 6/2001 |
| WO | WO-03099106 A2 | 12/2003 |
| WO | WO-2004058108 A1 | 7/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007108804 A1 | 9/2007 |
| WO | WO-2007109641 A2 | 9/2007 |
| WO | WO-2007119173 A2 | 10/2007 |
| WO | WO-2009029631 A1 | 3/2009 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010001010 A1 | 1/2010 |
| WO | WO-2010008803 A2 | 1/2010 |
| WO | WO-2010011590 A1 | 1/2010 |
| WO | WO-2010022272 A1 | 2/2010 |
| WO | WO-2010023062 A2 | 3/2010 |
| WO | WO-2010045537 A1 | 4/2010 |
| WO | WO-2010075365 A2 | 7/2010 |
| WO | WO-2011043955 A1 | 4/2011 |
| WO | WO-2011063123 A2 | 5/2011 |
| WO | WO-2011071979 A2 | 6/2011 |
| WO | WO-2011072235 A2 | 6/2011 |
| WO | WO-2011110865 A2 | 9/2011 |
| WO | WO-2012004580 A1 | 1/2012 |
| WO | WO-2012018563 A1 | 2/2012 |
| WO | WO-2012018564 A1 | 2/2012 |
| WO | WO-2012018565 A1 | 2/2012 |
| WO | WO-2012018566 A1 | 2/2012 |
| WO | WO-2012018567 A1 | 2/2012 |
| WO | WO-2012020460 A1 | 2/2012 |
| WO | WO-2012082628 A1 | 6/2012 |
| WO | WO-2012083280 A1 | 6/2012 |
| WO | WO-2012112698 A2 | 8/2012 |
| WO | WO-2012173706 A1 | 12/2012 |
| WO | WO-2013003433 A1 | 1/2013 |
| WO | WO-2013013094 A1 | 1/2013 |
| WO | WO-2013074145 A1 | 5/2013 |
| WO | WO-2013074142 A1 | 5/2013 |
| WO | WO-2013074143 A1 | 5/2013 |
| WO | WO-2013074144 A1 | 5/2013 |
| WO | WO-2013077919 A1 | 5/2013 |
| WO | WO-2013115849 A1 | 8/2013 |
| WO | WO-2013148954 A1 | 10/2013 |
| WO | WO-2013148960 A1 | 10/2013 |
| WO | WO-2017053196 A1 | 3/2017 |
| WO | WO-2018165442 A1 | 9/2018 |
| WO | WO-2018208612 A1 | 11/2018 |

OTHER PUBLICATIONS

"U.S. Appl. No. 13/087,610, Notice of Allowance dated Jun. 28, 2013", 6 pgs.

"U.S. Appl. No. 13/087,610, Notice of Allowance dated Oct. 8, 2013", 7 pgs.

"U.S. Appl. No. 13/087,610, Response filed May 24, 2013 to Non Final Office Action dated Feb. 26, 2013", 15 pgs.

"U.S. Appl. No. 13/189,324, Examiner Interview Summary dated Jan. 13, 2014", 4 pgs.

"U.S. Appl. No. 13/189,324, Final Office Action dated Jul. 16, 2013", 19 pgs.

"U.S. Appl. No. 13/189,324, Non Final Office Action dated Dec. 11, 2012", 19 pgs.

"U.S. Appl. No. 13/189,324, Notice of Allowance dated Feb. 20, 2014", 8 pgs.

"U.S. Appl. No. 13/189,324, PTO Response to 312 Amendment dated May 29, 2014", 2 pgs.

"U.S. Appl. No. 13/189,324, Response filed Jan. 15, 14 to Final Office Action dated Jul. 16, 2013", 23 pgs.

"U.S. Appl. No. 13/189,324, Response filed Jun. 10, 2013 to Non Final Office Action dated Dec. 11, 2012", 24 pgs.

(56) References Cited

OTHER PUBLICATIONS

"U.S. Appl. No. 13/189,328, Non Final Office Action dated Mar. 19, 2013", 10 pgs.

"U.S. Appl. No. 13/189,328, Notice of Allowance dated Oct. 8, 2013", 12 pgs.

"U.S. Appl. No. 13/189,328, PTO Response to 312 Amendment dated Dec. 13, 2013", 2 pgs.

"U.S. Appl. No. 13/189,328, Response filed Jan. 10, 2013 to Restriction Requirement dated Dec. 10, 2012", 9 pgs.

"U.S. Appl. No. 13/189,328, Response filed Jul. 18, 2013 to Non Final Office Action dated Mar. 19, 2013", 16 pgs.

"U.S. Appl. No. 13/189,328, Restriction Requirement dated Dec. 10, 2012", 6 pgs.

"U.S. Appl. No. 13/189,336, Notice of Allowance dated Sep. 13, 2013", 30 pgs.

"U.S. Appl. No. 13/189,336, PTO Response to 312 Amendment dated Nov. 25, 2013", 2 pgs.

"U.S. Appl. No. 13/189,336, Response filed Apr. 15, 2013 to Restriction Requirement dated Jan. 30, 2013", 21 pgs.

"U.S. Appl. No. 13/189,336, Response filed Jul. 17, 2013 to Restriction Requirement dated Jun. 17, 2013", 20 pgs.

"U.S. Appl. No. 13/189,336, Restriction Requirement dated Jan. 30, 2013", 5 pgs.

"U.S. Appl. No. 13/189,336, Restriction Requirement dated Jun. 17, 2013", 6 pgs.

"U.S. Appl. No. 13/189,338, Notice of Allowance dated Sep. 23, 2013", 23 pgs.

"U.S. Appl. No. 13/189,338, Response filed Apr. 15, 13 to Restriction Requirement dated Feb. 14, 2013", 18 pgs.

"U.S. Appl. No. 13/189,338, Response filed Jul. 17, 2013 to Restriction Requirement dated Jun. 17, 2013", 16 pgs.

"U.S. Appl. No. 13/189,338, Restriction Requirement dated Feb. 14, 2013", 5 pgs.

"U.S. Appl. No. 13/189,338, Restriction Requirement dated Jun. 17, 2013", 6 pgs.

"U.S. Appl. No. 13/189,339, Notice of Allowance dated Sep. 20, 2013", 16 pgs.

"U.S. Appl. No. 13/189,339, Response filed Apr. 15, 13 to Restriction Requirement dated Mar. 6, 2013", 11 pgs.

"U.S. Appl. No. 13/189,339, Response filed Jul. 17, 2013 to Restriction Requirement dated Jun. 17, 2013", 10 pgs.

"U.S. Appl. No. 13/189,339, Restriction Requirement dated Mar. 6, 2013", 6 pgs.

"U.S. Appl. No. 13/189,339, Restriction Requirement dated Jun. 17, 2013", 7 pgs.

"U.S. Appl. No. 13/229,103, Applicant Interview Summary dated Sep. 23, 2013", 2 pgs.

"U.S. Appl. No. 13/229,103, Examiner Interview Summary dated Sep. 13, 2013", 3 pgs.

"U.S. Appl. No. 13/229,103, Non Final Office Action dated Apr. 1, 2013", 18 pgs.

"U.S. Appl. No. 13/229,103, Notice of Allowance dated Sep. 18, 2013", 9 pgs.

"U.S. Appl. No. 13/229,103, Response filed Jul. 1, 2013 to Non Final Office Action dated Apr. 1, 2013", 19 pgs.

"U.S. Appl. No. 13/229,103, Supplemental Notice of Allowability dated Oct. 18, 2013", 2 pgs.

"U.S. Appl. No. 13/459,037, Final Office Action dated Sep. 23, 2013", 9 pgs.

"U.S. Appl. No. 13/459,037, Non Final Office Action dated Apr. 23, 2013", 10 pgs.

"U.S. Appl. No. 13/459,037, Notice of Allowance dated Jun. 13, 2014", 9 pgs.

"U.S. Appl. No. 13/459,037, Preliminary Amendment filed Apr. 27, 2012", 3 pgs.

"U.S. Appl. No. 13/459,037, Response filed Mar. 21, 2014 to Final Office Action dated Sep. 23, 2013", 15 pgs.

"U.S. Appl. No. 13/459,037, Response filed Mar. 28, 2013 to Restriction Requirement dated Feb. 26, 2013", 9 pgs.

"U.S. Appl. No. 13/459,037, Response filed Jul. 23, 2013 to Non Final Office Action dated Apr. 23, 2013", 19 pgs.

"U.S. Appl. No. 13/459,037, Restriction Requirement dated Feb. 26, 2013", 6 pgs.

"U.S. Appl. No. 13/459,041, Non Final Office Action dated Jan. 15, 2014", 16 pgs.

"U.S. Appl. No. 13/459,041, Non Final Office Action dated Sep. 9, 2014", 14 pgs.

"U.S. Appl. No. 13/459,041, Notice of Allowance dated Apr. 2, 2015", 10 pgs.

"U.S. Appl. No. 13/459,041, Preliminary Amendment dated Apr. 27, 2012", 7 pgs.

"U.S. Appl. No. 13/459,041, PTO Response to Rule 312 Communication dated Jun. 9, 2015", 2 pgs.

"U.S. Appl. No. 13/459,041, Response filed May 15, 2014 to Non-Final Office Action dated Jan. 15, 2014", 24 pgs.

"U.S. Appl. No. 13/459,041, Response filed Sep. 23, 2013 to Restriction Requirement dated Jul. 25, 2013", 18 pgs.

"U.S. Appl. No. 13/459,041, Response filed Dec. 9, 2014 to Non-Final Office Action dated Sep. 9, 2014", 23 pgs.

"U.S. Appl. No. 13/459,041, Restriction Requirement dated Jul. 25, 2013", 9 pgs.

"U.S. Appl. No. 13/459,048, Non Final Office Action dated Jul. 11, 2013", 6 pgs.

"U.S. Appl. No. 13/459,048, Notice of Allowance dated Nov. 26, 2013", 10 pgs.

"U.S. Appl. No. 13/459,048, Preliminary Amendment filed Apr. 27, 2012", 7 pgs.

"U.S. Appl. No. 13/459,048, Response filed Nov. 11, 2013 to Non-Final Office Action dated Jul. 11, 2013", 16 pgs.

"U.S. Appl. No. 13/459,056, Examiner Interview Summary dated Dec. 26, 2013", 3 pgs.

"U.S. Appl. No. 13/459,056, Non Final Office Action dated Jul. 25, 2013", 11 pgs.

"U.S. Appl. No. 13/459,056, Notice of Allowance dated Feb. 20, 2014", 5 pgs.

"U.S. Appl. No. 13/459,056, Preliminary Amendment filed Apr. 27, 2012", 7 pgs.

"U.S. Appl. No. 13/459,056, PTO Response to Rule 312 Communication dated May 22, 2014", 2 pgs.

"U.S. Appl. No. 13/459,056, Response filed Jan. 24, 2014 to Non-Final office Action dated Jul. 25, 2013", 27 pgs.

"U.S. Appl. No. 13/459,056, Response filed Apr. 8, 2013 to Restriction Requirement dated Mar. 6, 2013", 15 pgs.

"U.S. Appl. No. 13/459,056, Restriction Requirement dated Mar. 6, 2013", 6 pgs.

"U.S. Appl. No. 13/593,339, Non Final Office Action dated Oct. 4, 2013", 7 pgs.

"U.S. Appl. No. 13/593,339, Notice of Allowance dated Feb. 14, 2014", 9 pgs.

"U.S. Appl. No. 13/593,339, Preliminary Amendment filed Aug. 23, 2012", 6 pgs.

"U.S. Appl. No. 13/593,339, Response filed Jan. 31, 2014 to Non-Final Office Action dated Oct. 4, 2013", 19 pgs.

"U.S. Appl. No. 13/593,339, Response filed Aug. 30, 2013 to Restriction Requirement dated Aug. 1, 2013", 14 pgs.

"U.S. Appl. No. 13/593,339, Restriction Requirement dated Aug. 1, 2013", 5 pgs.

"U.S. Appl. No. 13/593,339, Supplemental Notice of Allowability dated Mar. 31, 2014", 2 pgs.

"U.S. Appl. No. 13/594,543, Corrected Notice of Allowance dated Mar. 16, 2016", 2 pgs.

"U.S. Appl. No. 13/594,543, Examiner Interview Summary dated Jan. 22, 2016", 3 pgs.

"U.S. Appl. No. 13/594,543, Final Office Action dated Jul. 17, 2014", 12 pgs.

"U.S. Appl. No. 13/594,543, Final Office Action dated Nov. 20, 2015", 28 pgs.

"U.S. Appl. No. 13/594,543, Non Final Office Action dated Jun. 19, 2015", 30 pgs.

"U.S. Appl. No. 13/594,543, Non Final Office Action dated Dec. 26, 2013", 15 pgs.

(56) References Cited

OTHER PUBLICATIONS

"U.S. Appl. No. 13/594,543, Non-Final Office Action dated Jan. 9, 2015", 23 pgs.
"U.S. Appl. No. 13/594,543, Notice of Allowance dated Mar. 1, 2016", 9 pgs.
"U.S. Appl. No. 13/594,543, Preliminary Amendment filed Aug. 24, 2012", 4 pgs.
"U.S. Appl. No. 13/594,543, Response filed Feb. 8, 2016 to Final Office Action dated Nov. 20, 2015", 17 pgs.
"U.S. Appl. No. 13/594,543, Response filed Apr. 7, 2015 to Non-Final Office Action dated Jan. 9, 2015", 27 pgs.
"U.S. Appl. No. 13/594,543, Response filed May 7, 2014 to Non-Final office Action dated Dec. 26, 2013", 17 pgs.
"U.S. Appl. No. 13/594,543, Response filed Sep. 21, 2015 to Non-Final Office Action dated Jun. 19, 2015", 25 pgs.
"U.S. Appl. No. 13/594,543, Response filed Oct. 11, 2013 to Restriction Requirement dated Sep. 12, 2013", 8 pgs.
"U.S. Appl. No. 13/594,543, Response filed Dec. 17, 2014 to Final Office Action dated Jul. 17, 2014", 15 pgs.
"U.S. Appl. No. 13/594,543, Restriction Requirement dated Sep. 12, 2013", 5 pgs.
"U.S. Appl. No. 13/819,116, Advisory Action dated Jan. 5, 2016", 3 pgs.
"U.S. Appl. No. 13/819,116, Corrected Notice of Allowance dated Oct. 21, 2016", 2 pgs.
"U.S. Appl. No. 13/819,116, Examiner Interview Summary dated Apr. 18, 2016", 11 pgs.
"U.S. Appl. No. 13/819,116, Final Office Action dated Jul. 26, 2016", 6 pgs.
"U.S. Appl. No. 13/819,116, Final Office Action dated Oct. 21, 2015", 15 pgs.
"U.S. Appl. No. 13/819,116, Non Final Office Action dated Feb. 17, 2016", 15 pgs.
"U.S. Appl. No. 13/819,116, Non Final Office Action dated Jun. 2, 2015", 14 pgs.
"U.S. Appl. No. 13/819,116, Notice of Allowance dated Sep. 29, 2016", 5 pgs.
"U.S. Appl. No. 13/819,116, Preliminary Amendment filed Feb. 26, 2013", 8 pgs.
"U.S. Appl. No. 13/819,116, Response filed Mar. 27, 2015 to Restriction Requirement dated Feb. 12, 2015", 11 pgs.
"U.S. Appl. No. 13/819,116, Response filed Apr. 29, 2016 to Non Final Office Action dated Feb. 17, 2016", 17 pgs.
"U.S. Appl. No. 13/819,116, Response filed Jul. 16, 2015 to Non Final Office Action dated Jun. 2, 2015", 22 pgs.
"U.S. Appl. No. 13/819,116, Response filed Sep. 14, 2016 Final Office Action dated Jul. 26, 2016", 10 pgs.
"U.S. Appl. No. 13/819,116, Response filed Dec. 15, 2015 to Final Office Action dated Oct. 21, 2015", 16 pgs.
"U.S. Appl. No. 13/819,116, Restriction Requirement dated Feb. 12, 2015", 7 pgs.
"U.S. Appl. No. 13/836,586, Express Abandonment filed May 30, 2014", 1 pg.
"U.S. Appl. No. 13/836,665, Examiner Interview Summary dated Jul. 17, 2014", 4 pgs.
"U.S. Appl. No. 13/836,665, Final Office Action dated Jul. 25, 2014", 25 pgs.
"U.S. Appl. No. 13/836,665, Non Final Office Action dated Jan. 30, 2014", 21 pgs.
"U.S. Appl. No. 13/836,665, Notice of Allowance dated Jun. 9, 2015", 10 pgs.
"U.S. Appl. No. 13/836,665, Response filed Jan. 23, 2015 to Final Office Action dated Jul. 25, 2014", 25 pgs.
"U.S. Appl. No. 13/836,665, Response filed May 30, 2014 to Non-Final Office Action dated Jan. 30, 2014", 21 pgs.
"U.S. Appl. No. 13/837,294, Final Office Action dated Apr. 25, 2016", 7 pgs.
"U.S. Appl. No. 13/837,294, Final Office Action dated Jun. 2, 2016", 7 pgs.
"U.S. Appl. No. 13/837,294, Non Final Office Action dated Dec. 10, 2015", 8 pgs.
"U.S. Appl. No. 13/837,294, Notice of Allowance dated Aug. 25, 2016", 5 pgs.
"U.S. Appl. No. 13/837,294, Response filed Mar. 4, 2016 to Non Final Office Action dated Dec. 10, 2015", 16 pgs.
"U.S. Appl. No. 13/837,294, Response filed Aug. 3, 2016 to Final Office Action dated Jun. 2, 2016", 7 pgs.
"U.S. Appl. No. 13/837,294, Response filed Oct. 12, 2015 to Restriction Requirement dated Aug. 24, 2015", 9 pgs.
"U.S. Appl. No. 13/837,294, Restriction Requirement dated Aug. 24, 2015", 6 pgs.
"U.S. Appl. No. 13/837,774, Examiner Interview Summary dated Jul. 22, 2014", 4 pgs.
"U.S. Appl. No. 13/837,774, Final Office Action dated Mar. 17, 2016", 14 pgs.
"U.S. Appl. No. 13/837,774, Final Office Action dated Jul. 28, 2014", 17 pgs.
"U.S. Appl. No. 13/837,774, Non Final Office Action dated Feb. 10, 2014", 33 pgs.
"U.S. Appl. No. 13/837,774, Non Final Office Action dated Sep. 18, 2015", 16 pgs.
"U.S. Appl. No. 13/837,774, Response filed Jan. 28, 2015 to Final Office Action dated Jul. 28, 2014", 16 pgs.
"U.S. Appl. No. 13/837,774, Response filed Jun. 10, 2014 to Non-Final Office Action dated Feb. 20, 2014", 29 pgs.
"U.S. Appl. No. 13/837,774, Response filed Jul. 7, 2015 to Restriction Requirement dated May 20, 2015", 10 pgs.
"U.S. Appl. No. 13/837,774, Response filed Dec. 16, 2015 to Non Final Office Action dated Sep. 18, 2015", 17 pgs.
"U.S. Appl. No. 13/837,774, Restriction Requirement dated May 20, 2015", 6 pgs.
"U.S. Appl. No. 14/034,076, Appeal Brief Filed Apr. 18, 2016", 21 pgs.
"U.S. Appl. No. 14/034,076, Final Office Action dated Dec. 21, 2015", 11 pgs.
"U.S. Appl. No. 14/034,076, Non Final Office Action dated Jun. 24, 2015", 11 pgs.
"U.S. Appl. No. 14/034,076, Notice of Allowance dated Oct. 28, 2016", 7 pgs.
"U.S. Appl. No. 14/034,076, Response filed Nov. 16, 2015 to Non Final Office Action dated Jun. 24, 2015", 13 pgs.
"U.S. Appl. No. 14/034,937, Appeal Brief Filed Sep. 9, 2015", 41 pgs.
"U.S. Appl. No. 14/034,937, Appeal Decision mailed May 30, 2017", 34 pgs.
"U.S. Appl. No. 14/034,937, Final Office Action dated Jun. 5, 2015", 22 pgs.
"U.S. Appl. No. 14/034,937, Non Final Office Action dated Jan. 2, 2015", 21 pgs.
"U.S. Appl. No. 14/034,937, Notice of Allowance dated Aug. 30, 2017", 14 pgs.
"U.S. Appl. No. 14/034,937, Preliminary Amendment filed Sep. 24, 2013", 3 pgs.
"U.S. Appl. No. 14/034,937, PTO Response to Rule 312 Communication dated Oct. 10, 2017", 2 pgs.
"U.S. Appl. No. 14/034,937, Response filed Mar. 30, 2015 to Non-Final Office Action", 24 pgs.
"U.S. Appl. No. 14/034,937, Response filed Oct. 27, 2014 to Restriction Requirement dated Sep. 11, 2014", 12 pgs.
"U.S. Appl. No. 14/034,937, Restriction Requirement dated Sep. 11, 2014", 6 pgs.
"U.S. Appl. No. 14/034,937, Supplemental Preliminary Amendment filed Oct. 24, 2013", 11 pgs.
"U.S. Appl. No. 14/034,944, Non Final Office Action dated Mar. 3, 2015", 16 pgs.
"U.S. Appl. No. 14/034,944, Notice of Allowance dated Aug. 28, 2015", 7 pgs.
"U.S. Appl. No. 14/034,944, Preliminary Amendment filed Sep. 24, 2013", 3 pgs.
"U.S. Appl. No. 14/034,944, Response filed Jun. 23, 2015 to Non Final Office Action dated Mar. 3, 2015", 15 pgs.

(56) References Cited

OTHER PUBLICATIONS

"U.S. Appl. No. 14/034,944, Response filed Dec. 15, 2014 to Restriction Requirement dated Oct. 14, 2014", 12 pgs.
"U.S. Appl. No. 14/034,944, Restriction Requirement dated Oct. 14, 2014", 6 pgs.
"U.S. Appl. No. 14/034,944, Supplemental Preliminary Amendment filed Oct. 24, 2013", 11 pgs.
"U.S. Appl. No. 14/034,954, Advisory Action dated Aug. 25, 2015", 3 pgs.
"U.S. Appl. No. 14/034,954, Final Office Action dated Jun. 1, 2015", 26 pgs.
"U.S. Appl. No. 14/034,954, Non Final Office Action dated Dec. 19, 2014", 25 pgs.
"U.S. Appl. No. 14/034,954, Notice of Allowance dated Nov. 20, 2015", 11 pgs.
"U.S. Appl. No. 14/034,954, Preliminary Amendment filed Sep. 24, 2013", 3 pgs.
"U.S. Appl. No. 14/034,954, Response filed Mar. 17, 2015 to Non Final Office Action dated Dec. 19, 2014", 21 pgs.
"U.S. Appl. No. 14/034,954, Response filed Aug. 3, 2015 to Final Office Action dated Jun. 1, 2015", 19 pgs.
"U.S. Appl. No. 14/034,954, Response filed Aug. 31, 2015 to Advisory Action dated Aug. 25, 2015", 21 pgs.
"U.S. Appl. No. 14/034,954, Response filed Oct. 27, 2014 to Restriction Requirement dated Aug. 25, 2014", 11 pgs.
"U.S. Appl. No. 14/034,954, Restriction Requirement dated Aug. 25, 2014", 7 pgs.
"U.S. Appl. No. 14/034,954, Supplemental Preliminary Amendment filed Oct. 25, 2013", 8 pgs.
"U.S. Appl. No. 14/034,963, Final Office Action dated Apr. 13, 2015", 22 pgs.
"U.S. Appl. No. 14/034,963, Final Office Action dated Oct. 13, 2015", 11 pgs.
"U.S. Appl. No. 14/034,963, Non Final Office Action dated Jul. 1, 2015", 15 pgs.
"U.S. Appl. No. 14/034,963, Non Final Office Action dated Nov. 21, 2014", 19 pgs.
"U.S. Appl. No. 14/034,963, Notice of Allowance dated Dec. 18, 2015", 5 pgs.
"U.S. Appl. No. 14/034,963, Preliminary Amendment filed Sep. 24, 2013", 3 pgs.
"U.S. Appl. No. 14/034,963, Response filed Mar. 20, 2015 to Non-Final Office Action dated Nov. 21, 2014", 20 pgs.
"U.S. Appl. No. 14/034,963, Response filed Jun. 19, 2015 to Final Office Action dated Apr. 13, 2015", 17 pgs.
"U.S. Appl. No. 14/034,963, Response filed Sep. 30, 2015 to Non Final Office Action dated Jul. 1, 2015", 14 pgs.
"U.S. Appl. No. 14/034,963, Response filed Nov. 20, 2015 to Final Office Action dated Oct. 13, 2015", 12 pgs.
"U.S. Appl. No. 14/063,032, Non Final Office Action dated Jun. 20, 2014", 6 pgs.
"U.S. Appl. No. 14/063,032, Notice of Allowance dated Dec. 19, 2014", 6 pgs.
"U.S. Appl. No. 14/063,032, Preliminary Amendment filed Oct. 25,2013", 3 pgs.
"U.S. Appl. No. 14/063,032, Response filed Oct. 20, 2014 to Non-Final Office Action dated Jun. 20, 2014", 9 pgs.
"U.S. Appl. No. 14/063,593, Advisory Action dated Aug. 19, 2016", 3 pgs.
"U.S. Appl. No. 14/063,593, Final Office Action dated Jun. 9, 2016", 10 pgs.
"U.S. Appl. No. 14/063,593, Non Final Office Action dated Jan. 25, 2016", 9 pgs.
"U.S. Appl. No. 14/063,593, Non Final Office Action dated Nov. 30, 2016", 12 pgs.
"U.S. Appl. No. 14/063,593, Notice of Allowance dated May 2, 2017", 5 pgs.
"U.S. Appl. No. 14/063,593, Notice of Allowance dated May 25, 2017", 5 pgs.
"U.S. Appl. No. 14/063,593, Preliminary Amendment filed Oct. 25, 2013", 3 pgs.
"U.S. Appl. No. 14/063,593, Response filed Jan. 4, 2016 to Restriction Requirement dated Nov. 6, 2015", 6 pgs.
"U.S. Appl. No. 14/063,593, Response filed Feb. 24, 2017 to Non Final Office Action dated Nov. 30, 2016", 17 pgs.
"U.S. Appl. No. 14/063,593, Response filed Apr. 20, 2016 to Non Final Office Action dated Jan. 25, 2016", 17 pgs.
"U.S. Appl. No. 14/063,593, Response filed Aug. 11, 2016 to Final Office Action dated Jun. 9, 2016", 10 pgs.
"U.S. Appl. No. 14/063,593, Restriction Requirement dated Nov. 6, 2015", 6 pgs.
"U.S. Appl. No. 14/181,033, Non Final Office Action dated May 1, 2015", 5 pgs.
"U.S. Appl. No. 14/181,033, Notice of Allowance dated Jul. 17, 2015", 10 pgs.
"U.S. Appl. No. 14/181,033, Response filed Jun. 22, 2015 to Non-Final Office Action dated May 1, 2015", 11 pgs.
"U.S. Appl. No. 14/278,805, Notice of Allowance dated Dec. 1, 2015", 8 pgs.
"U.S. Appl. No. 14/278,805, Supplemental Notice of Allowability dated Jan. 21, 2016", 2 pgs.
"U.S. Appl. No. 14/284,028, Non Final Office Action dated Jul. 7, 2015", 17 pgs.
"U.S. Appl. No. 14/284,028, Notice of Allowance dated Nov. 6, 2015", 5 pgs.
"U.S. Appl. No. 14/284,028, Response filed Oct. 6, 2015 to Non Final Office Action dated Jul. 7, 2015", 15 pgs.
"U.S. Appl. No. 14/284,028, Supplemental Notice of Allowability dated Feb. 26, 2016", 5 pgs.
"U.S. Appl. No. 14/284,028, Supplemental Preliminary Amendment filed Jul. 8, 2014", 13 pgs.
"U.S. Appl. No. 14/284,144, Final Office Action dated Aug. 7, 2015", 13 pgs.
"U.S. Appl. No. 14/284,144, Non Final Office Action dated Mar. 25, 2015", 26 pgs.
"U.S. Appl. No. 14/284,144, Notice of Allowance dated Oct. 29, 2015", 8 pgs.
"U.S. Appl. No. 14/284,144, Preliminary Amendment filed May 21, 2014", 3 pgs.
"U.S. Appl. No. 14/284,144, Response filed Oct. 9, 2015 to Final Office Action dated Aug. 7, 2015", 13 pgs.
"U.S. Appl. No. 14/284,144, Response filed Jun. 23, 2015 to Non Final Office Action dated Mar. 25, 2015", 22 pgs.
"U.S. Appl. No. 14/284,144, Supplemental Preliminary Amendment filed Jul. 3, 2014", 10 pgs.
"U.S. Appl. No. 14/304,009, Notice of Allowance dated Nov. 16, 2016", 7 pgs.
"U.S. Appl. No. 14/304,009, Preliminary Amendment Filed Jul. 31, 2014", 7 pgs.
"U.S. Appl. No. 14/490,153, Final Office Action dated Apr. 15, 2015", 18 pgs.
"U.S. Appl. No. 14/490,153, Non Final Office Action dated Nov. 12, 2014", 9 pgs.
"U.S. Appl. No. 14/490,153, Notice of Allowance dated Aug. 14, 2015", 10 pgs.
"U.S. Appl. No. 14/490,153, Preliminary Amendment filed Sep. 18, 2014", 3 pgs.
"U.S. Appl. No. 14/490,153, Response filed Feb. 18, 2015 to Non-Final Office Action dated Nov. 12, 2014", 14 pgs.
"U.S. Appl. No. 14/490,153, Response filed Jul. 7, 2015 to Final Office Action dated Apr. 15, 2015", 14 pgs.
"U.S. Appl. No. 14/660,217, Corrected Notice of Allowance dated May 26, 2016", 3 pgs.
"U.S. Appl. No. 14/660,217, Non Final Office Action dated Dec. 17, 2015", 8 pgs.
"U.S. Appl. No. 14/660,217, Notice of Allowance dated Apr. 26, 2016", 5 pgs.
"U.S. Appl. No. 14/660,217, Preliminary Amendment filed Mar. 18, 2015", 9 pgs.
"U.S. Appl. No. 14/660,217, Response filed Mar. 23, 2016 to Non Final Office Action dated Dec. 17, 2015", 14 pgs.

(56) References Cited

OTHER PUBLICATIONS

"U.S. Appl. No. 14/740,690, Non Final Office Action dated Dec. 7, 2016", 19 pgs.
"U.S. Appl. No. 14/740,690, Notice of Allowability dated Aug. 29, 2017", 2 pgs.
"U.S. Appl. No. 14/740,690, Notice of Allowance dated Jun. 13, 2017", 9 pgs.
"U.S. Appl. No. 14/740,690, Response filed Mar. 3, 2017 to Non Final Office Action dated Dec. 7, 2016", 14 pgs.
"U.S. Appl. No. 14/791,952, Corrected Notice of Allowance dated Jul. 21, 2017", 2 pgs.
"U.S. Appl. No. 14/791,952, Final Office Action dated Mar. 31, 2017", 8 pgs.
"U.S. Appl. No. 14/791,952, Final Office Action dated Sep. 1, 2016", 17 pgs.
"U.S. Appl. No. 14/791,952, Non Final Office Action dated Apr. 21, 2016", 12 pgs.
"U.S. Appl. No. 14/791,952, Non Final Office Action dated Dec. 29, 2016", 12 pgs.
"U.S. Appl. No. 14/791,952, Notice of Allowance dated May 30, 2017", 7 pgs.
"U.S. Appl. No. 14/791,952, Preliminary Amendment filed Jul. 7, 2015", 7 pgs.
"U.S. Appl. No. 14/791,952, Response filed Mar. 20, 2017 to Non Final Office Action dated Dec. 29, 2016", 12 pgs.
"U.S. Appl. No. 14/791,952, Response filed May 17, 2017—to Final Office Action dated Mar. 31, 2017", 10 pgs.
"U.S. Appl. No. 14/791,952, Response filed Jul. 15, 2016 to Non Final Office Action dated Apr. 21, 2016", 18 pgs.
"U.S. Appl. No. 14/791,952, Response filed Nov. 21, 2016 to Final Office Action dated Sep. 1, 2016", 15 pgs.
"U.S. Appl. No. 14/833,385, Examiner Interview Summary dated Dec. 27, 2017", 3 pgs.
"U.S. Appl. No. 14/833,385, Final Office Action dated Nov. 13, 2017", 9 pgs.
"U.S. Appl. No. 14/833,385, Non Final Office Action dated Jun. 19, 2017", 10 pgs.
"U.S. Appl. No. 14/833,385, Preliminary Amendment filed Aug. 25, 2015", 6 pgs.
"U.S. Appl. No. 14/833,385, Response filed May 12, 2017 to Restriction Requirement dated Mar. 17, 2017", 8 pgs.
"U.S. Appl. No. 14/833,385, Response filed Sep. 18, 2017 to Non Final Office Action dated Jun. 19, 2017", 14 pgs.
"U.S. Appl. No. 14/833,385, Restriction Requirement dated Mar. 17, 2017", 6 pgs.
"U.S. Appl. No. 14/918,721, Final Office Action dated Oct. 20, 2016", 5 pgs.
"U.S. Appl. No. 14/918,721, Non Final Office Action dated Jun. 16, 2016", 6 pgs.
"U.S. Appl. No. 14/918,721, Notice of Allowance dated Feb. 1, 2017", 9 pgs.
"U.S. Appl. No. 14/918,721, Preliminary Amendment filed Oct. 23, 2015", 8 pgs.
"U.S. Appl. No. 14/918,721, PTO Response to Rule 312 Communication dated Mar. 17, 2017", 2 pgs.
"U.S. Appl. No. 14/918,721, Response filed Sep. 12, 2016 to Non Final Office Action dated Jun. 16, 2016", 12 pgs.
"U.S. Appl. No. 14/918,721, Response filed Dec. 13, 2016 to Final Office Action dated Oct. 20, 2016", 9 pgs.
"U.S. Appl. No. 14/926,281, Non Final Office Action dated Jun. 21, 2017", 17 pgs.
"U.S. Appl. No. 14/926,281, Notice of Allowance dated Nov. 16, 2017", 9 pgs.
"U.S. Appl. No. 14/926,281, Preliminary Amendment filed Oct. 30, 2015", 8 pgs.
"U.S. Appl. No. 14/926,281, Response filed Sep. 18, 2017 to Non Final Office Action dated Jun. 21, 2017", 11 pgs.
"U.S. Appl. No. 15/003,091, Preliminary Amendment filed Jan. 22, 2016", 12 pgs.
"U.S. Appl. No. 15/003,091, Non Final Office Action dated Jun. 20, 2017", 14 pgs.
"U.S. Appl. No. 15/003,091, Notice of Allowance dated Nov. 6, 2017", 8 pgs.
"U.S. Appl. No. 15/003,091, PTO Response to Rule 312 Communication dated Jan. 23, 2018", 2 pgs.
"U.S. Appl. No. 15/003,091, Response filed Sep. 20, 2017 to Non Final Office Action dated Jun. 20, 2017", 17 pgs.
"U.S. Appl. No. 15/045,799, Non Final Office Action dated Nov. 1, 2016", 8 pgs.
"U.S. Appl. No. 15/045,799, Notice of Allowance dated Mar. 10, 2017", 10 pgs.
"U.S. Appl. No. 15/045,799, Preliminary Amendment filed Feb. 2018, 16", 9 pgs.
"U.S. Appl. No. 15/045,799, PTO Response to Rule 312 Communication dated Apr. 18, 2017", 2 pgs.
"U.S. Appl. No. 15/045,799, Response filed Feb. 1, 2017 to Non Final Office Action dated Nov. 1, 2016", 15 pgs.
"U.S. Appl. No. 15/062,252, Preliminary Amendment filed Mar. 9, 2016", 8 pgs.
"U.S. Appl. No. 15/062,262, Non Final Office Action dated Jul. 22, 2016", 12 pgs.
"U.S. Appl. No. 15/062,262, Notice of Allowance dated Jan. 31, 2017", 5 pgs.
"U.S. Appl. No. 15/062,262, PTO Response to Rule 312 Communication dated Mar. 7, 2017", 2 pgs.
"U.S. Appl. No. 15/062,262, Response filed Oct. 24, 2016 to Non Final Office Action dated Jul. 22, 2016", 13 pgs.
"U.S. Appl. No. 15/177,734, Non Final Office Action dated Feb. 10, 2017", 21 pgs.
"U.S. Appl. No. 15/177,734, Notice of Allowance dated May 17, 2017", 7 pgs.
"U.S. Appl. No. 15/177,734, Preliminary Amendment filed Jun. 22, 2016", 8 pgs.
"U.S. Appl. No. 15/177,734, Response filed Apr. 19, 2017 to Non Final Office Action dated Feb. 10, 2017", 22 pgs.
"U.S. Appl. No. 15/211,812, Non Final Office Action dated Jan. 27, 2017", 5 pgs.
"U.S. Appl. No. 15/211,812, Notice of Allowance dated May 31, 2017", 5 pgs.
"U.S. Appl. No. 15/211,812, Preliminary Amendment filed Sep. 8, 2016", 8 pgs.
"U.S. Appl. No. 15/211,812, Response filed Apr. 19, 2017 to Non Final Office Action dated Jan. 27, 2017", 9 pgs.
"U.S. Appl. No. 15/267,793, Non Final Office Action dated Jun. 14, 2018", 12 pgs.
"U.S. Appl. No. 15/267,793, Notice of Allowability dated Jan. 17, 2019", 2 pgs.
"U.S. Appl. No. 15/267,793, Notice of Allowance dated Dec. 21, 2018", 5 pgs.
"U.S. Appl. No. 15/267,793, Response Filed Apr. 11, 2018 to Restriction Requirement dated Feb. 16, 2018", 8 pgs.
"U.S. Appl. No. 15/267,793, Response filed Aug. 22, 2018 Non Final Office Action dated Jun. 14, 2018", 16 pgs.
"U.S. Appl. No. 15/267,793, Restriction Requirement dated Feb. 16, 2018", 7 pgs.
"U.S. Appl. No. 15/424,328, Non Final Office Action dated Jun. 23, 2017", 5 pgs.
"U.S. Appl. No. 15/424,328, Notice of Allowance dated Oct. 16, 2017", 6 pgs.
"U.S. Appl. No. 15/424,328, Preliminary Amendment filed Feb. 28, 2017", 10 pgs.
"U.S. Appl. No. 15/424,328, Response filed Sep. 20, 2017 to Non Final Office Action dated Jun. 23, 2017", 9 pgs.
"U.S. Appl. No. 15/435,620, Final Office Action dated Dec. 15, 2017", 9 pgs.
"U.S. Appl. No. 15/435,620, Non Final Office Action dated Jul. 26, 2017", 10 pgs.
"U.S. Appl. No. 15/435,620, Notice of Allowance dated Mar. 13, 2018", 5 pgs.
"U.S. Appl. No. 15/435,620, Preliminary Amendment filed Mar. 20, 2017", 7 pgs.

(56) References Cited

OTHER PUBLICATIONS

"U.S. Appl. No. 15/435,620, Response filed Feb. 12, 2018 to Final Office Action dated Dec. 15, 2017", 9 pgs.
"U.S. Appl. No. 15/435,620, Response filed Oct. 25, 2017 to Non Final Office Action dated Jul. 26, 2017", 13 pgs.
"U.S. Appl. No. 15/616,561, Non Final Office Action mailed Aug. 9, 2018", 8 pgs.
"U.S. Appl. No. 15/616,561, Notice of Allowability dated Feb. 12, 2019", 2 pgs.
"U.S. Appl. No. 15/616,561, Notice of Allowance dated Dec. 10, 2018", 7 pgs.
"U.S. Appl. No. 15/616,561, Preliminary Amendment filed Jun. 8, 2017", 7 pgs.
"U.S. Appl. No. 15/616,561, Response filed Nov. 8, 2018 to Non Final Office Action dated Aug. 9, 2018", 11 pgs.
"U.S. Appl. No. 15/703,678, Non Final Office Action mailed Apr. 8, 2019", 11 pgs.
"U.S. Appl. No. 15/703,678, Notice of Allowance dated Sep. 17, 2019", 7 pgs.
"U.S. Appl. No. 15/703,678, Preliminary Amendment filed Sep. 28, 2017", 9 pgs.
"U.S. Appl. No. 15/703,678, Response Filed Jan. 3, 2019 to Restriction Requirement dated Nov. 5, 2018", 8 pgs.
"U.S. Appl. No. 15/703,678, Response filed Jul. 3, 2019 to Non-Final Office Action dated Apr. 8, 2019", 20 pgs.
"U.S. Appl. No. 15/703,678, Restriction Requirement dated Nov. 5, 2018", 6 pgs.
"U.S. Appl. No. 15/703,692, Corrected Notice of Allowability dated Jul. 8, 2019", 2 pgs.
"U.S. Appl. No. 15/703,692, Non Final Office Action dated Jan. 14, 2019", 11 pgs.
"U.S. Appl. No. 15/703,692, Notice of Allowance dated May 7, 2019", 5 pgs.
"U.S. Appl. No. 15/703,692, Preliminary Amendment filed Sep. 28, 2017", 9 pgs.
"U.S. Appl. No. 15/703,692, Response filed Apr. 4, 2019 to Non Final Office Action dated Jan. 14, 2019", 11 pgs.
"U.S. Appl. No. 15/703,698, Corrected Notice of Allowability dated Dec. 18, 2018", 2 pgs.
"U.S. Appl. No. 15/703,698, Non Final Office Action dated Apr. 6, 2018", 7 pgs.
"U.S. Appl. No. 15/703,698, Notice of Allowance dated Sep. 12, 2018", 5 pgs.
"U.S. Appl. No. 15/703,698, Preliminary Amendment filed Sep. 28, 2017", 8 pgs.
"U.S. Appl. No. 15/703,698, Response filed Jul. 6, 2018 to Non Final Office Action dated Apr. 6, 2018", 10 pgs.
"U.S. Appl. No. 15/703,713, Non Final Office Action dated Mar. 27, 2018", 29 pgs.
"U.S. Appl. No. 15/703,713, Notice of Allowance dated Sep. 25, 2018", 11 pgs.
"U.S. Appl. No. 15/703,713, Response Filed Jun. 15, 2018 to Non-Final Office Action dated Mar. 27, 2018", 16 pgs.
"U.S. Appl. No. 15/703,713, Preliminary Amendment filed Sep. 28, 2017", 7 pgs.
"U.S. Appl. No. 15/720,866, Non Final Office Action dated Sep. 9, 2019", 12 pgs.
"U.S. Appl. No. 15/720,866, Response filed Jul. 10, 2019 to Restriction Requirement dated May 14, 2019", 10 pgs.
"U.S. Appl. No. 15/720,866, Response filed Nov. 13, 2017 to Non Final Office Action dated Sep. 14, 2017", 10 pgs.
"U.S. Appl. No. 15/720,866, Restriction Requirement dated May 14, 2019", 7 pgs.
"U.S. Appl. No. 15/720,866, Preliminary Amendment filed Nov. 13, 2017", 9 pgs.
"U.S. Appl. No. 15/827,654, Examiner Interview Summary dated Apr. 26, 2019", 4 pgs.
"U.S. Appl. No. 15/827,654, Final Office Action dated Feb. 19, 2019", 19 pgs.
"U.S. Appl. No. 15/827,654, Non Final Office Action dated Sep. 7, 2018", 21 pgs.
"U.S. Appl. No. 15/827,654, Notice of Allowance dated Jul. 8, 2019", 8 pgs.
"U.S. Appl. No. 15/827,654, Preliminary Amendment filed Dec. 22, 2017", 11 pgs.
"U.S. Appl. No. 15/827,654, Response Filed May 20, 2019 to Final Office Action dated Feb. 19, 2019", 17 pgs.
"U.S. Appl. No. 15/827,654, Response filed Jun. 6, 2018 to Restriction Requirement dated Apr. 6, 2018", 11 pgs.
"U.S. Appl. No. 15/827,654, Response filed to Non Final Office Action dated Sep. 7, 2018", 24 pgs.
"U.S. Appl. No. 15/827,654, Restriction Requirement dated Apr. 6, 2018", 6 pgs.
"U.S. Appl. No. 15/915,886, Non Final Office Action dated Aug. 2, 2019", 9 pgs.
"U.S. Appl. No. 16/530,423, Preliminary Amendment filed Aug. 28, 2019", 7 pgs.
"Australian Application Serial No. 2011286306, First Examiner Report dated Jun. 19, 2013", 4 pgs.
"Australian Application Serial No. 2011286306, Response filed Jun. 3, 2014 to First Examiner Report dated Jun. 19, 2013", 16 pgs.
"Australian Application Serial No. 2011286307, First Examiner Report dated Oct. 17, 2013", 2 pgs.
"Australian Application Serial No. 2011286307, Response filed May 21, 2014 to First Examiner Report dated Oct. 17, 2013", 16 pgs.
"Australian Application Serial No. 2011286308, First Examiner Report dated Jun. 21, 2013", 4 pgs.
"Australian Application Serial No. 2011286308, Response filed Jun. 6, 2014 First Examiner Report dated Jun. 21, 2013", 19 pgs.
"Australian Application Serial No. 2011286309, First Examiner Report dated Jun. 21, 2013", 3 pgs.
"Australian Application Serial No. 2011286309, Response filed Jun. 10, 2014 to First Examiner Report dated Jun. 21, 2013", 4 pgs.
"Australian Application Serial No. 2011343440, First Examiner Report dated Feb. 17, 2014", 3 pgs.
"Australian Application Serial No. 2011343440, Response filed Mar. 21, 2014 to Office Action dated Feb. 17, 2014", 1 pg.
"Australian Application Serial No. 2012341026, First Examiner Report dated Jul. 14, 2014", 2 pgs.
"Australian Application Serial No. 2012341026, Response filed Nov. 21, 2014 to First Examiner Report dated Jul. 14, 2014", 1 pg.
"Australian Application Serial No. 2012341026, Statement of Proposed Amendment filed Jun. 18, 2014", 25 pgs.
"Australian Application Serial No. 2012368262, First Examiner Report dated Nov. 2, 2016", 4 pgs.
"Australian Application Serial No. 2012368262, Response filed Jan. 17, 2017 to Office Action dated Nov. 2, 2016", 21 pgs.
"Australian Application Serial No. 2012368262, Response filed May 15, 2017 to Subsequent Examiners Report dated Mar. 16, 2017", 2 pgs.
"Australian Application Serial No. 2012368262, Subsequent Examiners Report dated Mar. 16, 2017", 3 pgs.
"Australian Application Serial No. 2013238046, First Examiner Report dated Nov. 26, 2015", 2 pgs.
"Australian Application Serial No. 2013238046, Response filed Feb. 2, 2016 to First Examiner Report dated Nov. 26, 2015", 1 pg.
"Australian Application Serial No. 2013238054, First Examiner Report dated Oct. 17, 2016", 4 pgs.
"Australian Application Serial No. 2013238054, Response filed Jan. 18, 2017 to First Examiner Report dated Oct. 17, 2016", 9 pgs.
"Australian Application Serial No. 2014250709, First Examiner Report dated Dec. 21, 2015", 3 pgs.
"Australian Application Serial No. 2014250709, Response filed May 4, 2016 to First Examiner Report dated Dec. 21, 2015", 12 pgs.
"Australian Application Serial No. 2014250709, Subsequent Examiners Report dated May 31, 2016", 6 pgs.
"Australian Application Serial No. 2014250710, First Examiner Report dated Dec. 11, 2015", 7 pgs.
"Australian Application Serial No. 2014250710, Response filed Mar. 22, 2016 to First Examiner Report dated Dec. 11, 2015", 18 pgs.

(56) References Cited

OTHER PUBLICATIONS

"Australian Application Serial No. 2014250710, Response filed May 4, 2016 to Subsequent Examiners Report dated Mar. 23, 2016", 15 pgs.
"Australian Application Serial No. 2014250710, Subsequent Examiners Report dated Mar. 23, 2016", 3 pgs.
"Australian Application Serial No. 2014250711, First Examiner Report dated Feb. 12, 2016", 7 pgs.
"Australian Application Serial No. 2014250711, Response filed Apr. 27, 2016 to First Examiner Report dated Feb. 12, 2016", 32 pgs.
"Australian Application Serial No. 2015201511, First Examination Report dated Apr. 18, 2016", 2 pgs.
"Australian Application Serial No. 2015201511, Response filed Jun. 30, 2016 to First Examiner Report dated Apr. 18, 2016", 12 pgs.
"Australian Application Serial No. 2015238820, First Examination Report dated May 30, 2017", 3 pgs.
"Australian Application Serial No. 2015238820, Response filed Jul. 12, 2017 to First Examination Report dated May 30, 2017", 12 pgs.
"Australian Application Serial No. 2016225911, First Examiners Report dated Jun. 2, 2017", 3 pgs.
"Australian Application Serial No. 2016225911, Response filed Aug. 22, 2017 to First Examiners Report dated Jun. 2, 2017", 18 pgs.
"Australian Application Serial No. 2017235987, First Examination Report dated Nov. 1, 2018", 4 pgs.
"Australian Application Serial No. 2017251736, First Examiners Report dated Oct. 31, 2017", 2 pgs.
"Bi-Cruciate Stabilized Knee System", Design Rationale, Smith & Nephew Journal, (2006), 20 pgs.
"Canadian Application Serial No. 2,806,321, Office Action dated Jan. 15, 2018", 3 pgs.
"Canadian Application Serial No. 2,806,321, Response filed Jan. 22, 2018 to Office Action dated Jan. 15, 2018", 7 pgs.
"Canadian Application Serial No. 2,806,321, Response filed Dec. 6, 2017 to Office Action dated Jun. 15, 2017", 12 pgs.
"Canadian Application Serial No. 2,806,325, Office Action dated Mar. 14, 2016", 4 pgs.
"Canadian Application Serial No. 2,806,325, Response filed Sep. 14, 2016 to Office Action dated Mar. 14, 2016", 17 pgs.
"Canadian Application Serial No. 2,806,326, Examiner's Rule 30(2) Requisition dated Sep. 20, 2018", 4 pgs.
"Canadian Application Serial No. 2,806,326, Office Action dated Feb. 8, 2018", 4 pgs.
"Canadian Application Serial No. 2,806,326, Office Action dated Jun. 19, 2017", 3 pgs.
"Canadian Application Serial No. 2,806,326, Response Filed Mar. 20, 2019 to Examiner's Rule 30(2) Requisition dated Sep. 20, 2018", 4 pgs.
"Canadian Application Serial No. 2,806,326, Response filed Jul. 20, 2018 to Office Action dated Feb. 8, 2018", 12 pgs.
"Canadian Application Serial No. 2,821,927, Office Action dated Jan. 25, 2018", 6 pgs.
"Canadian Application Serial No. 2,821,927, Response filed Jul. 18, 2018 to Office Action dated Jan. 25, 2018", 10 pgs.
"Canadian Application Serial No. 2,821,927, Voluntary Amendment dated Jun. 14, 2013", 7 pgs.
"Canadian Application Serial No. 2,824,527, Office Action dated Mar. 17, 2014", 2 pgs.
"Canadian Application Serial No. 2,824,527, Response filed Sep. 17, 2014 to Office Action dated Mar. 17, 2014", 14 pgs.
"Canadian Application Serial No. 2,856,070, Preliminary Amendment filed May 25, 2015", 27 pgs.
"Canadian Application Serial No. 2,856,571 Response filed Jan. 22, 2015 to Office Action dated Jul. 22, 2014", 24 pgs.
"Canadian Application Serial No. 2,856,571, Office Action dated Jul. 22, 2014", 2 pgs.
"Canadian Application Serial No. 2,863,375, Office Action dated Apr. 20, 2018", 3 pgs.
"Canadian Application Serial No. 2,863,375, Response filed Oct. 22, 2018 Office Action dated Apr. 20, 2018", 12 pgs.
"Canadian Application Serial No. 2,868,825, Office Action dated Dec. 27, 2018", 3 pgs.
"Canadian Application Serial No. 2,956,119, Examiner's Rule 30(2) Requisition dated Sep. 27, 2018", 4 pgs.
"Canadian Application Serial No. 2,956,119, Office Action dated Jan. 22, 2018", 3 pgs.
"Canadian Application Serial No. 2,956,119, Response Filed Mar. 27, 2019 to Examiner's Rule 30(2) Requisition dated Sep. 27, 2018", 7 pgs.
"Canadian Application Serial No. 2,989,184, Office Action dated Oct. 1, 2018", 4 pgs.
"Canadian Application Serial No. 2,989,184, Response filed Apr. 1, 2019 to Office Action dated Oct. 1, 2018", 10 pgs.
"Canadian Application Serial No. 2,806,321, Office Action dated Jun. 15, 2017", 3 pgs.
"Chinese Application Serial No. 201180045673.3, Office Action dated Feb. 14, 2016", (W/English Translation), 17 pgs.
"Chinese Application Serial No. 201180045673.3, Office Action dated Mar. 29, 2015", (W/English Translation), 6 pgs.
"Chinese Application Serial No. 201180045673.3, Office Action dated Aug. 12, 2015", (W/English Translation), 7 pgs.
"Chinese Application Serial No. 201180045673.3, Response filed Apr. 19, 2016 to Office Action dated Feb. 14, 2016", No English Translation, 11 pqs.
"Chinese Application Serial No. 201180045673.3, Response filed Jun. 19, 2015 to Office Action dated Mar. 29, 2015", (W/ English translation of claims), 11 pgs.
"Chinese Application Serial No. 201180045673.3, Response filed Oct. 27, 2015 to Office Action dated Aug. 12, 2015", (W/ English translation of claims), 9 pgs.
"Chinese Application Serial No. 201180045681.8, Office Action dated Jan. 22, 2015", (W/English Translation), 11 pgs.
"Chinese Application Serial No. 201180045681.8, Response filed May 14, 2015 to Office Action dated Jan. 22, 2015", W/ English Claims, 17 pgs.
"Chinese Application Serial No. 201180045683.7, Office Action dated Mar. 9, 2015", (W/English Translation), 6 pgs.
"Chinese Application Serial No. 201180045683.7, Response filed Jul. 14, 2015 to Office Action dated Mar. 9, 2015", (W/ English translation of claims), 30 pgs.
"Chinese Application Serial No. 201180045689.4, Office Action dated Jan. 5, 2015", (W/English Translation), 4 pgs.
"Chinese Application Serial No. 201180045689.4, Office Action dated Feb. 2, 2016", w/English Translation, 11 pgs.
"Chinese Application Serial No. 201180045689.4, Office Action dated Aug. 5, 2015", (W/English Translation), 11 pgs.
"Chinese Application Serial No. 201180045689.4, Response filed Apr. 7, 2016 to Office Action dated Feb. 2, 2016", No English Translation, 8 pgs.
"Chinese Application Serial No. 201180045689.4, Response filed May 1, 2015 to Office Action dated Jan. 5, 2015", W/ English Claims, 13 pgs.
"Chinese Application Serial No. 201180045689.4,Response filed Oct. 21, 2015 to Office Action dated Aug. 5, 2015", No English Claims.
"Chinese Application Serial No. 201180067430.X, Office Action dated Aug. 28, 2014", (W/English Translation), 8 pgs.
"Chinese Application Serial No. 201180067430.X, Response filed Jan. 4, 2015 to Office Action dated Sep. 26, 2014", (W/ English Translation), 14 pgs.
"Chinese Application Serial No. 201180067757.7, Office Action dated Mar. 2, 2015", (W/English Translation), 18 pgs.
"Chinese Application Serial No. 201180067757.7, Office Action dated Jun. 1, 2016", (W/English Translation), 10 pgs.
"Chinese Application Serial No. 201180067757.7, Office Action dated Nov. 16, 2015", (W/English Translation), 17 pgs.
"Chinese Application Serial No. 201180067757.7, Response filed Jun. 27, 2016 to Office Action dated Nov. 16, 2015", (W/ English Translation of Claims), 12 pgs.
"Chinese Application Serial No. 201180067757.7, Response filed Jul. 10, 2015 to Office Action dated Mar. 2, 2015", (W/ English Translation), 13 pgs.

(56) References Cited

OTHER PUBLICATIONS

"Chinese Application Serial No. 201180067757.7, Response filed Aug. 11, 2016 to Office Action dated Jun. 1, 2016", (W/ English Translation Of Claims), 9 pgs.
"Chinese Application Serial No. 201180067757.7, Voluntary Amendment dated Feb. 14, 2014", (W/ English Translation of Claims), 8 pgs.
"Chinese Application Serial No. 201280067473.2, Office Action dated Feb. 1, 2016", (W/English Translation), 4 pgs.
"Chinese Application Serial No. 201280067473.2, Office Action dated May 20, 2015", (W/English Translation), 15 pgs.
"Chinese Application Serial No. 201280067473.2, Office Action dated Nov. 20, 2015", W/English Translation of Claims, 7 pgs.
"Chinese Application Serial No. 201280067473.2, Response filed Apr. 7, 2016 to Office Action dated Feb. 1, 2016", (W/ English translation of claims), 11 pgs.
"Chinese Application Serial No. 201280067473.2, Response filed Sep. 7, 2015 to Office Action dated May 20, 2015", (W/ English translation of claims), 12 pgs.
"Chinese Application Serial No. 201280067473.2, Response filed Dec. 4, 2015 to Office Action dated Nov. 20, 2015", w/English Claims, 11 pgs.
"Chinese Application Serial No. 201280067481.7, Office Action dated Sep. 30, 2015", (W/English Translation), 7 pgs.
"Chinese Application Serial No. 201280071940.9, Office Action dated Jul. 22, 2015", (W/English Translation), 13 pgs.
"Chinese Application Serial No. 201280071940.9, Preliminary Amendment filed Mar. 23, 2015", W/ English Claims, 11 pgs.
"Chinese Application Serial No. 201380028572.4, Office Action dated Aug. 13, 2015", (W/English Translation), 16 pgs.
"Chinese Application Serial No. 201380028683.5, Office Action dated Jun. 27, 2016", (W/English Translation), 8 pgs.
"Chinese Application Serial No. 201380028683.5, Office Action dated Nov. 4, 2015", (W/English Translation), 16 pgs.
"Chinese Application Serial No. 201380028683.5, Office Action dated Dec. 30, 2016", (W/English Translation), 4 pgs.
"Chinese Application Serial No. 201380028683.5, Response filed Feb. 8, 2017 to Office Action dated Dec. 30, 2016", (W/ English Translation), 13 pgs.
"Chinese Application Serial No. 201380028683.5, Response filed Mar. 18, 2016 to Office Action dated Nov. 4, 2015", (W/ English Translation of Claims), 11 pgs.
"Chinese Application Serial No. 201380028683.5, Response filed Sep. 6, 2016 to Office Action dated Jun. 27, 2016", (W/ English Translation of Claims), 11 pgs.
"Chinese Application Serial No. 201510394094.X, Office Action dated May 24, 2017", (W/English Translation), 11 pgs.
"Chinese Application Serial No. 201510394094.X, Office Action dated Aug. 30, 2016", (W/English Translation), 14 pgs.
"Chinese Application Serial No. 201510394094.X, Office Action dated Nov. 3, 2017", (W/English Translation), 10 pgs.
"Chinese Application Serial No. 201510394094.X, Response filed Jan. 16, 2017 to Office Action dated Aug. 30, 2016", (W/ English Translation of Claims), 11 pgs.
"Chinese Application Serial No. 201510394094.X, Response filed Jan. 18, 2018 to Office Action dated Nov. 3, 2017", (W/ English Claims), 10 pgs.
"Chinese Application Serial No. 201510394094.X, Response filed Jul. 10, 2017 to Office Action dated May 24, 2017", (W/ English Translation), 10 pgs.
"Chinese Application Serial No. 201510640436.1, Office Action dated Sep. 28, 2016", (W/English Translation), 13 pgs.
"Chinese Application Serial No. 201510640436.1, Response filed Feb. 16, 2017 to Office Action dated Sep. 28, 2016", (W/ English Translation), 18 pgs.
"Chinese Application Serial No. 201610634595.5, Office Action dated Apr. 20, 2018", (W/English Translation), 8 pgs.
"Chinese Application Serial No. 201610634595.5, Office Action dated Jun. 21, 2017", w/English Translation, 9 pgs.
"Chinese Application Serial No. 201610634595.5, Response filed Jun. 4, 2018 to Office Action dated Apr. 20, 2018", (W/ English Translation of Claims), 8 pgs.
"Chinese Application Serial No. 201610634595.5, Response filed Nov. 3, 2017 to Office Action dated Jun. 21, 2017", w/English Claims, 8 pgs.
"Chinese Application Serial No. 201610685172.6, Office Action dated Apr. 10, 2017", (W/English Translation), 11 pgs.
"Chinese Application Serial No. 201610685172.6, Office Action dated Sep. 28, 2017", (W/English Translation), 9 pgs.
"Chinese Application Serial No. 201610685172.6, Response filed Dec. 13, 2017 to Office Action dated Sep. 28, 2017", (W/ English Claims), 13 pgs.
"Chinese Application Serial No. 201680061268.3, Office Action dated Apr. 24, 2019", (W/English Translation), 11 pgs.
"Chinese Application Serial No. 201680061268.3, Response filed Aug. 21, 2019 to Office Action dated Apr. 24, 2019", (W/ English Claims), 8 pgs.
"Complete Knee Solution Surgical Technique for the CR-Flex Fixed Bearing Knee", Zimmer Nexgen, (2003), 22 pgs.
"European Application Serial No. 11738918.9, Examination Notification Art. 94(3) dated Oct. 23, 2014", 5 pgs.
"European Application Serial No. 11738918.9, Preliminary Amendment dated Sep. 24, 2013", 11 pgs.
"European Application Serial No. 11738918.9, Response filed Mar. 2, 2015 to Examination Notification Art. 94(3) dated Oct. 23, 2014", 14 pgs.
"European Application Serial No. 11738919.7, Examination Notification Art. 94(3) dated Jul. 7, 2014", 4 pgs.
"European Application Serial No. 11738919.7, Preliminary Amendment filed Nov. 4, 2013", 25 pgs.
"European Application Serial No. 11738919.7, Response filed Nov. 13, 2014 to Examination Notification Art. 94(3) dated Jul. 7, 2014", 14 pgs.
"European Application Serial No. 11738920.5, Communication Pursuant to Article 94(3) EPC dated Mar. 15, 2016", 4 pgs.
"European Application Serial No. 11738920.5, Preliminary Amendment Sep. 24, 2013", 9 pgs.
"European Application Serial No. 11738920.5, Response filed Jul. 25, 2016 to Communication Pursuant to Article 94(3) EPC dated Mar. 15, 2016", 6 pgs.
"European Application Serial No. 11738920.5, Response filed Sep. 24, 2013 to Communication pursuant to Rules 161(2) and 162 EPC dated Mar. 15, 2013", 22 pgs.
"European Application Serial No. 11758060.5, Communication Pursuant to Article 94(3) EPC dated Jul. 12, 2016", 3 pgs.
"European Application Serial No. 11758060.5, Communication Pursuant to Article 94(3) EPC dated Dec. 11, 2015", 4 pgs.
"European Application Serial No. 11758060.5, Preliminary Amendment filed Nov. 4, 2013", 15 pgs.
"European Application Serial No. 11758060.5, Response filed Apr. 21, 2016 to Communication Pursuant to Article 94(3) EPC dated Dec. 11, 2015", 16 pgs.
"European Application Serial No. 11758060.5, Response filed Nov. 15, 2016 to Communication Pursuant to Article 94(3) EPC dated Jul. 12, 2016", 23 pgs.
"European Application Serial No. 11802835.6, Communication Pursuant to Article 94(3) EPC dated Dec. 11, 2017", 4 pgs.
"European Application Serial No. 11802835.6, Response filed Apr. 23, 2018 to Office Action dated Dec. 11, 2017", 16 pgs.
"European Application Serial No. 11808493.8, Communication Pursuant to Article 94(3) EPC dated Dec. 7, 2015", 4 pgs.
"European Application Serial No. 11808493.8, Examination Notification Art. 94(3) dated Feb. 20, 2015", 6 pgs.
"European Application Serial No. 11808493.8, Response filed Feb. 26, 2014 to Communication pursuant to Rules 161(1) and 162 EPC dated Aug. 16, 2013", 14 pgs.
"European Application Serial No. 11808493,8, Response filed Apr. 18, 2016 to Communication Pursuant to Article 94(3) EPC dated Dec. 7, 2015", 15 pgs.
"European Application Serial No. 11808493.8, Response filed Jul. 2, 2015 to Examination Notification Art. 94(3) dated Feb. 20, 2015", 13 pgs.

(56) References Cited

OTHER PUBLICATIONS

"European Application Serial No. 11815029.1, Communication Pursuant to Article 94(3) EPC dated Sep. 29, 2016", 4 pgs.
"European Application Serial No. 11815029.1, Extended European Search Report dated Dec. 10, 2013", 8 pgs.
"European Application Serial No. 11815029.1, Response filed Apr. 10, 2017 to Communication Pursuant to Article 94(3) EPC dated Sep. 29, 2016", 22 pgs.
"European Application Serial No. 11815029.1, Response filed Jul. 21, 2014 Extended European Search Report dated Dec. 10, 2013", 15 pgs.
"European Application Serial No. 12718882.9, Communication Pursuant to Article 94(3) EPC dated Dec. 1, 2015", 11 pgs.
"European Application Serial No. 12718882.9, Response filed Feb. 10, 2015 to Communication Pursuant to Rules 161(1) and 162 EPC dated Jul. 31, 2014", 11 pgs.
"European Application Serial No. 12718882.9, Response filed Apr. 11, 2016 to Communication Pursuant to Article 94(3) EPC dated Dec. 1, 2015", 12 pgs.
"European Application Serial No. 12718883.7, Communication Pursuant to Article 94(3) EPC dated Dec. 2, 2015", 4 pgs.
"European Application Serial No. 12718883.7, Communication Pursuant to Rules 161(1) and 162 EPC dated Jul. 31, 2014", 2 pgs.
"European Application Serial No. 12718883.7, Intention to Grant dated May 20, 2016", 5 pgs.
"European Application Serial No. 12718883.7, Response filed Feb. 10, 2015 to Communication Pursuant to Rules 161(1) and 162 EPC dated Jul. 31, 2014", 16 pgs.
"European Application Serial No. 12718883.7, Response filed Apr. 12, 2016 to Communication Pursuant to Article 94(3) EPC dated Dec. 2, 2015", 30 pgs.
"European Application Serial No. 12719236.7 Response filed Feb. 9, 2015 to Communication Pursuant to Rules 161(1) and 162 EPC dated Jul. 30, 2014", 10 pgs.
"European Application Serial No. 12719236.7, Decision to Grant dated Feb. 18, 2016", 3 pgs.
"European Application Serial No. 12719236.7, Office Action dated Aug. 27, 2015", 7 pgs.
"European Application Serial No. 1270352.9 Response filed Feb. 9, 2015 to Communication Pursuant to Rules 161(1) and 162 EPC dated Jul. 30, 2014", 10 pgs.
"European Application Serial No. 12756058.9, Communication Pursuant to Article 94(3) EPC dated Feb. 18, 2019", 4 pgs.
"European Application Serial No. 12756058.9, Office Action dated Jan. 17, 2017", 5 Pgs.
"European Application Serial No. 12756058.9, Preliminary Amendment filed Apr. 20, 2015", 12 pgs.
"European Application Serial No. 12756058.9, Response filed May 26, 2017 to Office Action dated Jan. 17, 2017", 16 pgs.
"European Application Serial No. 12756058.9, Response filed Jun. 28, 2019 to Communication Pursuant to Article 94(3) EPC dated Feb. 18, 2019", 21 pgs.
"European Application Serial No. 12756869.9 Response filed Feb. 10, 2015 to Communication Pursuant to Rule 161(1) and 162 EPC dated Jul. 31, 2014", 14 pgs.
"European Application Serial No. 12756869.9, Examination Notification Art. 94(3) dated Jul. 2, 2015", 4 pgs.
"European Application Serial No. 12756869.9, Response filed Nov. 12, 2015 to Examination Notification Art. 94(3) dated Jul. 2, 2015", 28 pgs.
"European Application Serial No. 13716636.9, Communication Pursuant to Article 9 4(3) EPC dated Nov. 16, 2015", 4 pgs.
"European Application Serial No. 13716636.9, Communication Pursuant to Article 94(3) EPC dated Nov. 17, 2016", 4 pgs.
"European Application Serial No. 13716636.9, Communication Pursuant to Article 94(3) EPC dated Jun. 6, 2016", 5 pgs.
"European Application Serial No. 13716636.9, Communication pursuant to Rules 161(1) and 162 EPC dated Dec. 12, 2014", 2 pgs.
"European Application Serial No. 13716636.9, Response filed Mar. 24, 2016 to Communication Pursuant to Article 94(3) EPC dated Nov. 16, 2015", 18 pgs.
"European Application Serial No. 13716636.9, Response filed Mar. 27, 2017 to Communication Pursuant to Article 94(3) EPC dated Nov. 17, 2016", 15 pgs.
"European Application Serial No. 13716636.9, Response filed Jun. 22, 2015 to Communication pursuant to Rules 161(1) and 162 EPC dated Dec. 12, 2014", 10 pgs.
"European Application Serial No. 13716636.9, Response filed Oct. 17, 2016 to Communication Pursuant to Article 94(3) EPC dated Jun. 6, 2016", 5 pgs.
"European Application Serial No. 14190180.1, Extended European Search Report dated Sep. 24, 2015", 8 pgs.
"European Application Serial No. 15160934.4, Communication Pursuant to Article 94(3) EPC dated Apr. 26, 2018", 5 pgs.
"European Application Serial No. 15160934.4, Extended European Search Report dated Jun. 1, 2016", 8 pgs.
"European Application Serial No. 15160934.4, Response filed Aug. 30, 2018 to Communication Pursuant to Article 94(3) EPC dated Apr. 26, 2018", 63 pgs.
"European Application Serial No. 15160934.4, Response filed Dec. 21, 2016 to Extended European Search Report dated Jun. 1, 2016", 5 pgs.
"European Application Serial No. 15174394.5, Extended European Search Report dated Mar. 21, 2016", 8 pgs.
"European Application Serial No. 15174394.5, Response filed Nov. 18, 2016 to Extended European Search Report dated Mar. 21, 2016", 12 pgs.
"European Application Serial No. 15191781.2, Communication Pursuant to Article 94(3) EPC dated Jan. 8, 2018", 4 pgs.
"European Application Serial No. 15191781.2, Extended European Search Report dated Mar. 1, 2017", 8 pgs.
"European Application Serial No. 15191781.2, Response filed May 17, 2018 to Communication Pursuant to Article 94(3) EPC dated Jan. 8, 2018", 58 pgs.
"European Application Serial No. 15191781.2, Response filed Sep. 28, 2017 to Extended European Search Report dated Mar. 1, 2017", 14pgs.
"European Application Serial No. 16156228.5, Extended European Search Report dated May 11, 2017", 5 pgs.
"European Application Serial No. 16183635.8, Extended European Search Report dated Jun. 30, 2017", 9 pgs.
"European Application Serial No. 16183635.8, Response filed Mar. 27, 2018 to Extended European Search Report dated Jun. 30, 2017", 8 pgs.
"European Application Serial No. 16189084.3, Extended European Search Report dated Oct. 9, 2017", 9 pgs.
"European Application Serial No. 16189084.3, Response filed May 10, 2018 to Extended European Search Report dated Oct. 9, 2017", 20 pgs.
"European Application Serial No. 16770657.1, Communication Pursuant to Article 94(3) EPC dated May 20, 2019", 3 pgs.
"European Application Serial No. 16770657.1, Response filed Nov. 26, 18 to Office Action dated May 14, 2018", 17 pgs.
"European Application Serial No. 17157909.7, Extended European Search Report dated Jul. 17, 2018", 7 pgs.
"European Application Serial No. 17157909.7, Response Filed Feb. 15, 2019 to Extended European Search Report dated Jul. 17, 2018", 37 pgs.
"European Application Serial No. 17163432.2, Extended European Search Report dated May 14, 2018", 6 pgs.
"European Application Serial No. 17163440.5, Extended European Search Report dated Jan. 3, 2019", 16 pgs.
"European Application Serial No. 17163440.5, Partial European Search Report dated Jul. 23, 2018", 15 pgs.
"European Application Serial No. 17163440.5, Response filed Jul. 22, 2019 to Extended European Search Report dated Jan. 3, 2019", 14 pgs.
"European Application Serial No. 17168095.2, Extended European Search Report dated Jun. 8, 2018", 8 pgs.

(56) References Cited

OTHER PUBLICATIONS

"European Application Serial No. 17168095.2, Response Filed Jan. 17, 2019 Extended European Search Report dated Jun. 8, 2018", 29 pgs.
"European Application Serial No. 17168308.9, Extended European Search Report dated Jun. 13, 2018", 8 pgs.
"European Application Serial No. 17168308.9, Response Filed Jan. 17, 2019 to Extended European Search Report dated Jun. 13, 2018", 24 pgs.
"Gender Solutions Natural Knee Flex System: Because Men and Women are Different", Zimmer, Inc., (2007, 2009), 6 pg.
"Gender Solutions Natural Knee Flex System: Surgical Technique", Zimmer, Inc., (2007, 2008, 2009), 36 pgs.
"Gender Solutions Natural-Knee Flex System", Zimmer, Inc., (2007, 2009), 6 pgs.
"Indian Application Serial No. 1544/DELNP/2013, Office Action dated May 21, 2019", (W/English Translation), 10 pgs.
"International Application Serial No. PCT/US2011/045077, International Preliminary Report on Patentability dated Jul. 5, 2012", 23 pgs.
"International Application Serial No. PCT/US2011/045077, International Search Report and Written Opinion dated Jan. 9, 2012", 15 pgs.
"International Application Serial No. PCT/US2011/045078, International Preliminary Report on Patentability dated Feb. 7, 2013", 11 pgs.
"International Application Serial No. PCT/US2011/045078, International Search Report and Written Opinion dated Jan. 9, 2012", 14 pgs.
"International Application Serial No. PCT/US2011/045080, International Preliminary Report on Patentability dated Feb. 7, 2013", 13 pgs.
"International Application Serial No. PCT/US2011/045080, International Search Report dated Jan. 9, 2012", 7 pgs.
"International Application Serial No. PCT/US2011/045080, Written Opinion dated Jan. 9, 2012", 11 pgs.
"International Application Serial No. PCT/US2011/045082, International Preliminary Report on Patentability dated Feb. 7, 2013", 11 pgs.
"International Application Serial No. PCT/US2011/045082, International Search Report dated Jan. 9, 2012", 5 pgs.
"International Application Serial No. PCT/US2011/045082, Written Opinion dated Jan. 9, 2012", 10 pgs.
"International Application Serial No. PCT/US2011/045083, International Preliminary Report on Patentability dated Feb. 7, 2013", 8 pgs.
"International Application Serial No. PCT/US2011/045083, International Search Report dated Dec. 7, 2011", 2 pgs.
"International Application Serial No. PCT/US2011/045083, Written Opinion dated Dec. 7, 2011", 6 pgs.
"International Application Serial No. PCT/US2011/051021, International Preliminary Report on Patentability dated Mar. 21, 2013", 8 pgs.
"International Application Serial No. PCT/US2011/051021, International Search Report dated Nov. 23, 2011", 12 pgs.
"International Application Serial No. PCT/US2011/051021, Written Opinion dated Nov. 23, 2011", 7 pgs.
"International Application Serial No. PCT/US2011/064435, International Preliminary Report on Patentability dated Jun. 27, 2013", 9 pgs.
"International Application Serial No. PCT/US2011/064435, Search Report dated Jun. 21, 2012", 5 pgs.
"International Application Serial No. PCT/US2011/064435, Written Opinion dated Jun. 21, 2012", 7 pgs.
"International Application Serial No. PCT/US2011/065683, International Preliminary Report on Patentability dated Jun. 27, 2013", 11 pgs.
"International Application Serial No. PCT/US2011/065683, International Search Report dated Apr. 24, 2012", 12 pgs.
"International Application Serial No. PCT/US2011/065683, Written Opinion dated Apr. 24, 2012", 10 pgs.
"International Application Serial No. PCT/US2012/035679, International Preliminary Report on Patentability dated May 30, 2014", 8 pgs.
"International Application Serial No. PCT/US2012/035679, International Search Report dated Jun. 8, 2012", 4 pgs.
"International Application Serial No. PCT/US2012/035679, Written Opinion dated Jun. 8, 2012", 7 pgs.
"International Application Serial No. PCT/US2012/035680, International Preliminary Report on Patentability dated May 30, 2014", 13 pgs.
"International Application Serial No. PCT/US2012/035680, Search Report dated Oct. 9, 2012", 7 pgs.
"International Application Serial No. PCT/US2012/035680, Written Opinion dated Oct. 9, 2012", 11 pgs.
"International Application Serial No. PCT/US2012/035683, International Preliminary Report on Patentability dated May 30, 2014", 9 pgs.
"International Application Serial No. PCT/US2012/035683, International Search Report and Written Opinion dated Jun. 5, 2012", 12 pgs.
"International Application Serial No. PCT/US2012/035684, International Preliminary Report on Patentability dated May 30, 2014", 14 pgs.
"International Application Serial No. PCT/US2012/035684, International Search Report dated Aug. 8, 2012", 9 pgs.
"International Application Serial No. PCT/US2012/035684, Written Opinion dated Jun. 8, 2012", 12 pgs.
"International Application Serial No. PCT/US2012/052132, International Preliminary Report on Patentability dated Jun. 5, 2014", 12 pgs.
"International Application Serial No. PCT/US2012/052132, International Search Report dated Jan. 10, 2013", 5 pgs.
"International Application Serial No. PCT/US2012/052132, Invitation to Pay Additional Fees and Partial Search Report dated Nov. 15, 2012", 7 pgs.
"International Application Serial No. PCT/US2012/052132, Written Opinion dated Jan. 10, 2013", 10 pgs.
"International Application Serial No. PCT/US2012/052340, International Preliminary Report on Patentability dated Aug. 14, 2014", 8 pgs.
"International Application Serial No. PCT/US2012/052340, Search Report dated Oct. 12, 2012", 4 pgs.
"International Application Serial No. PCT/US2012/052340, Written Opinion dated Oct. 12, 2012", 6 pgs.
"International Application Serial No. PCT/US2013/034286, International Preliminary Report on Patentability dated Oct. 9, 2014", 8 pgs.
"International Application Serial No. PCT/US2013/034286, International Search Report dated Jun. 25, 2013", 6 pgs.
"International Application Serial No. PCT/US2013/034286, Written Opinion dated Jun. 25, 2013", 6 pgs.
"International Application Serial No. PCT/US2013/034293, International Preliminary Report on Patentability dated Oct. 9, 2014", 9 pgs.
"International Application Serial No. PCT/US2013/034293, International Search Report dated Jun. 25, 2013", 6 pgs.
"International Application Serial No. PCT/US2013/034293, Written Opinion dated Jun. 25, 2013", 7 pgs.
"International Application Serial No. PCT/US2016/052163, International Preliminary Report on Patentability dated Apr. 5, 2018", 10 pgs.
"International Application Serial No. PCT/US2016/052163, International Search Report dated Jan. 20, 2017", 7 pgs.
"International Application Serial No. PCT/US2016/052163, Invitation to Pay Add'l Fees and Partial Search Report dated Nov. 7, 2016", 7 pgs.
"International Application Serial No. PCT/US2016/052163, Written Opinion dated Jan. 20, 2017", 8 pgs.
"International Application Serial No. PCT/US2018/021571, International Preliminary Report on Patentability dated Sep. 19, 2019", 8 pgs.

(56) References Cited

OTHER PUBLICATIONS

"International Application Serial No. PCT/US2018/021571, International Search Report dated Jun. 7, 2018", 6 pgs.
"International Application Serial No. PCT/US2018/021571, Written Opinion dated Jun. 7, 2018", 6 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995, 1997, 1998), 36 pgs.
"Japanese Application Serial No. 2015-162707, Office Action dated Jun. 28, 2016", (W/English Translation), 8 pgs.
"Japanese Application Serial No. 2013-521854, Notice of Reason for Rejection dated Sep. 16, 2014", (W/ English Translation), 6 pgs.
"Japanese Application Serial No. 2013-521854, Response filed Dec. 16, 2014 to Notice of Reason for Rejection dated Sep. 16, 2014", W/ English Claims, 11 pgs.
"Japanese Application Serial No. 2013-521855, Amendment filed Jul. 22, 2014", (W/ English Translation), 20 pgs.
"Japanese Application Serial No. 2013-521855, Office Action dated Mar. 24, 2015", W/ English Translation, 8 pgs.
"Japanese Application Serial No. 2013-521856, Notice of Allowance dated Jan. 5, 2016", w/English Translation, 6 pgs.
"Japanese Application Serial No. 2013-521856, Office Action dated Sep. 1, 2015", (W/ English Translation), 5 pgs.
"Japanese Application Serial No. 2013-521856, Response filed Dec. 1, 2015 to Office Action dated Sep. 1, 2015", w/English Translation, 9 pgs.
"Japanese Application Serial No. 2013-521857, Notice of Allowance dated Feb. 9, 2016", w/English Translation, 6 pgs.
"Japanese Application Serial No. 2013-521857, Notice of Reasons for Rejection dated Aug. 18, 2015", (W/ English Translation), 6 pgs.
"Japanese Application Serial No. 2013-521857, Preliminary Amendment filed May 18, 2014", (W/ English translation of claims), 9 pgs.
"Japanese Application Serial No. 2013-521857, Response filed Jan. 25, 2016 to Notice of Reasons for Rejection dated Aug. 18, 2015", (W/ English Translation), 17 pgs.
"Japanese Application Serial No. 2013-544655, Office Action dated Mar. 8, 2016", (W/ English Translation), 8 pgs.
"Japanese Application Serial No. 2013-544655, Office Action dated Sep. 29, 2015", (W/ English Translation), 7 pgs.
"Japanese Application Serial No. 2013-544655, Response filed Jan. 4, 2016 to Office Action dated Sep. 29, 2015", (English Translation of Claims), 14 pgs.
"Japanese Application Serial No. 2013-544655, Response filed Jul. 14, 2016 to Office Action dated Mar. 8, 2016", (w/ English Translation of Claims), 13 pgs.
"Japanese Application Serial No. 2013-544858, Request for Examination filed Feb. 4, 2014", (With English Translation), 14 pgs.
"Japanese Application Serial No. 2014-121515, Notice of Reasons for Rejection dated Jan. 5, 2016", (W/ English Translation), 9 pgs.
"Japanese Application Serial No. 2014-121515, Office Action dated Jun. 2, 2015", (W/ English Translation), 10 pgs.
"Japanese Application Serial No. 2014-121515, Response filed May 11, 2016 to Notice of Reasons for Rejection dated Jan. 5, 2016", (W/ English Translation Of Claims), 11 pgs.
"Japanese Application Serial No. 2014-121515, Response filed Aug. 20, 2015 to Office Action dated Jun. 2, 2015", (W/ English Translation Of Claims), 6 pgs.
"Japanese Application Serial No. 2014-542297, Office Action dated May 31, 2016", (W/ English Translation Of Claims), 6 pgs.
"Japanese Application Serial No. 2014-542297, Office Action dated Jun. 30, 2015", (W/ English Translation), 10 pgs.
"Japanese Application Serial No. 2014-542297, Office Action dated Nov. 24, 2015", (W/ English Translation), 10 pgs.
"Japanese Application Serial No. 2014-542297, Response filed Feb. 23, 2016 to Office Action dated Nov. 24, 2015", (W/ English Translation Of Claims), 15 pgs.
"Japanese Application Serial No. 2014-542297, Response filed Jun. 8, 2016 to Office Action dated May 31, 2016", (W/ English Translation Of Claims), 14 pgs.

"Japanese Application Serial No. 2014-542297, Response filed Sep. 28, 2015 to Office Action dated Jun. 30, 2015", (W/ English Translation Of Claims), 16 pgs.
"Japanese Application Serial No. 2014-542301, Office Action dated May 12, 2015", (W/ English Translation), 6 pgs.
"Japanese Application Serial No. 2014-542301, Response filed Aug. 10, 2015 to Office Action dated May 12, 2015", (W/ English translation of claims), 21 pgs.
"Japanese Application Serial No. 2014-554709, Office Action dated Jul. 5, 2016", (W/ English Translation), 6 pgs.
"Japanese Application Serial No. 2014-554709, Preliminary Amendment filed Jul. 29, 2015", (W/ English translation of claims), 8 pgs.
"Japanese Application Serial No. 2014-554709, Response filed Dec. 19, 2016 to Office Action dated Jul. 5, 2016", (W/ English Translation of Claims), 11 pgs.
"Japanese Application Serial No. 2015-162707, Office Action dated Nov. 29, 2016", (W/ English Translation), 3 pgs.
"Japanese Application Serial No. 2015-162707, Response filed Jan. 26, 2017 to Office Action dated Nov. 27, 2016", (W/ English Translation), 16 pgs.
"Japanese Application Serial No. 2015-199496, Office Action dated Sep. 6, 2016", (W/ English Translation), 5 pgs.
"Japanese Application Serial No. 2015-199496, Response filed Dec. 5, 2016 to Office Action dated Sep. 6, 2016", (W/ English Translation of Claims), 9 pgs.
"Japanese Application Serial No. 2015-503563, Office Action dated Dec. 20, 2016", (W/ English Translation), 10 pgs.
"Japanese Application Serial No. 2015-503563, Response Filed Mar. 13, 2017 to Office Action dated Dec. 20, 2016", (W/ English Translation), 9 pgs.
"Japanese Application Serial No. 2016-145390, Office Action dated Apr. 25, 2017", (W/ English Translation), 5 pgs.
"Japanese Application Serial No. 2016-145390, Response filed Jul. 3, 2017 to Office Action dated Apr. 25, 2017", (W/ English Translation of Claims), 16 pgs.
"Japanese Application Serial No. 2017-161246, Office Action dated May 15, 2018", (W/ English Translation), 6 pgs.
"Legacy Implant Options", Nexgen Complete Knee Solution, (2002), 8 pgs.
"LPS-Flex Fixed Bearing Knee: Surgical Technique", Zimmer, Inc., (2004, 2007, 2008), 16 pgs.
"Mexican Application Serial No. MX/a/2013/000988, Office Action dated Mar. 18, 2015", w/English Claims, 17 pgs.
"Mexican Application Serial No. MX/a/2013/000988, Response filed Jun. 1, 2015 to Office Action dated Mar. 18, 2015", (W/English Translation), 12 pgs.
"Mexican Application Serial No. MX/A/2013/000988. Office Action dated Jun. 5, 2015", w/summary in English, 6 pgs.
"Mexican Application Serial No. MX/A/2013/000990, Final Office Action dated Feb. 4, 2016", w/ summary in English, 4 pgs.
"Mexican Application Serial No. MX/A/2013/000990, Office Action dated Feb. 19, 2015", (W/English Translation), 4 pgs.
"Mexican Application Serial No. MX/A/2013/000990, Response filed Apr. 29, 2015 to Office Action dated Feb. 19, 2015", W/ English Claims, 18 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.
"Natural-Knee II Primary System Surgical Technique", Zimmer, Inc., (2005), 48 pgs.
"Nexgen Complete Knee Solution", Extramedullary/Intramedullary Tibial Resector: Surgical Technique, Zimmer, Inc. 97-5997-002-00 Rev. 2, (2000, 2008, 2009), 28 pgs.
"Nexgen Complete Knee Solution", Extramedullary/Intramedullary Tibial Resector: Surgical Technique, Zimmer, Inc. 97-5997-02 Rev 1, (2000), 26 pgs.
"Nexgen Complete Knee Solution for the Legacy Knee LPS-Flex Fixed Bearing Knee", Zimmer Surgical Technique, 97-5964-102-00, (2004, 2007), 12 pgs.

(56) References Cited

OTHER PUBLICATIONS

"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"NexGen Trabecular Metal Modular Plates", Zimmer Inc., (2007), 19 pgs.
"Persona "Medial Congruent Articular Surface" System Overview", Zimmer, Inc., (2015), 6 pgs.
"Persona "The Personalized Knee System"", Medial Congruent Sales Training, Zimmer, Inc., (Jul. 2015), 53 pgs.
"Persona "The Personalized Knee System" Medial Congruent Advanced Bearings", Zimmer, Inc., (2015), 2 pgs.
"Persona "The Personalized Knee System" Medial Congruent Articular Surface Design Rationale", Zimmer, Inc., (2015), 20 pgs.
"Persona "The Personalized Knee System" Persona Medial Congruent", Mar. 24-28, 2015 at the American Academy of Orthopaedic Surgeons (AAOS) Annual Meeting., (Mar. 2015), 1 pg.
"Persona "The Personalized Knee System" Surgical Technique", Zimmer, Inc., (2015), 72 pgs.
"Persona Medial Congruent Articular Surface", Sales Training, Zimmer Biomet, (Jan. 2016), 71 pgs.
"PFC Sigma Knee System with Rotating Platform Technical/ Monograph", Depuy PFC Sigma RP, 0611-29-050 (Rev. 3), (1999), 70 pgs.
"Primary/Revision Surgical Technique for NexGen Rotating Hinge Knee (RHK)", Zimmer, Inc. Nexgen Complete Knee Solution, 97-5880-02, (2002), 116 pgs.
"Revision Instrumentation Surgical Technique for Legacy Knee Constrained Condylar Knee", Zimmer, Inc. Nexgen Complete Knee Solution, 97-5994-202, (2001), 61 pgs.
"Russian Application Serial No. 2013106942, Office Action dated Apr. 16, 2015", W/ English Translation, 5 pgs.
"Russian Application Serial No. 2013106942, Response filed Jul. 15, 2015 Office Action dated Apr. 16, 2015", (W/ English translation of claims), 146 pgs.
"Russian Application Serial No. 2013106943, Office Action dated Jul. 1, 2015", (W/ English Translation), 6 pgs.
"Russian Application Serial No. 2013106943, Office Action dated Dec. 28, 2015", w/ partial English Translation, 6 pgs.
"Russian Application Serial No. 2013106943, Response filed Apr. 28, 2016 to Office Action dated Dec. 28, 2015", (W/ English translation of claims), 19 pgs.
"Russian Application Serial No. 2013106943, Response filed Oct. 30, 2015 to Office Action dated Jul. 1, 2015", (W/ English translation of claims), 21 pgs.
"South African Application Serial No. 2013/01327, Amendment filed Apr. 24, 2014", W/ English Translation, 4 pgs.
"South African Application Serial No. 2013/01328, Amendment filed Apr. 24, 2014", W/ English Translation, 4 pgs.
"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.
"Surgical Technique for the CR-Flex Fixed Bearing Knee", NexGen Complete Knee Solution, Zimmer, Inc., (2003), 22 pgs.
"Surgical Technique for the Legacy Knee LPS-Flex Fixed Bearing Knee", Zimmer, Inc. Nexgen Complete Knee Solution, 97-5964-02, Rev. 1, (2000, 2002), 15 pgs.
"Surgical Technique for the Legacy Posterior Stabilized Knees", Zimmer, Inc. Nexgen Complete Knee Solution, 97-5996-02, (2002), 43 pgs.
"Surgical Technique—Nexgen Complete Knee Solution for the Legacy Knee LPS—Flex Fixed Bearing Knee", Zimmer, Inc., (2004, 2007), 12 pgs.
"The Zimmer Institute Surgical Technique MIS Quad-Sparing Surgical Technique for Total Knee Arthroplasty", NExGen Complete Knee Solution, (2004), 55 pgs.
"Tibial Baseplate: Pocket Guide (United States Version)", Zimmer, Inc.,, (2009), 17 pgs.
"Trabecular Metal Monoblock Tibial Components", Zimmer, Inc., (2007), 4 pgs.
"Trabecular Metal Monoblock Tibial Components Surgical Technique Addendum", Nexgen Zimmer, Inc., (2005, 2007), 12 pgs.
"Trabecular Metal Tibial Tray: Surgical Technique", NexGen Zimmer, Inc., (2007, 2009), 16 pgs.
"Zimmer MIS Intramedullary Instrumentation Surgical Technique For NexGen Cruciate Retaining & NexGen Legacy Posterior Stabilized Knees", printed 2005, 2009, Zimmer, Inc., (2009), 45 pgs.
"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.
"Zimmer NexGen CR-Flex and LPS-Flex Knees Surgical Technique with posterior Referencing Instrumentation.", Zimmer Inc., (2010, 2011), 48 pgs.
"Zimmer NexGen LCCK Surgical Technique for use with LCCK 4-in-1 Instrumentation", Zimmer, Inc.; copyright 2009, 2010, 2011, (May 2011), 52 pgs.
"Zimmer NexGen MIS Modular Tibial Plate and Keel Cemented Surgical Technique", Zimmer Inc., (2006, 2011), 26 pgs.
"Zimmer NexGen MIS Tibial Component", Brochure-97-5950-001-00 7.5mm, (2005, 2006), 8 pgs.
"Zimmer NexGen MIS Tibial Component Cemented Surgical Technique", Zimmer, Inc, #97-5950-002-00 Rev.1 1.5ML, (2005), 14 pgs.
"Zimmer NexGen MIS Tibial Component Cemented Surgical Technique", Zimmer Inc., (2005, 2006, 2008, 2009, 2010), 16 pgs.
"Zimmer NexGen Trabecular Metal Augments—Abbreviated Surgical Technique", Zimmer, Inc., (2004, 2006), 6 pgs.
"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.
"Zimmer NexGen Trabecular Metal Primary Patella Surgical Technique", Zimmer. Inc., 97-7255-112-00, (2005), 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
Annayappa, Ramesh, "Tibial Prosthesis", U.S. Appl. No. 13/189,328, filed Jul. 22, 2011, 82 pgs.
Annayappa, Ramesh, et al., "Tibial Prosthesis", U.S. Appl. No. 13/189,324, filed Jul. 22, 2011, 50 pgs.
Ding, M., et al., "Age-related variations in the microstructure of human tibial cancellous bone", Journal of Orthopaedic Research, 20(3), (2002), 615-621.
Ding, M., et al., "Changes in the three-dimensional microstructure of human tibial cancellous bone in early osteoarthritis", Journal of Bone & Joint Surgery (British), 85-B(6), (Aug. 2003), 906-912.
Doyle, et al., "Comparative Analysis of Human Trabecular Bone and Polyurethane Foam", Purdue University., 1 pg.
Dunbar, M. J., et al., "Fixation of a Trabecular Metal Knee Arthroplasty Component: A Prospective Randomized Study", The Journal of Bone & Joint Surgery (American), vol. 91—A(7), (Jul. 2009), 1578-1586.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Freeman, M.A.R., et al., "The Movement of the Knee Studied by Magnetic Resonance Imaging", Advanced Bearings—Clinical Orthopedics & Related Research 2003, (2003), 1 pg.
Hofmann, Aaron A, et al., "Posterior Stabilization in Total Knee Arthroplasty with Use of an Ultracongruent Polyethylene", The Journal of Arthroplasty vol. 15, No. 5, (2000), 576-583.
Hvid, Ivan, et al., "Trabecular bone Strength Patterns at the Proximal Tibial Epiphysis", Journal of Orthopaedic Research, vol. 3, No. 4, (1985), 464-472.

(56) References Cited

OTHER PUBLICATIONS

Klostermann, et al., "Distribution of bone mineral density with age and gender in the proximal tibia", Clinical Biomechanics 19, 376-376.
Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.
Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.
Parisi, Raymond C, "Motion Facilitating Tibial Components for a Knee Prosthesis", U.S. Appl. No. 13/229,103, filed Sep. 9, 2011, 46 pgs.
Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.
Siggelkow, Eik, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.
Siggelkow, Eik, et al., "Impact of Tibia Bearing Surface Design on Deep Knee Bend Kinematics", Mar. 24-28, 2015 at the AAOS Conference (Poster #P142), (Mar. 2015), 1 pg.
Stilling, et al., "Superior fixation of pegged trabecular metal over screw-fixed pegged porous titanium fiber mesh", Acta Orthopaedica., (2011), 177-186.
Wentorf, Mary S. S, "Asymmetric Tibial Components for a Knee Prosthesis", U.S. Appl. No. 13/189,338, filed Jul. 22, 2011, 58 pgs.
Wentorf, Mary S. S, "Asymmetric Tibial Components for a Knee Prosthesis", U.S. Appl. No. 13/189,339, filed Jul. 22, 2011, 52 pgs.
Wentorf, Mary S. S, "Asymmetric Tibial Components for a Knee Prosthesis", U.S. Appl. No. 13/189,336, filed Jul. 22, 2011, 60 pgs.
"U.S. Appl. No. 15/915,886, PTO Response to Rule 312 Communication dated May 8, 2020", 2 pgs.
"U.S. Appl. No. 15/971,743, Notice of Allowance dated Aug. 6, 2019", 8 pgs.
"U.S. Appl. No. 16/389,381, Non Final Office Action dated Mar. 30, 2020", 9 pgs.
"U.S. Appl. No. 16/675,938, Preliminary Amendment filed Jan. 22, 2020", 7 pgs.
"U.S. Appl. No. 16/715,092, Preliminary Amendment filed Mar. 19, 2020", 10 pgs.
"U.S. Appl. No. 16/743,746, Preliminary Amendment filed Mar. 19, 2020", 8 pgs.
"Australian Application Serial No. 2018266322, First Examination Report dated Dec. 19, 2019", 2 pgs.
"European Application Serial No. 18711801.3, Response to Communication pursuant to Rules 161(1) and 162 EPC filed May 7, 2020", 14 pgs.
"European Application Serial No. 19171990.5, Response filed May 13, 2020 to Extended European Search Report dated Oct. 16, 2019", 31 pgs.
"International Application Serial No. PCT/US201 8/031177, International Preliminary Report on Patentability dated Nov. 21, 2019", 8 pgs.
"International Application Serial No. PCT/US2018/031177, International Search Report dated Jul. 31, 2018", 6 pgs.
"International Application Serial No. PCT/US2018/031177, Written Opinion dated Jul. 31, 2018", 6 pgs.
"U.S. Appl. No. 15/915,886, Response filed Nov. 4, 2019 to Non-Final Office Action dated Aug. 2, 2019", 8 pgs.
"Brazil Application Serial No. BR1120130016698, Office Action dated Aug. 27, 2019", 8 pgs.
"Brazil Application Serial No. BR1120130016736, Office Action dated Aug. 27, 2019", 8 pgs.

"European Application Serial No. 16770657.1, Response filed Sep. 30, 2019 to Communication Pursuant to Article 94(3) EPC dated May 20, 2019", 26 pgs.
"European Application Serial No. 18206326.3, Extended European Search Report dated Apr. 15, 2019", 10 pgs.
"European Application Serial No. 19171990.5, Extended European Search Report dated Oct. 16, 2019", 8 pgs.
"Journey II XR, Bi-Cruciate Retaining Knee System", Smith & Nephew, Surgical Technique, (2015), 40 pgs.
"Vanguard® ID Total Knee, Surgical Technique", Zimmer Biomet; 0682.1-GLBL-en-REV0317, (2017), 36 pgs.
Bellemans, Johan, et al., "Is Neutral Mechanical Alignment Normal for All Patients?", Clinical Orthopaedics and Related Research; DOI 10.1007/s11999-011-1936-5, (Jun. 9, 2011), 9 pgs.
Hutt, Jonathan, et al.,, "Functional joint line obliquity after kinematic total knee arthroplasty", International Orthopaedics; DOI 10.1007/s00264-015-2733-7, (Mar. 21, 2015), 6 pgs.
Victor, Jan M. K., et al., "Constitutional Varus Does Not Affect Joint Line Orientation in the Coronal Plane", Joint Line Orientation in the Coronal Plane; 472; DOI 10.1007/s11999-013-2898-6, (Jun. 4, 2013), pp. 98-104.
"U.S. Appl. No. 14/471,440, Notice of Allowance dated Nov. 13, 2017", 9 pgs.
"U.S. Appl. No. 14/471,440, Response filed Aug. 16, 2017 to Restriction Requirement dated Jun. 30, 2017", 8 pgs.
"U.S. Appl. No. 14/471,440, Restriction Requirement dated Jun. 30, 2017", 6 pgs.
"U.S. Appl. No. 15/890,735, Notice of Allowance dated Oct. 29, 2019", 11 pgs.
"U.S. Appl. No. 15/915,886, Notice of Allowance dated Jan. 16, 2020", 9 pgs.
"Brazil Application Serial No. BR1120130016698, Response filed Dec. 9, 2019 to Office Action dated Aug. 27, 2019", w/ English Claims, 22 pgs.
"Brazil Application Serial No. BR1120130016736, Response filed Dec. 9, 2019 to Office Action dated Aug. 27, 2019", w/ English Claims, 25 pgs.
"European Application Serial No. 18206326.3, Response filed Nov. 22, 2019 to Extended European Search Report dated Apr. 15, 2019", 15 pgs.
"Indian Application Serial No. 1544/DELNP/2013, Response filed Nov. 18, 2019 to Office Action dated May 21, 2019", w/ English claims, 34 pgs.
"Indian Application Serial No. 1545/DELNP/2013, Office Action dated Dec. 9, 2019", (with English translation), 8 pages.
"Turkish Application Serial No. 11808493.8, Working Requirements dated Feb. 17, 2020", 3 pgs.
"U.S. Appl. No. 16/179,201, Examiner Interview Summary dated Feb. 8, 2021", 3 pgs.
"U.S. Appl. No. 16/179,201, Non Final Office Action dated Nov. 2, 2020", 15 pgs.
"U.S. Appl. No. 16/179,201, Response filed Jan. 28, 2021 to Non Final Office Action dated Nov. 2, 2020", 16 pgs.
"U.S. Appl. No. 16/179,201, Response filed Oct. 5, 2020 to Restriction Requirement dated Aug. 7, 2020", 9 pgs.
"U.S. Appl. No. 16/179,201, Restriction Requirement dated Aug. 7, 2020", 10 pgs.
"U.S. Appl. No. 16/179,201, Supplemental Amendment & Response filed Feb. 19, 2021 to Non-Final Office Action Filed Nov. 2, 2020", 17 pgs.
"U.S. Appl. No. 16/352,287, Non Final Office Action dated Dec. 10, 2020", 12 pgs.
"U.S. Appl. No. 16/352,287, Response filed Feb. 22, 2021 to Non Final Office Action dated Dec. 10, 2020", 14 pgs.
"U.S. Appl. No. 16/352,287, Response filed Oct. 12, 2020 to Restriction Requirement dated Aug. 17, 2020", 8 pgs.
"U.S. Appl. No. 16/352,287, Restriction Requirement dated Aug. 17, 2020", 6 pgs.
"U.S. Appl. No. 16/389,381, Notice of Allowance dated Jul. 16, 2020", 5 pgs.
"U.S. Appl. No. 16/389,381, Response filed Jun. 19, 2020 to Non Final Office Action dated Mar. 30, 2020", 9 pgs.

(56) References Cited

OTHER PUBLICATIONS

"U.S. Appl. No. 16/849,394, Preliminary Amendment filed Jun. 3, 2020", 7 pgs.
"U.S. Appl. No. 17/068,435, Preliminary Amendment filed Nov. 13, 2020", 7 pgs.
"Brazilian Application Serial No. BR1120130016736, Response filed Oct. 5, 2020 to Office Action dated Jun. 10, 2020", (W/ English Translation of Claims), 91 pages.
"Canadian Application Serial No. 3,063,415, Office Action dated Jul. 13, 2020", 3 pgs.
"Canadian Application Serial No. 3,063,415, Response filed Nov. 12, 2020 to Office Action dated Jul. 13, 2020", 15 pgs.
"Chinese Application Serial No. 201880016775.4, Office Action dated Jan. 22, 2021", (W/English Translation), 15 pgs.
"Chinese Application Serial No. 201880031319.7, Office Action dated May 15, 2020", (W/ English Translation), 12 pgs.
"Chinese Application Serial No. 201880031319.7, Office Action dated Nov. 18, 2020", with English translation, 9 pgs.
"Chinese Application Serial No. 201880031319.7, Response filed Jan. 18, 2021 to Office Action dated Nov. 18, 2020", with English claims, 16 pgs.
"Chinese Application Serial No. 201880031319.7, Response filed Jul. 22, 2020 to Office Action dated May 15, 2020", (W/ English Claims), 10 pgs.
"European Application Serial No. 18726670.5, Response to Communication pursuant to Rules 161(1) and 162 EPC filed Jul. 20, 2020", 9 pgs.
"Indian Application Serial No. 1545/DELNP/2013, Response filed Jun. 9, 2020 to Office Action dated Dec. 9, 2019", (W/ English Claims), 78 pgs.
"Japanese Application Serial No. 2019-562605, Notification of Reasons for Refusal dated Jun. 16, 2020", (W/ English Translation), 7 pgs.
"Japanese Application Serial No. 2019-562605, Notification of Reasons for Refusal dated Nov. 10, 2020", with English translation, 5 pgs.
"Japanese Application Serial No. 2019-562605, Response filed Feb. 9, 2021 to Notification of Reasons for Refusal dated Nov. 10, 2020", w/English claims, 19 pgs.
"Japanese Application Serial No. 2019-562605, Response filed Sep. 15, 2020 to Notification of Reasons for Refusal dated Jun. 16, 2020", (W/ English Claims), 15 pgs.
"U.S. Appl. No. 16/179,201, Advisory Action dated Jun. 25, 2021", 3 pgs.
"U.S. Appl. No. 16/179,201, Final Office Action dated Apr. 20, 2021", 11 pgs.
"U.S. Appl. No. 16/179,201, Response filed Jun. 18, 2021 to Final Office Action dated Apr. 20, 2021", 16 pgs.
"U.S. Appl. No. 16/352,287, Final Office Action dated May 25, 2021", 8 pgs.
"U.S. Appl. No. 16/352,287, Notice of Allowance dated Jun. 30, 2021", 7 pgs.
"U.S. Appl. No. 16/352,287, Response filed Jun. 18, 2021 to Final Office Action dated May 25, 2021", 8 pgs.
"U.S. Appl. No. 16/530,423, Non Final Office Action dated May 17, 2021", 10 pgs.
"U.S. Appl. No. 16/715,092, Response filed Aug. 11, 2021 to Non Final Office Action dated May 17, 2021", 15 pgs.
"U.S. Appl. No. 16/715,092, Response filed Aug. 9, 2021 to Restriction Requirement dated Jun. 25, 2021", 7 pgs.
"U.S. Appl. No. 16/715,092, Restriction Requirement dated Jun. 25, 2021", 6 pgs.
"Australian Application Serial No. 2020204019, First Examination Report dated Jun. 18, 2021", 7 pgs.
"Chinese Application Serial No. 201880016775.4, Decision of Rejection dated Jul. 12, 2021", (W/ English Translation), 13 pgs.
"European Application Serial No. 16189084.3, Communication Pursuant to Article 94(3) EPC dated Jul. 1, 2021", 6 pgs.

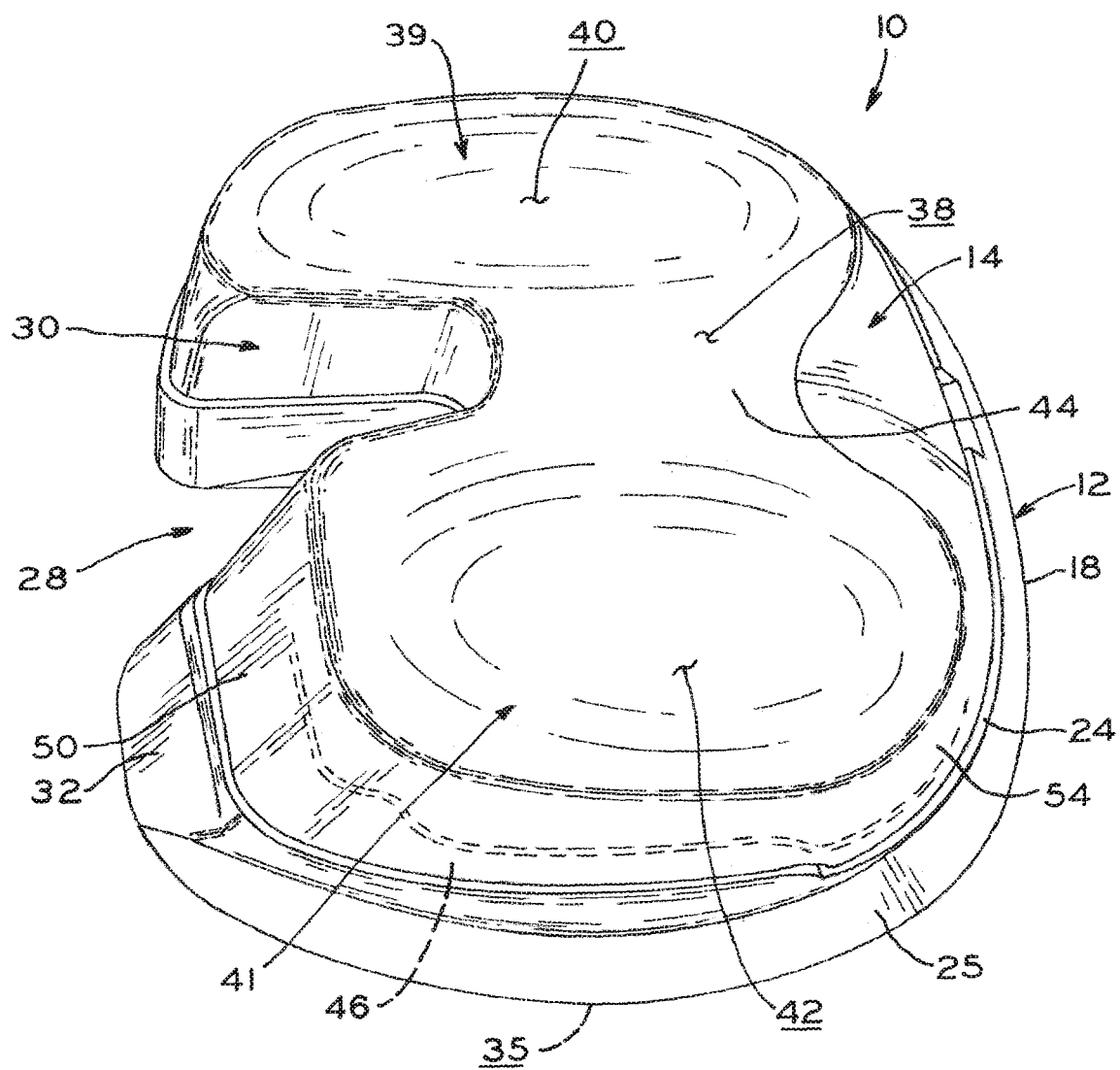
FIG_1B

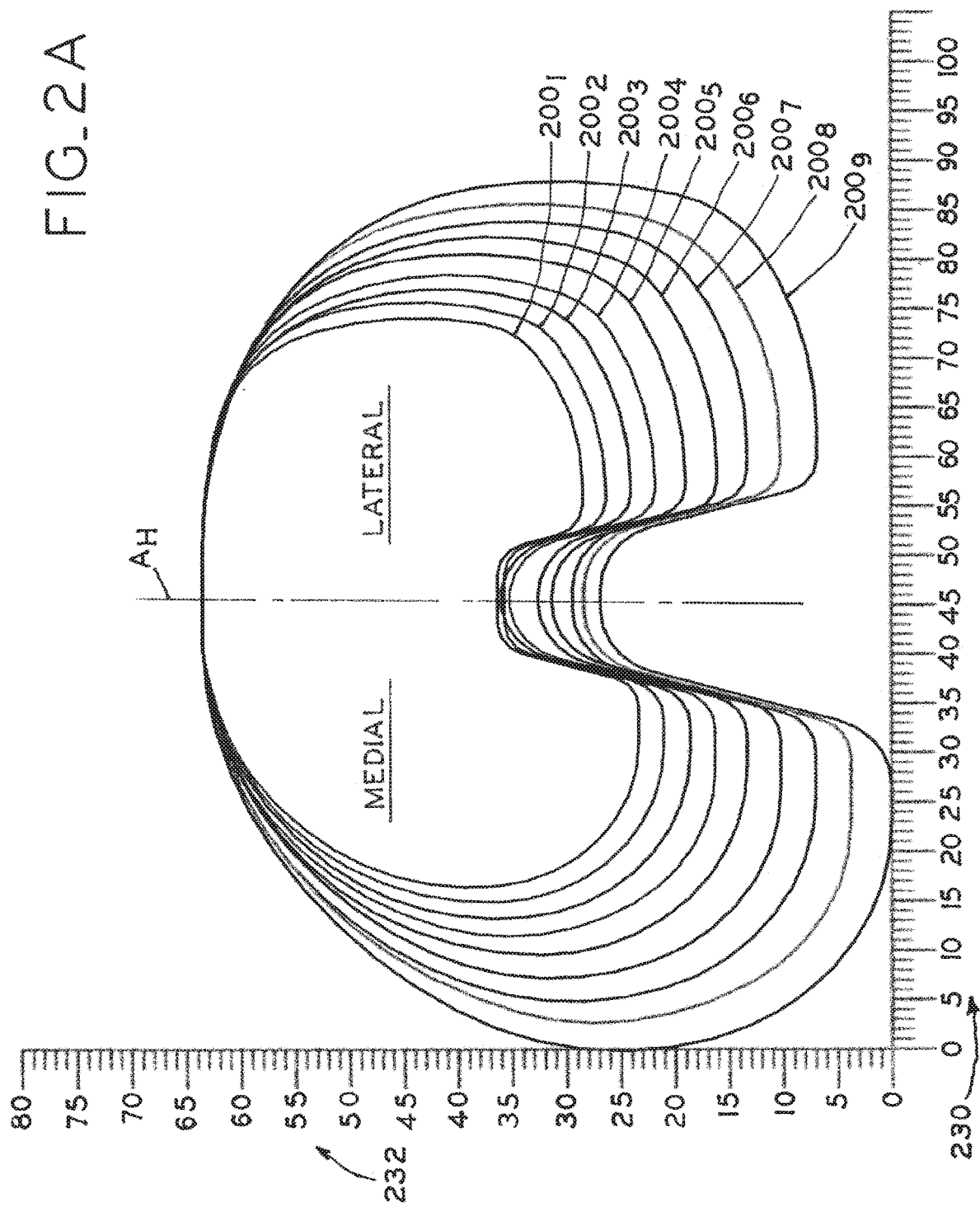

ASYMMETRIC TIBIAL COMPONENTS FOR A KNEE PROSTHESIS

CROSS-REFERENCE TO RELATED APPLICATIONS

This application is a continuation of U.S. patent application Ser. No. 15/827,654, filed on Nov. 30, 2017 and entitled ASYMMETRIC TIBIAL COMPONENTS FOR A KNEE PROSTHESIS, now issued as U.S. Pat. No. 10,470,889, which is a continuation of U.S. patent application Ser. No. 14/034,937, filed on Sep. 24, 2013 and entitled ASYMMETRIC TIBIAL COMPONENTS FOR A KNEE PROSTHESIS, now issued as U.S. Pat. No. 9,861,490, which is a continuation of U.S. patent application Ser. No. 13/189,336, filed on Jul. 22, 2011 and entitled ASYMMETRIC TIBIAL COMPONENTS FOR A KNEE PROSTHESIS, now issued as U.S. Pat. No. 8,613,775, which claims the benefit under Title 35, U.S.C. § 119(e) of U.S. Provisional Patent Application Ser. No. 61/381,800, filed on Sep. 10, 2010 and entitled TIBIAL PROSTHESIS FACILITATING ROTATIONAL ALIGNMENT, and U.S. Provisional Patent Application Ser. No. 61/367,375, filed on Jul. 24, 2010 and entitled TIBIAL PROSTHESIS, the entire disclosures of which are hereby expressly incorporated by reference herein.

BACKGROUND

1. Technical Field

The present disclosure relates to orthopaedic prostheses and, specifically, to tibial components in a knee prosthesis.

2. Description of the Related Art

Orthopaedic prostheses are commonly utilized to repair and/or replace damaged bone and tissue in the human body. For example, a knee prosthesis may include a tibial baseplate that is affixed to a resected or natural proximal tibia, a femoral component attached to a resected or natural distal femur, and a tibial bearing component coupled with the tibial baseplate and disposed between the tibial baseplate and femoral component. Knee prostheses frequently seek to provide articulation similar to a natural, anatomical articulation of a knee joint, including providing a wide range of flexion.

The tibial insert component, sometimes also referred to as a tibial bearing or meniscal component, is used to provide an appropriate level of friction and contact area at the interface between the femoral component and the tibial bearing component. For a knee prosthesis to provide a sufficient range of flexion with a desirable kinematic motion profile, the tibial bearing component and tibial baseplate must be sized and oriented to interact appropriately with the femoral component of the knee prosthesis throughout the flexion range. Substantial design efforts have been focused on providing a range of prosthesis component sizes and shapes to accommodate the natural variability in bone sizes and shapes in patients with orthopaedic prostheses, while preserving flexion range and desired kinematic motion profile.

In addition to facilitating implantation and providing enhanced kinematics through manipulation of the size and/or geometry of prosthesis components, protection and/or preservation of soft tissues in the natural knee joint is also desirable.

A given prosthetic component design (i.e., a tibial baseplate, tibial bearing component, or femoral component) may be provided to a surgeon as a kit including a variety of different sizes, so that the surgeon may choose an appropriate size intraoperatively and/or on the basis of pre-surgery planning. An individual component may be selected from the kit based upon the surgeon's assessment of fit and kinematics, i.e., how closely the component matches the natural contours of a patient's bone and how smoothly the assembled knee joint prosthesis functions in conjunction with adjacent soft tissues and other anatomical structures. Soft tissue considerations include proper ligament tension and minimization of soft tissue impingement upon prosthetic surfaces, for example.

In addition to prosthetic sizing, the orientation of a prosthetic component on a resected or natural surface of a bone also impacts surgical outcomes. For example, the rotational orientation of a tibial baseplate and tibial bearing component with respect to a resected proximal tibia will affect the interaction between the corresponding femoral prosthesis and the tibial bearing component. The nature and amount of the coverage of a tibial baseplate over specific areas of the resected proximal tibia will also affect the fixation of the implant to the bone. Thus, substantial design efforts have been focused on providing prosthetic components which are appropriately sized for a variety of patient bone sizes and are adapted to be implanted in a particular, proper orientation to achieve desired prosthesis performance characteristics.

SUMMARY

The present disclosure provides an orthopaedic tibial prosthesis including a tibial baseplate with an asymmetric periphery which promotes proper positioning and orientation on a resected tibia, while also facilitating enhanced kinematics, soft-tissue interaction, and long-term fixation of the complete knee prosthesis. The asymmetric baseplate periphery is sized and shaped to substantially match portions of the periphery of a typical resected proximal tibial surface, such that proper location and orientation is evident by resting the baseplate on the tibia. The baseplate periphery provides strategically positioned relief and/or clearance between the baseplate periphery and bone periphery, such as in the posterior-medial portion to prevent deep-flexion component impingement, and in the anterior-lateral portion to avoid undue interaction between the anatomic iliotibial band and prosthesis components.

In one form thereof, the present invention provides a tibial prosthesis comprising: a distal surface; a proximal surface generally opposite the distal surface, the proximal surface having a lateral compartment and a medial compartment; and a peripheral wall extending between the distal and the proximal surface, the peripheral wall defining: an anterior edge; a lateral posterior edge generally opposite the anterior edge and forming a posterior boundary of the lateral compartment; a medial posterior edge generally opposite the anterior edge and forming a posterior boundary of the medial compartment; a lateral periphery extending from the anterior edge to the lateral posterior edge, the lateral periphery defining a plurality of adjacent lateral arcs, an adjacent pair of the plurality of adjacent lateral arcs defining a first lateral radius and a second lateral radius, respectively, the first lateral radius larger than the second lateral radius by at least 100%, whereby the lateral periphery is relatively boxy; and a medial periphery extending from the anterior edge to the medial posterior edge, the medial periphery defining a plurality of adjacent medial arcs, an adjacent pair of the plurality of adjacent medial arcs defining a first medial radius and a second medial radius, respectively, the first medial radius larger than the second medial radius by less than 75%, whereby the medial periphery is generally rounded.

In another form thereof, the present invention provides a tibial prosthesis comprising: a distal surface; a proximal surface generally opposite the distal surface; and a peripheral wall extending between the distal and the proximal surface, the peripheral wall defining: an anterior edge; a lateral periphery including: a lateral edge defining a substantially perpendicular tangent with respect to the anterior edge, an anterior-lateral corner traversing an angular sweep between the anterior edge and the lateral edge to define a boxy corner periphery having an anterior-lateral corner edge length, and a posterior-lateral corner extending away from the lateral edge and the anterior-lateral corner; and a medial periphery including: a medial edge defining a substantially perpendicular tangent with respect to the anterior edge, an anterior-medial corner traversing an angular sweep between the anterior edge and the medial edge to define a rounded corner periphery having an anterior-medial corner edge length that is longer than the anterior-lateral corner edge length, in which the angular sweep between the anterior edge and the medial edge is similar to the angular sweep between the anterior edge and the lateral edge, and a posterior-medial corner extending away from the medial edge and the anterior-medial corner.

In yet another form thereof, the present invention provides a tibial prosthesis comprising an asymmetric prosthesis periphery, the periphery comprising: an anteroposterior axis dividing the prosthesis periphery into a medial compartment and a lateral compartment; an anterior edge disposed between the medial compartment and the lateral compartment; a lateral posterior edge generally opposite the anterior edge and forming a posterior boundary of the lateral compartment; a medial posterior edge generally opposite the anterior edge and forming a posterior boundary of the medial compartment; a lateral periphery extending from the anterior edge to the lateral posterior edge, the lateral periphery defining: an anterior-lateral arc having an anterior-lateral arc center; and a lateral arc having a lateral arc center, the lateral arc defining a tangent parallel to the anteroposterior axis; a medial periphery extending from the anterior edge to the medial posterior edge, the medial periphery defining: an anterior-medial arc having an anterior-medial arc center; and a medial arc having a medial arc center, the medial arc defining a tangent parallel to the anteroposterior axis, a mediolateral axis defining the longest line segment within the prosthesis periphery that is also perpendicular to the anteroposterior axis, the anterior-lateral arc center disposed between the mediolateral axis and the anterior edge, the anterior-medial arc center disposed posterior of the mediolateral axis.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1B is an assembled, perspective view of the tibial baseplate and tibial bearing component shown in FIG. 1A;

FIG. 2A is a top plan view of the peripheries of a set of nine tibial baseplates made in accordance with the present disclosure, in which the peripheries are shown to scale according to the illustrated scales in millimeters in the bottom and right-hand margins of the page;

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The present disclosure provides an asymmetric knee joint prosthesis which facilitates proper rotational and spatial orientation of a tibial baseplate and tibial bearing component upon a resected proximal tibia, while also offering large-area contact with the resected proximal tibia. The prosthesis permits a wide range of flexion motion, protects natural soft tissue proximate the knee joint prosthesis, and optimizes long term fixation characteristics of the prosthesis.

In order to prepare the tibia and femur for receipt of a knee joint prosthesis of the present disclosure, any suitable methods or apparatuses may be used. As used herein, "proximal" refers to a direction generally toward the torso of a patient, and "distal" refers to the opposite direction of proximal, i.e., away from the torso of the patient.

As used herein, the "periphery" of a tibial prosthesis refers to any periphery as viewed in a top plan view, e.g., in a generally transverse anatomical plane. Alternatively, the periphery of a tibial prosthesis may be any periphery as viewed in bottom plan view, e.g., in a generally transverse plane and looking at the distal surface adapted to contact a resected proximal surface of a tibial bone.

As used herein, the term "centroid" or "geometric center" refers to the intersection of all straight lines that divide a given area into two parts of equal moment about each respective line. Stated another way, a geometric center may be said to be the "average" (i.e., arithmetic mean) of all points of the given area. Stated yet another way, the geometric center is a point in a two dimensional figure from which the sum of the displacement vectors of all points on the figure equals zero.

As used herein, a "disparity" or "difference" between two numerical values (e.g., one value "larger" or "smaller" than another), typically expressed as a percentage, is the difference between the two values divided by the smaller of the two values. For example, a smaller quantity having value 75 and a larger quantity having value 150 would have a percentage disparity of (150−75)/75, or 100%.

Figure 5:
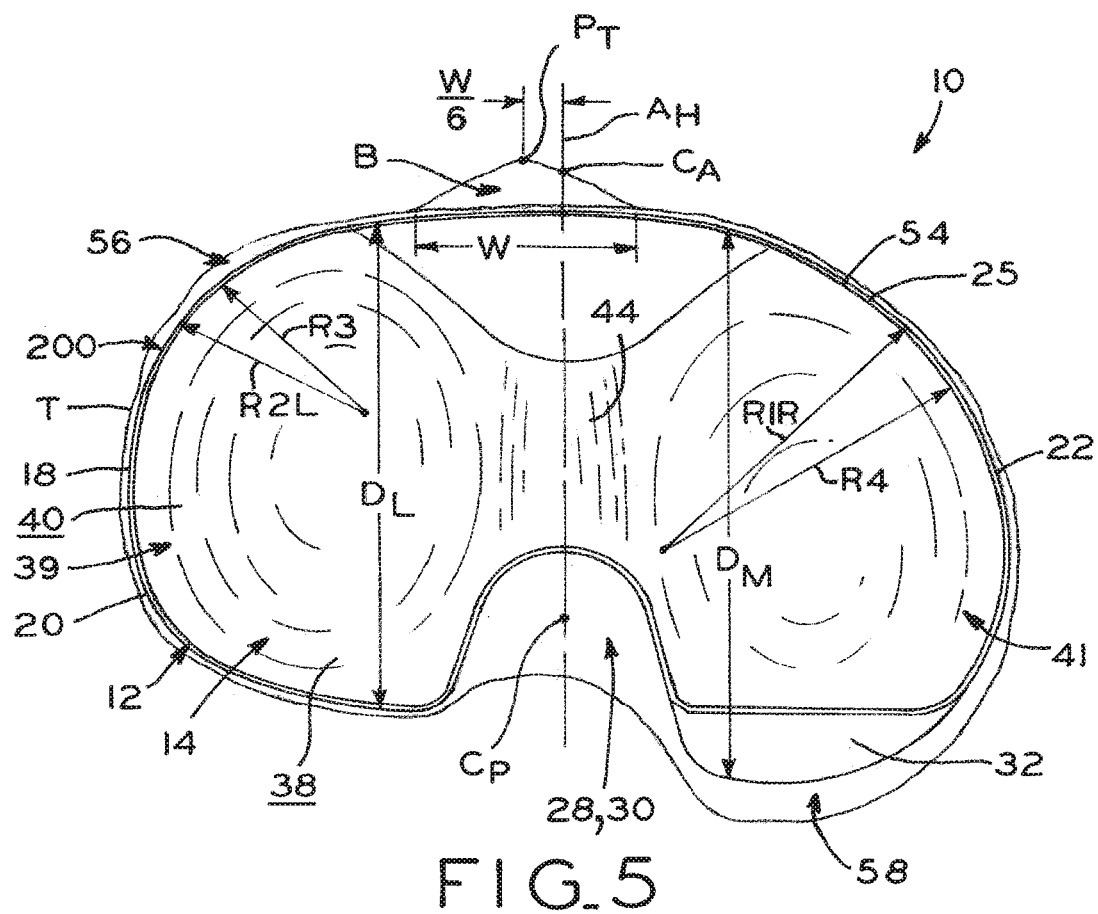
FIG. 5 is a top plan view of a resected proximal tibial surface with a prosthetic tibial baseplate component and tibial bearing component made in accordance with the present disclosure mounted thereon.

Referring to FIG. 5, tibia T includes tibial tubercle B having mediolateral width W, with tubercle midpoint $P_T$ located on tubercle B approximately halfway across width W. While tubercle B is shown as having midpoint $P_T$ at the "peak" or point of maximum anterior eminence, it is recognized that midpoint $P_T$ of tibia T may be spaced from such a peak. Tibia T also includes attachment point $C_P$ representing the geometric center of the attachment area between the anatomic posterior cruciate ligament (PCL) and tibia T. Recognizing that the PCL typically attaches to a tibia in two ligament "bundles," one of which is relatively anterior, lateral and proximal and the other of which relatively posterior, medial and distal, attachment point $C_P$ is contemplated as representing the anterior/lateral attachment area in an exemplary embodiment. However, it is contemplated that the posterior/medial attachment area, or the entire attachment area, could be used.

As used herein, "anterior" refers to a direction generally toward the front of a patient. "Posterior" refers to the opposite direction of anterior, i.e., toward the back of the patient.

In the context of patient anatomy, "home axis" $A_H$ refers to a generally anteroposterior axis extending from posterior point $C_P$ to an anterior point $C_A$, in which anterior point $C_A$ is disposed on tubercle B and medially spaced from tubercle midpoint $P_T$ by an amount equal to W/6. Stated another way, anterior point $C_A$ is laterally spaced by an amount equal to W/3 from the medial end of mediolateral width W, such that point $C_A$ lies on the "medial third" of the anterior tibial tubercle.

In the context of a prosthesis, such as tibial baseplate 12 described below, "home axis" $A_H$ refers to an axis oriented with respect to baseplate 12 such that the baseplate home axis $A_H$ of baseplate 12 is aligned with home axis $A_H$ of tibia T after implantation of baseplate 12 in a proper rotational and spatial orientation (as shown in FIG. 5). In the illustrative embodiments shown in FIG. 3 and described in detail below, home axis $A_H$ bisects PCL cutout 28 at the posterior edge of periphery 200 of tibial plateau 18 (FIG. 5), and bisects anterior edge 202 at the anterior edge of periphery 200 of tibial plateau 18. It is contemplated that home axis $A_H$ may be oriented to other baseplate features, it being understood that home axis $A_H$ of baseplate 12 is positioned such that that proper alignment and orientation of baseplate 12 upon tibia T positions the home axis $A_H$ of baseplate 12 coincident with home axis $A_H$ of tibia T.

Home axis $A_H$ of tibial baseplate 12 may be said to be an anteroposterior axis, as home axis $A_H$ extends generally anteriorly and posteriorly when baseplate 12 is implanted upon tibia T. Tibial baseplate also defines mediolateral axis $A_{ML}$, which lies along the longest line segment contained within periphery 200 that is also perpendicular to home axis $A_H$ of baseplate 12. As described below, home axis $A_H$ and mediolateral axis $A_{ML}$ cooperate to define a coordinate system useful for quantifying certain baseplate features in accordance with the present disclosure.

Figure 1A:
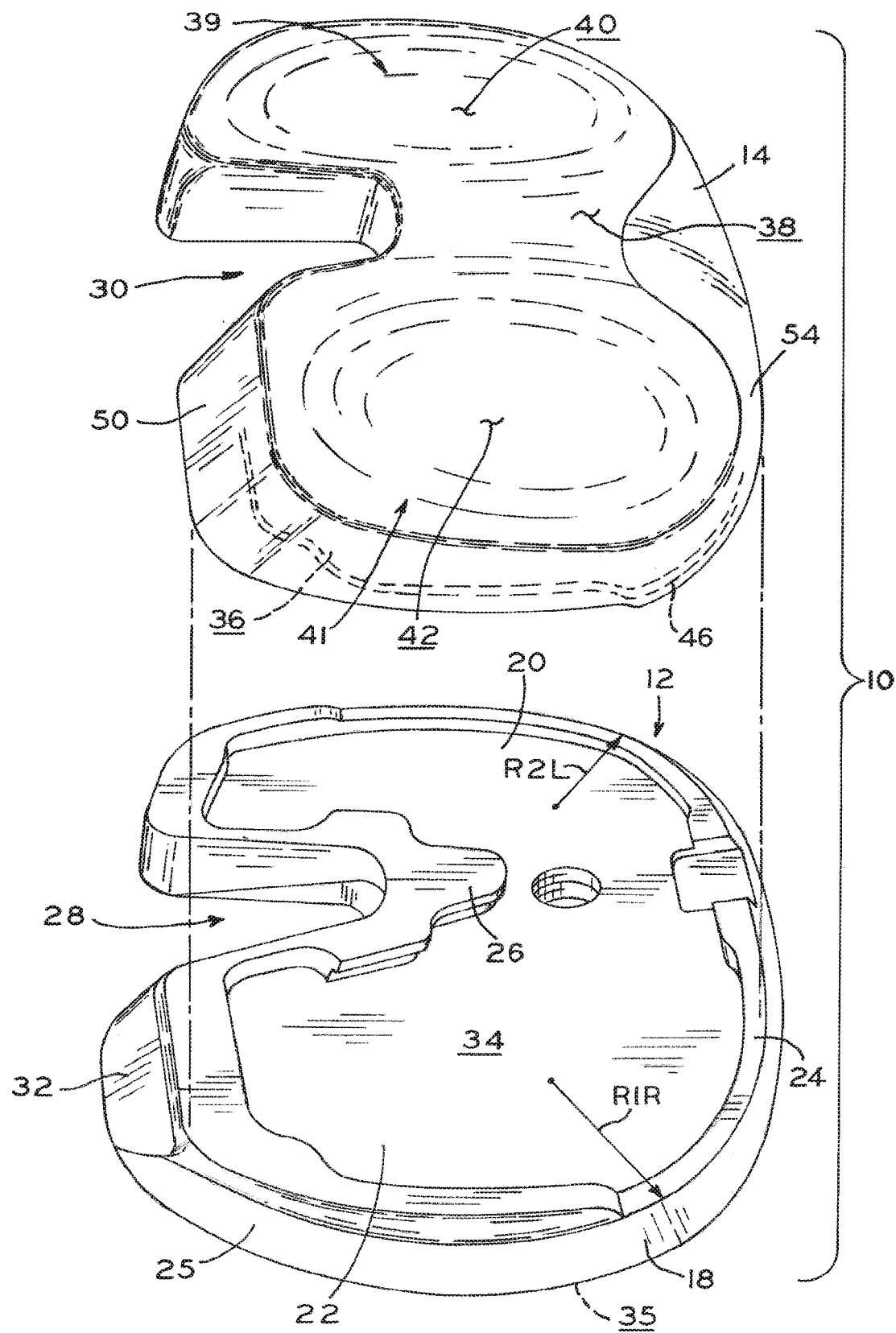
FIG. 1A is an exploded, perspective view of a tibial baseplate and tibial bearing component in accordance with the present disclosure.
Figure 2B:
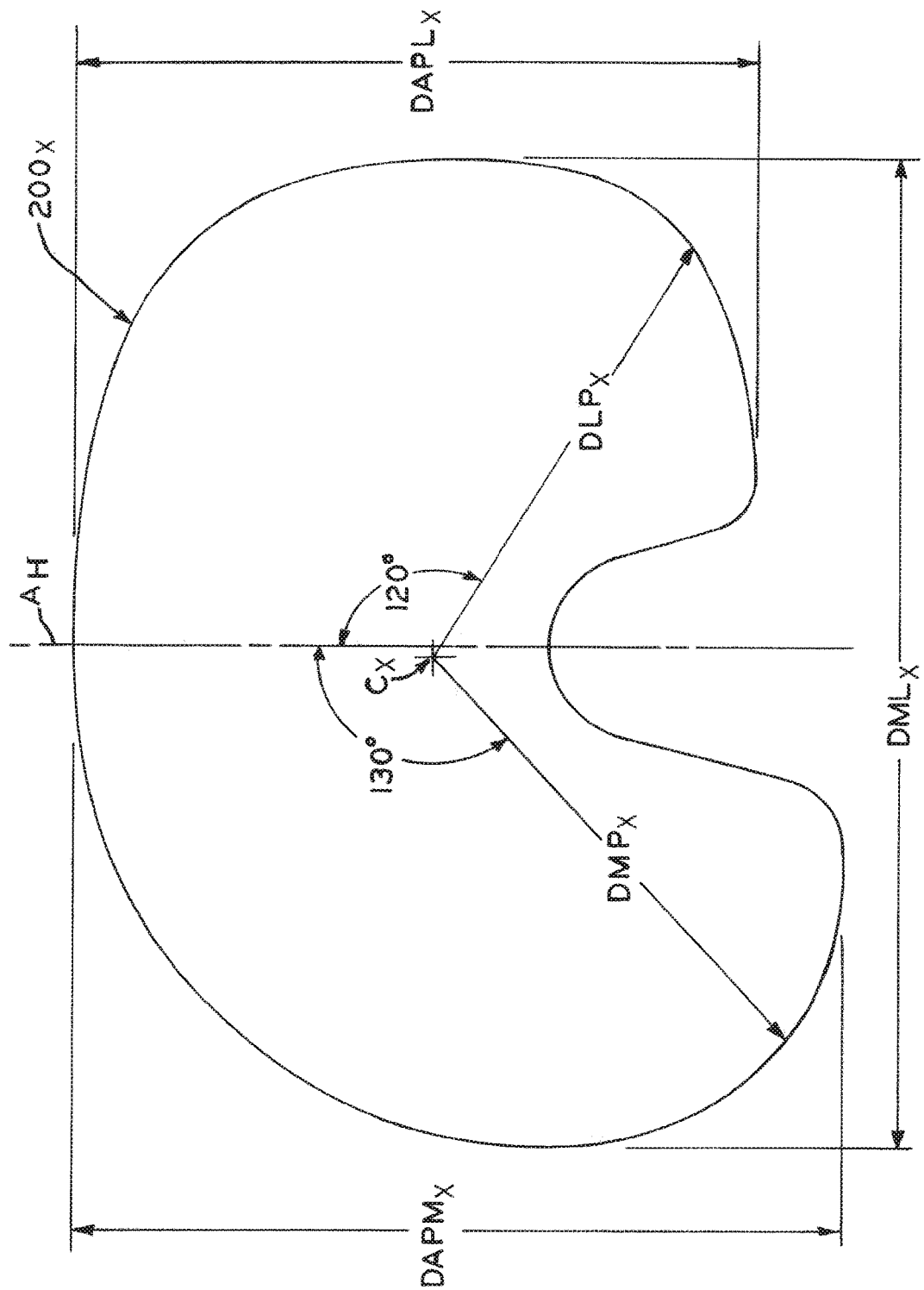
FIG. 2B is a top plan view of the periphery of a tibial baseplate made in accordance with the present disclosure.
Figure 3A:
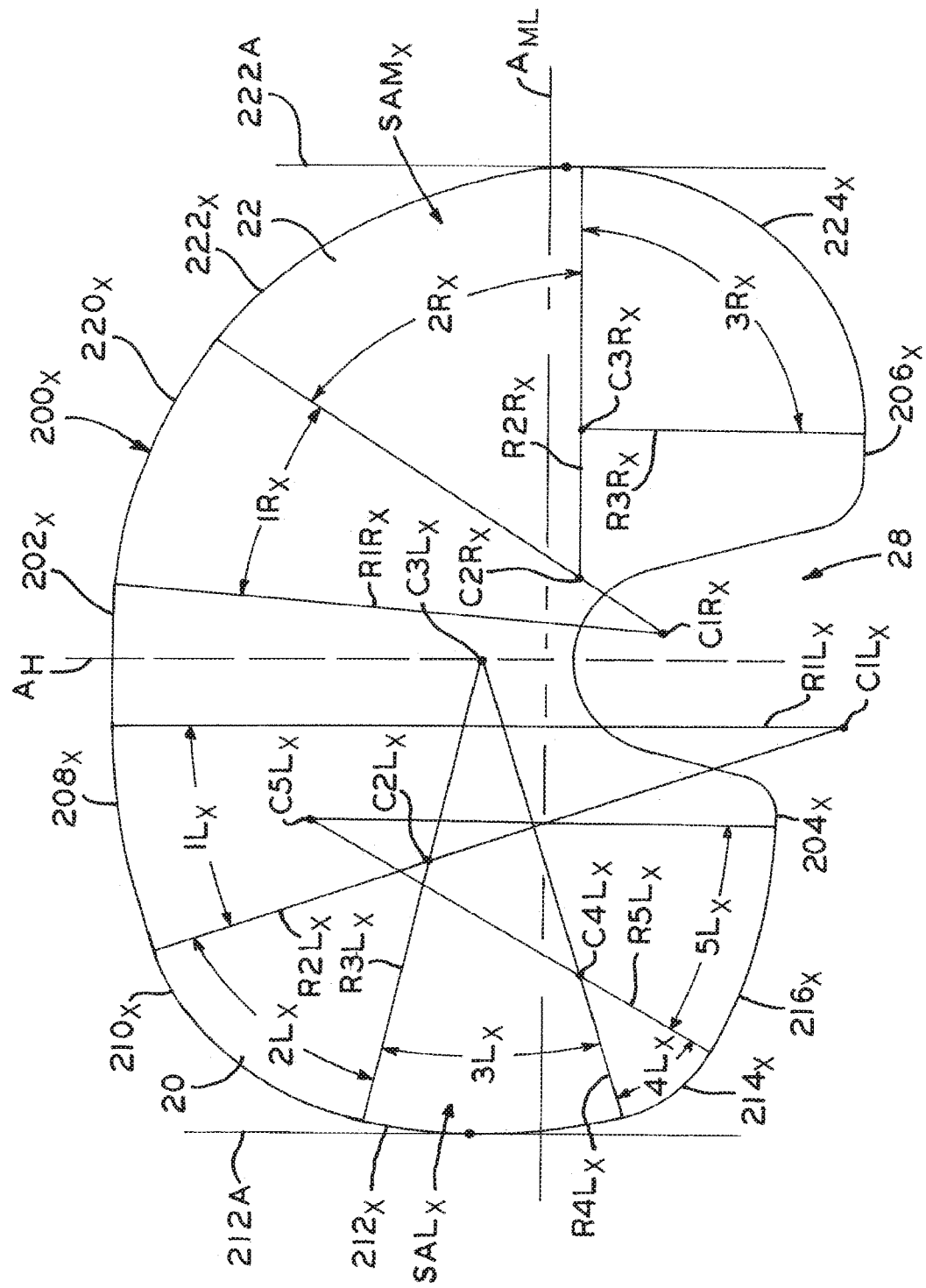
FIG. 3A is top plan view of a periphery of a tibial baseplate made in accordance with the present disclosure, illustrating various arcs defined by the periphery.
Figure 3B:
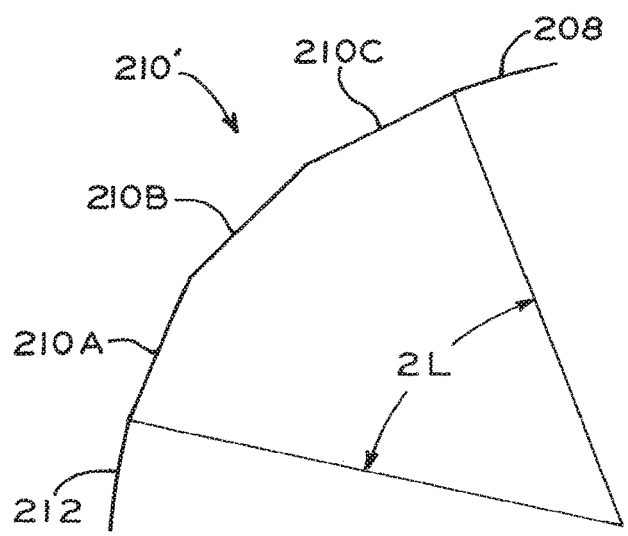
FIG. 3B is a partial, top plan view of the periphery shown in FIG. 3A, illustrating an alternative lateral corner periphery.
Figure 3C:
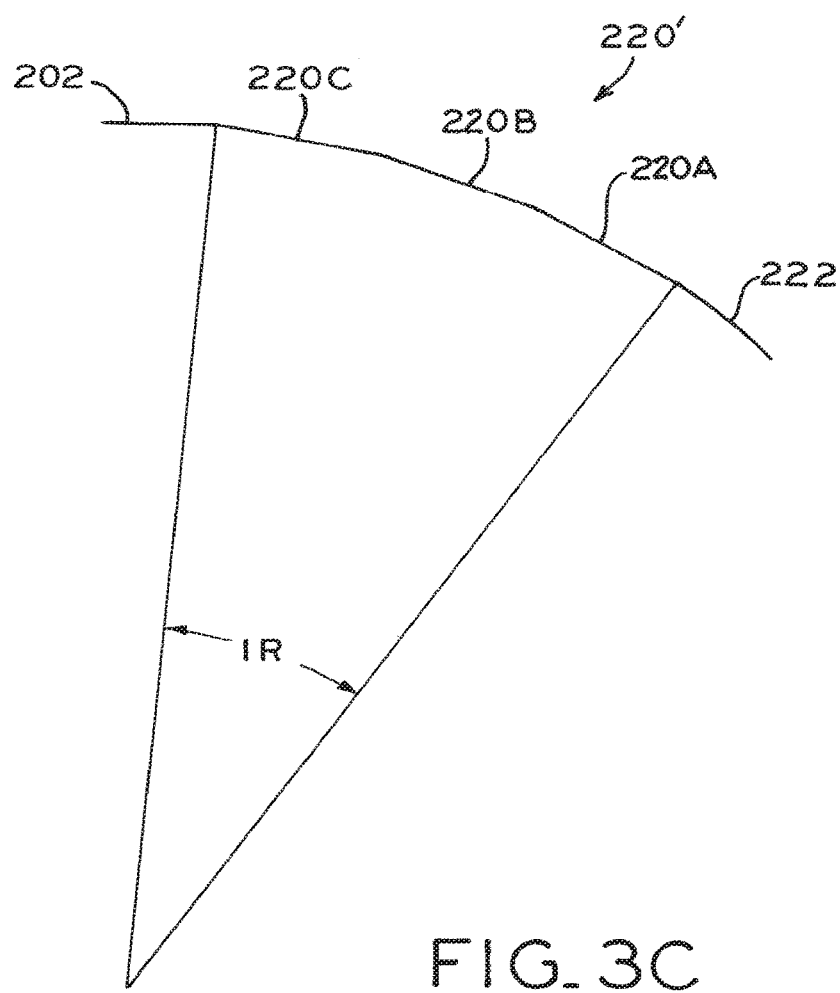
FIG. 3C is a partial, top plan view of the periphery shown in FIG. 3A, illustrating an alternative medial corner periphery.
Figure 3D:
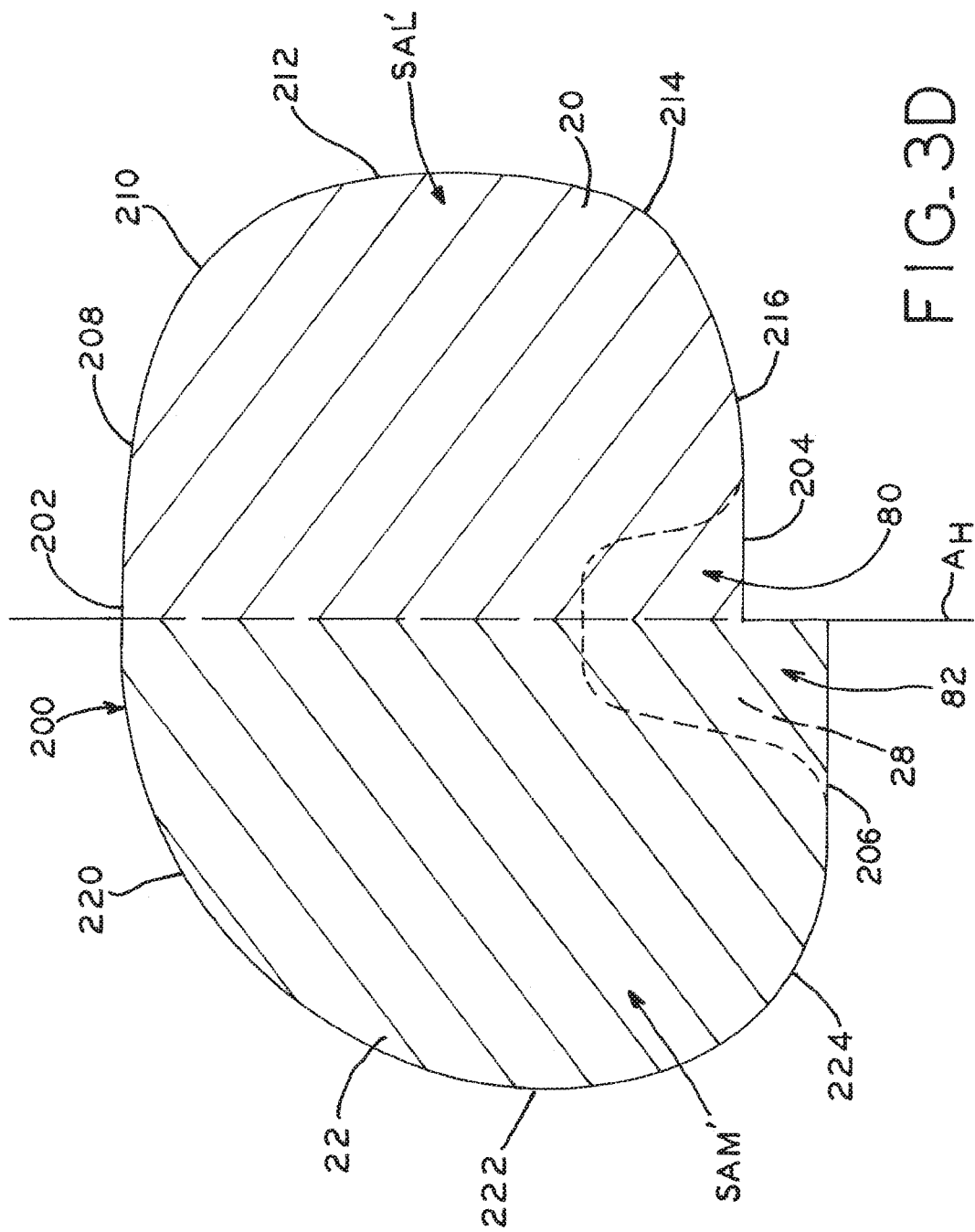
FIG. 3D is a top plan view of the periphery of a tibial baseplate made in accordance with the present disclosure, illustrating medial and lateral surface area calculations without a PCL cutout.
Figure 4A:
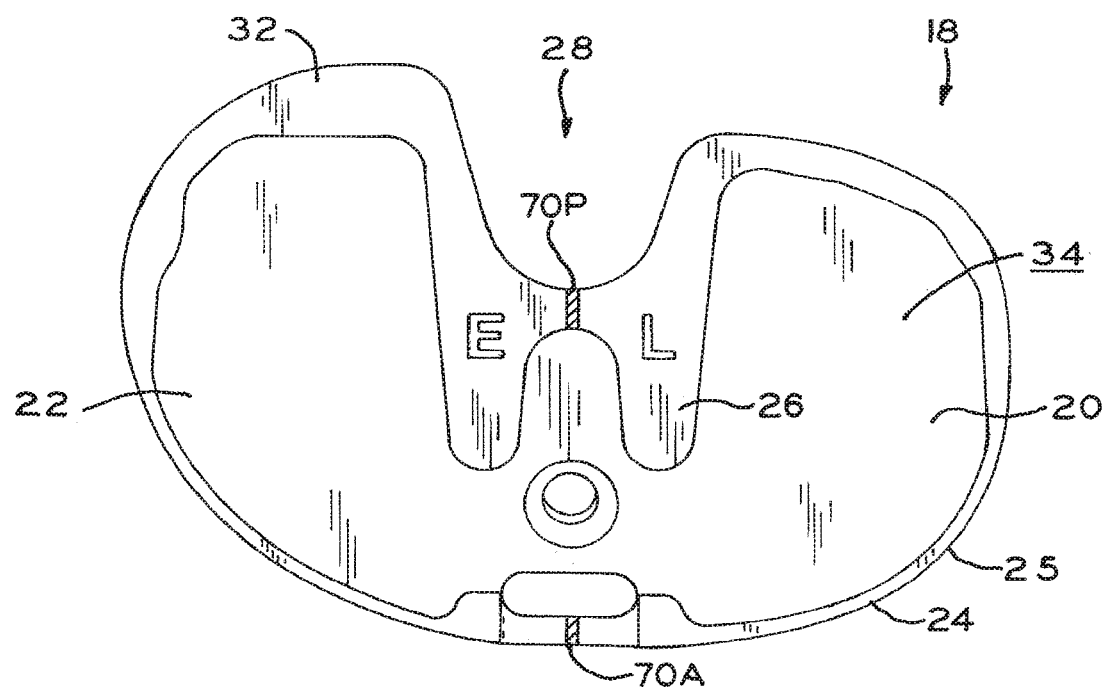
FIG. 4A is a top plan view of a tibial baseplate made in accordance with the present disclosure.
Figure 4B:
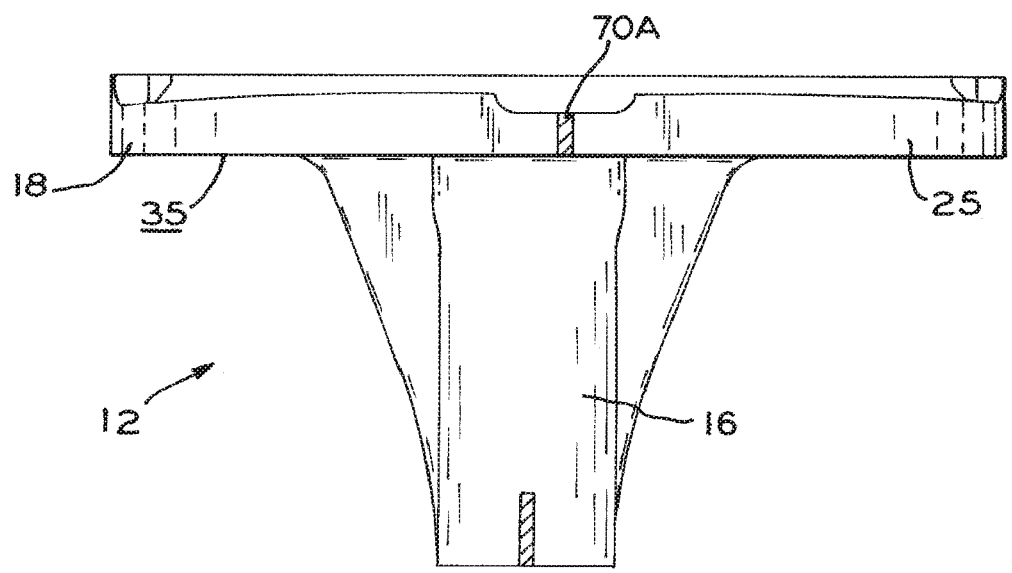
FIG. 4B is a side elevation view of the tibial baseplate shown in FIG. 4A.

The embodiments shown and described with regard to FIGS. 1A, 1B, 3A, 4A, 4B, 5 and 6 illustrate a left knee and associated features of a right-knee prosthesis, while the embodiments shown and described in FIGS. 2A, 2B and 3D illustrate the periphery of a right knee prosthesis. Right and left knee configurations are mirror images of one another about a sagittal plane. Thus, it will be appreciated that all aspects of the prosthesis described herein are equally applicable to a left- or right-knee configuration.

1. Asymmetry of the Tibial Prosthesis.

Referring now to FIGS. 1A and 1B, tibial prosthesis 10 includes tibial baseplate 12 and tibial bearing component 14. Tibial baseplate 12 may include a stem or keel 16 (FIG. 4B) extending distally from proximal tibial plateau 18, or may utilize other fixation structures for securing baseplate 12 to tibia T, such as distally extending pegs. Portions of the outer periphery defined by tibial plateau 18 closely correspond in size and shape with a resected proximal surface of tibia T, as described in detail below.

Tibial bearing component 14 and tibial baseplate 12 have a particular asymmetry, with respect to home axis $A_H$ (shown in FIG. 2A and described above), that is designed to maximize tibial coverage for a large proportion of knee-replacement candidates. This high level of coverage allows a surgeon to cover the largest possible area on the proximal resected surface of the tibia, which in turn offers maximum coverage of cortical bone. Advantageously, the maximized coverage of cortical bone facilitates superior support of tibial baseplate 12. A firm, enduring fixation of tibial baseplate 12 to tibia T is facilitated by large-area contact between the cortical and cancellous bone of tibia T and distal surface 35 of tibial plateau 18 (FIG. 4B), which may be coated with porous ingrowth material and/or bone cement.

In an analysis of a several human specimens, variations in size and geometry for a variety of anatomic tibial features were observed and characterized. Geometrical commonalties between anatomic features, or lack thereof, were noted. Mean tibial peripheral geometries were calculated based on statistical analysis and extrapolation of the collected anatomical data, in view of the observed geometrical commonalties organized around anatomic home axis $A_H$. These calculated mean geometries were categorized by tibial size.

A comparison between the asymmetric peripheries for the present family of prostheses and the calculated mean tibial geometries was conducted. Based on the results of this comparison, it has been found that substantial tibial coverage can be achieved for a large proportion of patients using tibial components having asymmetric peripheries in accordance with the present disclosure. Moreover, this coverage can be achieved with a relatively small number of sizes, even where particular portions of the prosthesis periphery is intentionally "pulled back" from the tibial periphery in order to confer other orthopaedic benefits. Further, the particular asymmetry of tibial baseplate 12 can be expected to offer such coverage without overhanging any portion of the resected surface.

Thus, periphery 200 including the particular asymmetric profile as described below confers the benefits of maximum coverage, facilitation of proper rotation (discussed below), and long-term fixation as described herein. Such asymmetry may be demonstrated in various ways, including: by a comparison of adjacent radii in the medial and lateral compartments of the asymmetric periphery; by a comparison of the edge length in anterior-medial and anterior lateral corners of the periphery, for a comparable lateral and medial angular sweep; and by a comparison of the location of radius centers for the anterior-medial and anterior-lateral corners with respect to a mediolateral axis. Various comparisons and quantifications are presented in detail below. Specific data and other geometric details of the peripheries for the various prosthesis sizes, from which the below-identified comparisons and quantifications are derived, may be obtained from the draw-to-scale peripheries shown in FIG. 2A.

Advantageously, the asymmetry of tibial component 12 encourages proper rotational orientation of baseplate 12 upon implantation thereof onto tibia T. As described in detail below, the asymmetry of periphery 200 (FIG. 2A) of tibial plateau 18 is designed to provide a close match in selected areas of the lateral and medial compartments as compared to the anatomic bone. As such, a surgeon can select the largest possible component from among a family of different component sizes, such that the component substantially covers the resected tibia T with minimal gaps between the tibial periphery and component periphery 200, as well as little or no overhang over any portions of the tibial periphery. Because the high congruence between prosthesis periphery 200 and the tibial periphery produces only a minimal gap between the peripheries (as shown in FIG. 5), tibial baseplate 12 cannot be rotated significantly without causing tibial plateau 18 to overhang beyond the periphery of the resected tibial surface. Thus, proper rotation of baseplate 12 can be ascertained by the visual acuity between prosthesis periphery 200 and the resected tibial surface.

The following examples and data are presented with respect to tibial baseplate 12. However, as described in more detail below, tibial bearing component 14 defines perimeter wall 54 which follows peripheral wall 25 of baseplate 12 except where noted. Thus, it is appreciated that the conclusions, trends and design features gleaned from data relating to the asymmetric periphery of tibial baseplate 12 also applies to the asymmetric periphery of tibial bearing component 14, except where stated otherwise.

Lateral compartment 20 and medial compartment 22 of tibial plateau 18 are dissimilar in size and shape, giving rise to the asymmetry thereof. This asymmetry is designed so that peripheral wall 25 traces the perimeter of the resected proximal surface of tibia T, such that tibial plateau 18 covers a large proportion of the resected proximal tibial surface as shown in FIG. 5. To achieve this large tibial coverage, tibial plateau 18 closely matches the periphery of tibia T in most areas as noted above. Nevertheless, as shown in FIG. 5, for example, a small gap between periphery 200 of tibial plateau 18 and tibia T is formed to allow some freedom of positioning and rotational orientation. The gap is designed to have a substantially continuous width in most areas, including the anterior edge, anterior-medial corner, medial edge, lateral edge and lateral-posterior corner (all described in detail below).

However, certain aspects of the asymmetric shape are designed to intentionally deviate from the calculated anatomical shape to confer particular features and advantages in the context of a complete, implanted knee prosthesis. Referring to FIG. 5, for example, tibial baseplate 12 and tibial bearing component 14 have anterior-lateral "corners" (described in detail below) which are "pulled back" to create gap 56 between tibia T and prosthesis 10 in the anterior-lateral area of the resected surface of tibia T. Advantageously, gap 56 creates extra space for "soft-tissue friendly" edges of prosthesis 10, thereby minimizing impingement of the iliotibial band. In an exemplary embodiment, gap 56 may range from 0.5 mm for a small-size prosthesis (such as size 1/A described below), to 1 mm for a medium-sized prosthesis (such as size 5/E described below), to 2 mm for a large-sized prosthesis (such as size 9/J described below).

Similarly, the posterior edge of the medial compartment may be "pulled back" from the adjacent edge of tibia T to define gap 58. Gap 58 allows extra space for adjacent soft tissues, particularly in deep flexion as described below. Gap 58 also allows prosthesis 10 to be rotated about a lateral pivot by a small amount, thereby offering a surgeon the freedom to displace medial compartment 22 posteriorly as required or desired for a particular patient. In an exemplary embodiment, gap 58 is about 4 mm.

Figure 8:
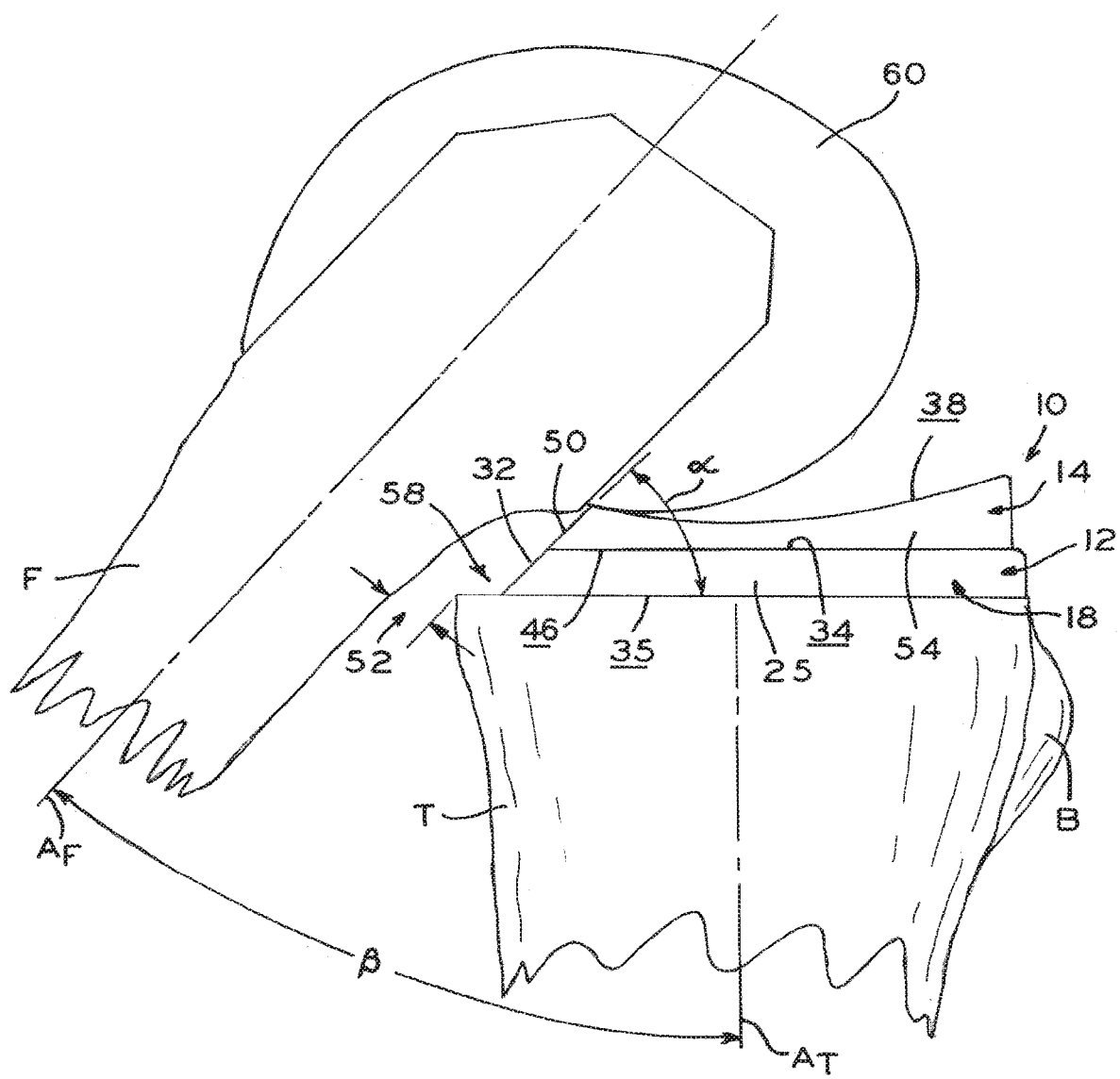
FIG. 8 is a side, elevation view of the tibial components shown in FIG. 1A, in conjunction with a femoral component.

As described in detail below, the asymmetrical periphery also provides a large overall area for proximal surface 34 of baseplate 12, which creates sufficient space for large contact areas between tibial bearing component 14 and femoral component 60 (FIG. 8).

a. Medial/Lateral Peripheral Curvatures

The particular asymmetric shape of tibial plateau 18 (and of tibial bearing component 14, which defines a similar periphery as described below) gives rise to a generally "boxy" or angular periphery in lateral compartment 20, and a "rounded" or soft periphery in medial compartment 22.

Turning to FIG. 3A, the periphery 200 of tibial plateau 18 surrounds lateral compartment 20 and medial compartment 22, each of which define a plurality of lateral and medial arcs extending between anterior edge 202 and lateral and medial posterior edges 204, 206 respectively. In the illustrative embodiment of FIG. 3A, anterior edge 202, lateral posterior edge 204 and medial posterior edge 206 are substantially planar and parallel for ease of reference. However, it is contemplated that edges 202, 204, 206 may take on other shapes and configurations within the scope of the present disclosure, such as angled or arcuate.

In the exemplary embodiment of FIG. 3A, lateral compartment 20 includes five separate arcs including lateral anterior edge arc 208, anterior-lateral corner arc 210, lateral edge arc 212, posterior-lateral corner arc 214, and lateral posterior edge arc 216. Each of lateral arcs 208, 210, 212, 214 and 216 defines angular sweep 1L, 2L, 3L, 4L and 5L, respectively, having radii R1L, R2L, R3L, R4L and R5L respectively. A radius of a particular angular sweep extends from the respective radius center (i.e., one of centers C1L, C2L, C3L, C4L and C5L) to periphery 200. Radii R1L, R2L, R3L, R4L and R5L each remain unchanged throughout the extent of angular sweeps 1L, 2L, 3L, 4L and 5L, respectively.

Similarly, medial compartment 22 includes three separate arcs including anterior-medial corner arc 220, medial edge arc 222 and posterior-lateral corner arc 224, defining angular sweeps 1R, 2R and 3R, respectively having radii R1R, R2R and R3R respectively.

In FIG. 2A, peripheries $200_X$ are shown for each of nine progressively larger component sizes, with $200_1$ being the periphery of the smallest size (size "1" or "A") and $200_9$ being the periphery of the largest size (size "9" or "J"). For purposes of the present disclosure, several quantities and features of tibial baseplate 12 may be described with the subscript "X" appearing after the reference numeral corresponding to a component size as set for in the Tables, Figures and description below. The subscript "X" indicates that the reference numeral applies to all nine differently-sized embodiments described and shown herein.

In exemplary embodiments, medial and lateral radii may be any value within the following ranges: for medial radius $R1R_X$, between about 27 mm and about 47 mm; for medial radius $R2R_X$, between about 21 mm and about 49 mm; for medial radius $R3R_X$, between about 14 mm and about 31 mm; for lateral radius $R1L_X$, between about 46 mm and about 59 mm; for lateral radius $R2L_X$, between about 13 mm and about 27 mm; for lateral radius $R3L_X$ between about 27 mm and about 46 mm; for lateral radius $R4L_X$ between about 6 mm and about 14 mm; and for lateral radius $R5L_X$ between about 22 mm and about 35 mm.

In exemplary embodiments, medial and lateral angular extents or sweeps may be any value within the following ranges: for medial angle $1R_X$, between about 13 degrees and about 71 degrees; for medial angle $2R_X$, between about 23 degrees and about 67 degrees; for medial angle $3R_X$, between about 23 degrees and about 90 degrees; for lateral angle $1L_X$, between about 11 degrees and about 32 degrees; for lateral angle $2L_X$, between about 42 degrees and about 63 degrees; for lateral angle $3L_X$, between about 23 degrees and about 47 degrees; for lateral angle $4L_X$, between about 36 degrees and about 46 degrees; and for lateral angle $5L_X$, between about 28 degrees and about 67 degrees;

The unique asymmetry of periphery 200 defined by tibial plateau 18 can be quantified in multiple ways with respect to the curvatures of lateral and medial compartments 20 and 22 as defined by the arrangement and geometry of lateral arcs 208, 210, 212, 214, 216 and medial arcs 220, 222, 224.

One measure of the asymmetry of periphery 200 is found in a simple comparison of radii R2L and R1R, which are the anterior "corner" radii of lateral and medial compartments 20 and 22 respectively. Generally speaking, a corner of a baseplate periphery may be said to be that portion of the periphery where a transition from an anterior or posterior edge to a lateral or medial edge occurs. For example, in the illustrative embodiment of FIG. 3A, the anterior-lateral corner is principally occupied by anterior-lateral corner arc 210, which defines a substantially medial-lateral tangent at the anterior end of arc 210 and a substantially anteroposterior tangent at the lateral end of arc 210. Similarly, the medial corner of periphery 200 is principally occupied by anterior-medial corner arc 220, which defines a substantially medial-lateral tangent at the anterior end of arc 220 and a more anteroposterior tangent at the lateral end of arc 220. For some purposes, the anterior-medial corner of periphery 200 may be said to include a portion of medial edge arc 222, as described below.

A periphery corner may also be defined by a particular angular sweep with respect to an anteroposterior reference axis. Such reference axis may extend posteriorly from an anterior-most point of a tibial prosthesis (e.g., from the center of anterior edge 202 of periphery 200) to divide the prosthesis into medial and lateral halves. In a symmetrical prosthesis, the anteroposterior reference axis is the axis of symmetry.

In the illustrative embodiment of FIG. 3A, the anteroposterior reference axis may be home axis $A_H$, such that the anterior-medial corner of periphery 200 occupies some or all of the 90-degree clockwise angular sweep between home axis $A_H$ (at zero degrees, i.e., the beginning of the clockwise sweep) and mediolateral axis $A_{ML}$ (at 90 degrees, i.e., the end of the sweep). Similarly, the anterior-lateral corner of periphery 200 occupies some or all of the 90-degree counter-clockwise angular sweep between home axis $A_H$ and mediolateral axis $A_{ML}$.

For example, the anterior-medial and anterior-lateral corners may each occupy the central 45 degree angular sweep of their respective 90-degree angular sweeps as described above. Thus, the anterior-lateral corner of periphery 200 would begin at a position rotated 22.5 degrees counter-clockwise from home axis $A_H$ as described above, and would end at 67.5 degrees counter-clockwise from home axis $A_H$. Similarly, the anterior-medial corner would begin at a 22.5-degree clockwise rotation and end at a 67.5 degree clockwise rotation.

It is contemplated that the anterior-lateral and anterior-medial corners may occupy any angular sweep as required or desired for a particular design. For purposes of comparison between two corners in a given prosthesis periphery, however, a comparable angular sweep for the lateral and medial sides is envisioned, i.e., the extent and location of the compared angles may be "mirror images" of one another about an anteroposterior axis. For example, in a comparison of anterior-lateral and anterior-medial radii R2L, R1R, it is contemplated that such comparison is calculated across lateral and medial angular sweeps which each begin and end at similar angular end points with respect to the chosen reference axis (e.g., home axis $A_H$).

As best seen in FIGS. 3A and 5, one aspect of the asymmetric periphery of baseplate 12 arises from $R1R_X$ being substantially larger than $R2L_X$. Table 1, below, also includes a comparison of radii $R1R_X$ and $R2L_X$ across nine exemplary component sizes, demonstrating that difference Δ-12L between radius $R1R_X$ and radius $R2L_X$ may be as little as 48%, 76% or 78%, and may be as much as 102%, 103% or 149%. It is contemplated that radius $R1R_X$ may be larger than radius $R2L_X$ by any percentage value within any range defined by the listed values.

TABLE 1

Comparisons of Values of Respective Medial and Lateral Anterior Corner Radii

| SIZE | Δ-12RL R1R vs. R2L |
|---|---|
| 1/A | 103.0% |
| 2/B | 149.2% |
| 3/C | 82.4% |
| 4/D | 74.6% |
| 5/E | 90.9% |
| 6/F | 78.6% |
| 7/G | 102.2% |
| 8/H | 86.5% |
| 9/J | 48.1% |
| AVG | 90.6% |

All Δ values are expressed as the difference between a given pair of radii, expressed as a percentage of the smaller of the two radii Stated another way, the smaller $R2L_X$ makes a sharper turn, thereby imparting a relatively more "boxy" appearance to the anterior corner of lateral compartment 20, while the relatively larger radius $R1R_X$ makes a more gradual turn that imparts a more "rounded" appearance to the anterior corner of medial compartment 22. In the exemplary nine sizes illustrated in FIG. 2A and shown in Table 1, an average disparity between the lateral and medial anterior corner radii $R2L_X$ and $R1R_X$ is greater than 90%. In some sizes of periphery $200_X$, the anterior-medial "corner" making the more gradual turn may also includes medial edge arc 222.

As described in detail below, this "rounded-medial/boxy-lateral" asymmetry of the anterior corners of tibial plateau facilitates and encourages proper rotational orientation and positioning of baseplate 12 upon tibia T upon implantation by allowing periphery 200 to closely match the periphery of a typical resected tibia T (FIG. 5), while also maximizing the surface area of proximal surface 34 of tibial plateau to allow for use of a tibial bearing component 14 with a concomitantly large proximal surface area.

As noted above, the small-radius "corner" defined by angle 2L may be considered to have a similar angular sweep as a large-radius "corner" defined by angles 1R, 2R (or a combination of portions thereof) for purposes of comparing the two radii. Given this comparable angular sweep, another measure of the asymmetry defined by the medial and lateral anterior corners is the arc length of the corners. More particularly, because medial radii $R1R_X$ and $R2R_X$ are larger than lateral radius $R2L_X$ (as described above), it follows that the medial corner has a larger arc length as compared to the lateral corner arc length for a given angular sweep.

Moreover, while the peripheries of lateral and medial compartments 20, 22 are shown as being generally rounded and therefore defining respective radii, it is contemplated that an asymmetric periphery in accordance with the present disclosure need not define a radius per se, but rather could include one or more straight line segments which, on the whole, define asymmetric corner edge lengths in the medial and lateral compartments. Referring to FIG. 3B, for example, it is contemplated that an alternative anterior lateral corner 210' could be comprised of three line segments 210A, 210B, 210C which cooperate to span angular extent 2L. Similarly, an alternative anterior medial corner 220' could be comprised of three line segments 220A, 220B, 220C which cooperate to span angular extent 1R. Any of the other arcs which define periphery 200 could be similarly configured as one or more line segments. In the variant illustrated by FIGS. 3B and 3C, the difference between corner radii would not be an appropriate measure of asymmetry because the straight line segments would not define radii. Asymmetry of the medial and lateral anterior corners would instead be quantified by comparison of the respective lengths of the medial and lateral corner edges across comparable medial and lateral angular extents.

Yet another way to quantify the asymmetry of the anterior corner arcs (i.e., anterior-lateral corner arc 210 and anterior-medial corner arc 220) is to compare the distance of the lateral and medial radius centers C2L and C1R respectively, from anterior edge 202 and/or mediolateral axis $A_M$. (FIG. 3A). In the boxy anterior-lateral corner, center $C2L_X$ of radius $R2L_X$ is anterior of mediolateral axis $A_{ML}$ and relatively close to anterior edge 202. For the rounded, anterior-medial corner, centers $C1R_X$ and $C2R_X$ of radii $R1R_X$ and $R2R_X$, respectively, are posterior of mediolateral axis $A_{ML}$, and relatively far from anterior edge 202.

Another metric for quantifying the "boxy vs. rounded" asymmetry of periphery 200 is a comparison between ratios of adjacent radii. In the more boxy lateral compartment 20, pairs of adjacent radii define large ratios because the large edge radii (i.e., of lateral anterior edge arc 208, lateral edge arc 212 and lateral posterior edge arc 216) are much larger than the adjacent corner radii (i.e., of anterior-lateral corner arc 210 and posterior-lateral corner arc 214). On the other hand, in the more rounded medial compartment 22, pairs of adjacent radii define small ratios (i.e., nearly 1:1) because the radii of the medial arcs (i.e., anterior-medial corner arc 220, medial edge arc 222 and posterior-medial corner arc 224) are of similar magnitude.

In the illustrated embodiment of FIG. 3A, lateral edge arc 212 is considered an "edge" because arc 212 defines tangent 212A which is substantially perpendicular to anterior edge 202. Just as a "corner" may be considered to be the portion of periphery 200 which makes a transition from anterior or posterior to medial or lateral, an edge is that portion of periphery 200 which encompasses the anterior, posterior, medial or lateral terminus of periphery 200.

Similarly, medial edge arc 222 defines tangent 222A which is also substantially perpendicular to anterior edge 202. The medial "edge" of periphery 200 may be part of the same arc that extends around the anterior-medial corner and/or the anterior-lateral corner, as the medial arcs are similar. Indeed, as noted herein, medial compartment 22 may have a single arc which extends from anterior edge 202 to medial posterior edge 206.

Table 2 shows a comparison between adjacent-radii ratios for lateral and medial compartments 20 and 22. For each adjacent pair of radii, the difference between the radii magnitudes are expressed as a percentage of the smaller radius of the pair, as noted above.

TABLE 2

Comparisons of Values of Respective Pairs of Baseplate Peripheral Radii

| SIZE | Δ-12R R1R vs. R2R | Δ-23R R2R vs. R3R | Δ-12L R1L vs. R2L | Δ-23L R2L vs. R3L | Δ-34L R3L vs. R4L | Δ-45L R4L vs. R5L |
|---|---|---|---|---|---|---|
| 1/A | 18.3% | 58.6% | 337.3% | 141.8% | 323.5% | 194.1% |
| 2/B | 49.0% | 62.0% | 254.1% | 96.7% | 361.5% | 315.4% |
| 3/C | 24.0% | 48.8% | 247.1% | 58.8% | 203.4% | 214.6% |
| 4/D | 44.2% | 34.4% | 207.0% | 59.2% | 213.9% | 244.4% |
| 5/E | 23.3% | 57.9% | 151.5% | 80.6% | 250.0% | 250.0% |
| 6/F | 46.5% | 37.6% | 122.6% | 42.9% | 222.6% | 260.2% |
| 7/G | 25.3% | 38.9% | 110.8% | 64.5% | 264.3% | 176.2% |
| 8/H | 73.6% | 21.3% | 109.0% | 80.9% | 198.1% | 142.6% |
| 9/J | 21.9% | 61.2% | 70.4% | 68.5% | 264.0% | 172.0% |
| AVG | 36.2% | 46.7% | 178.9% | 77.1% | 255.7% | 218.8% |

All Δ values are expressed as the difference between a given pair of radii, expressed as a percentage of the smaller of the two radii As illustrated in Table 2, the "boxy" periphery of lateral compartment 20 gives rise to disparity values Δ-12L, Δ-23L, Δ-34L and Δ-45L that are at least 42%, 48% or 59%, and as great as 323%, 337% or 362%. It is contemplated that the disparity between a pair of adjacent radii in the boxy periphery of lateral compartment 20 may be any percentage value within any range defined by any of the listed values. It is also contemplated that the lateral disparity values may be substantially higher, as required or desired for a particular application.

Meanwhile, the "rounded" periphery of medial compartment 22 gives rise to disparity values Δ-12R and Δ-23R that are as small as 21%, 23% or 25%, and no greater than 61%, 62% or 74%. It is contemplated that the disparity between a pair of adjacent radii in the rounded periphery of medial compartment 22 may be any value within any range defined by any of the listed values. It is also contemplated that the medial disparity values may be less than 21%, and as little as zero %, as required or desired for a particular application.

Moreover, the boxy shape of lateral compartment 20 and rounded shape of medial compartment 22 is also demonstrated by the number of arcs used to define the portion of periphery 200 in lateral and medial compartments 20, 22. In lateral compartment 20, five arcs (i.e., arcs 208, 210, 212, 204, 216) are used to define the lateral periphery, which is indicative of anterior, lateral and posterior "sides" of a box joined by the relatively sharp transitions of corner arcs 210, 214. On the other hand, medial compartment 22 uses only three radii (i.e., 220, 222, 224), leaving no clear definition of any box "sides" or other transitions. Indeed, it is contemplated that medial compartment 22 could join anterior edge 202 to medial posterior edge 206 by a single radius within the scope of the present disclosure.

b. Surface Area of Medial and Lateral Baseplate Compartments

Referring still to FIG. 3A, yet another characterization of the asymmetry of periphery 200 arises from disparities in surface area for lateral and medial compartments 20, 22. For purposes of the present disclosure, surface area of lateral compartment SAL is that area contained within periphery 200, and on the lateral side of home axis $A_H$. Similarly, the surface area of medial compartment 22 is that area contained within periphery 200, and on the medial side of home axis $A_H$.

In an exemplary embodiment, lateral surface area $SAL_X$ may be as little as 844 mm² or may be as much as 1892 mm², or may be any area within the range defined by the foregoing values. In an exemplary embodiment, medial surface area $SAM_X$ may be as little as 899 mm² or may be as much as 2140 mm², or may be any area within the range defined by the foregoing values.

Surfaces areas SAL and SAM do not include any of the area occupied by PCL cutout 28, as any such area is not within periphery 200. However, the asymmetry of surface areas SAL and SAM arises primarily from the differences in the geometry and placement of arcs 208, 210, 212, 214, 216, 220, 222, 224 rather than from any asymmetry of PCL cutout 28. In the illustrative embodiments of FIG. 2A, for example, PCL cutout $28_X$ is symmetrical with respect to home axis $A_H$, but extends further posteriorly in medial compartment 22.

Thus, it is contemplated that the asymmetry of surfaces areas SAL, SAM are little changed by exclusion of the PCL cutout 28 from the area calculation. As illustrated in FIG. 3D, PCL cutout 28 is effectively excluded from calculation by extrapolating the line formed by lateral posterior edge 204 and medial posterior edge 206 inwardly to intersect with home axis $A_H$. In lateral compartment 20, such extrapolation cooperates with the lateral side of PCL cutout 28 to define lateral fill area 80. In medial compartment 22, such extrapolation cooperates with the medial side of PCL cutout 28 to define medial fill area 82.

In the illustrative embodiment of FIG. 3D, lateral surface area $SAL_X'$ may be as little as 892 mm² or may be as much as 2066 mm², or may be any area within the range defined by the foregoing values. In an exemplary embodiment, medial surface area $SAM_X'$ may be as little as 986 mm² or may be as much as 2404 mm², or may be any area within the range defined by the foregoing values.

Tables 3 and 4 below illustrate that medial surface area $SAM_X$ occupies a greater percentage of the total surface area contained within periphery $200_X$, regardless of whether PCL cutout 28 is included in the calculation. That is to say, medial fill area 82 is larger than lateral fill area 80 by approximately the same proportion as medial and lateral surfaces areas $SAM_X$, $SAL_X$. In the exemplary embodiments of FIG. 3A, medial surface area $SAM_X$ occupies between 52% and 53% of the total surface area regardless, while lateral surface area $SAM_X$ occupies the remainder. If the PCL cutout is excluded from the calculation as shown in FIG. 3D, medial surface area $SAM_X'$ occupies between 52% and 54% of the total surface area, while lateral surface area $SAM_X'$ occupies the remainder. With or without the PCL cutout included in the calculation, it is contemplated that medial surface areas $SAM_X$, $SAM_X'$ may occupy as little as 51% of the total surface area, and as much as 60% of the total surface area.

TABLE 3

Medial vs. Lateral Tibial Baseplate Surface Areas for Baseplates with a PCL Cutout (FIGS. 2A and 3A) With PCL Notch

| Size | Medial Surface Area $SAM_X$ as % of Total Surface Area |
| --- | --- |
| 1/A | 52% |
| 2/B | 52% |
| 3/C | 52% |
| 4/D | 52% |
| 5/E | 52% |
| 6/F | 52% |
| 7/G | 53% |
| 8/H | 53% |
| 9/J | 53% |

TABLE 4

Medial vs. Lateral Tibial Baseplate Surface Areas for Baseplates without a PCL Cutout (FIG. 3D) Without PCL Notch

| Size | Medial Surface Area $SAM_X'$ as % of Total Surface Area |
| --- | --- |
| 1/A | 53% |
| 2/B | 52% |
| 3/C | 53% |
| 4/D | 53% |
| 5/E | 53% |
| 6/F | 53% |
| 7/G | 53% |
| 8/H | 54% |
| 9/J | 54% | c. Anteroposterior Extent of Medial and Lateral Compartments

Still another way to characterize and quantify the asymmetry of tibial periphery 200 is to compare the overall anteroposterior extent of lateral and medial compartments 20, 22.

Turning to FIG. 2A (which is drawn to scale, according to scales 230 and 232) and FIG. 2B, lateral compartment 20 of tibial plateau 18 defines overall lateral anteroposterior extent $DAPL_X$, while medial compartment 22 of tibial plateau 18 defines overall medial anteroposterior extent $DAPM_X$, where X is an integer between 1 and 9 corresponding to a particular component size as shown in FIG. 2A, as noted above. As illustrated in Table 5 below, lateral anteroposterior extent $DAPL_X$ is less than medial anteroposterior extent $DAPM_X$ for all component sizes.

This disparity in anteroposterior extent can be said to result from medial compartment 22 extending posteriorly further than lateral compartment 20. In the illustrative embodiment of FIG. 2B, lateral anteroposterior extent $DAPL_X$ extends from anterior edge 202 to lateral posterior edge 204, while medial anteroposterior extent $DAPM_X$ extends from anterior edge 202 to medial posterior edge 206. Thus, if one takes anterior edge 202 to be the anteroposterior "zero point," the additional anteroposterior extent defined by medial compartment 22 is due entirely to the further posterior position of medial posterior edge 206.

As set forth in the right-hand column of Table 5, exemplary embodiments of tibial baseplate 12 may define medial anteroposterior extent $DAPM_X$ that is larger than lateral anteroposterior extent $DAPL_X$ by as little as 12.1%, 12.2% or 12.4%, and as much as 13.7%, 14.2% or 14.5%. It is contemplated that such disparity between medial and lateral anteroposterior extents $DAPM_X$, $DAPL_X$ may be any percentage within any range defined by the listed values of Table 5. Advantageously, the particular asymmetric arrangement of tibial baseplate 12 with respect to anteroposterior extent of lateral and medial compartments 20, 22 facilitates substantially complete coverage of tibia T, without overhanging the edge of tibia T, in a wide variety of patients.

TABLE 5

Overall A/P and M/L Dimensions for Tibial Baseplates (FIGS. 2A and 2B)

| Size (X) | Growth in A/P Medial Dimension (DAPM), from next-smaller size, mm | Growth in A/P Lateral Dimension (DAPL), from next-smaller size, mm | Additional A/P Extent of DAPM vs. DAPL, % of DAPL |
|---|---|---|---|
| 1/A | — | — | 14.5% |
| 2/B | 2.3 | 2.13 | 14.2% |
| 3/C | 2.4 | 2.25 | 13.7% |
| 4/D | 2.3 | 2.27 | 13.1% |
| 5/E | 3 | 2.8 | 12.7% |
| 6/F | 3.1 | 2.85 | 12.4% |
| 7/G | 3.2 | 2.81 | 12.5% |
| 8/H | 3.3 | 3.11 | 12.2% |
| 9/J | 3.73 | 3.34 | 12.1% |

For example, in an exemplary family of prosthesis sizes, at least 60% and as much as 90% coverage of the resected proximal surface is provided by tibial plateau 18 of tibial baseplate 12 when rotation is limited to +/−5 degrees from home axis $A_H$. In a majority of all patients, such coverage is between 75-85%. Coverage of up to 100% may be achieved within the scope of the present disclosure, such as by fully extending the posterior-medial and anterior-lateral coverage of tibial plateau (which intentionally leave gaps between tibial plateau 18 and the periphery of tibia T as noted herein).

The additional posteromedial material of tibial plateau 18 includes chamfer 32, described in detail below with respect to the assembly of tibial baseplate 12 to tibial bearing component 14. Chamfer 32 is formed in peripheral wall 25, such that chamfer 32 forms angle α (FIG. 8) with the distal or bone-contacting surface 35 of tibial plateau 18. In the illustrated embodiment, chamfer 32 defines a substantially linear sagittal cross-sectional profile, with angle α between about 35 degrees and about 55 degrees. In addition, it is contemplated that chamfer 32 may have an arcuate profile in a sagittal, coronal and/or transverse plane, and may include convex or concave curvature as required or desired for a particular application.

2. Progressive Peripheral Growth Between Implant Sizes

In addition to the asymmetry of each individual size/embodiment of tibial baseplate 12, described in detail above, the present disclosure also provides asymmetry in the way periphery 200 grows from one size to the next. Advantageously, this asymmetric peripheral growth accommodates observed growth trends in tibias T of differently-sized patients, while also preserving the optimal fit and coverage provided by baseplate 12, and offering the other advantages of designs in accordance with the present disclosure as described herein.

In symmetrical peripheral growth, a larger size of baseplate is a scaled-up version of a smaller size and vice-versa. In the present asymmetrical peripheral growth, by contrast, certain parameters of tibial baseplate 12 grow faster than others as the overall size of the baseplate gets larger (i.e., from smallest size 1/A through largest size 9/J). Thus, differently-sized components made in accordance with the present disclosure are not proportional to one another in all respects, in that a larger tibial prosthesis is not proportionally larger than a smaller tibial prosthesis in all aspects.

Referring now to FIG. 2B, periphery $200_X$ defines centroid $C_X$, which is medially biased with respect to home axis $A_H$ owing to medial surface area SAM being larger than lateral surface area SAL (as described in detail above). Posterior-medial distance $DMP_X$ extends from centroid $C_X$ toward the posterior-medial "corner" of periphery $200_X$ (i.e., toward posterior-medial corner arc 224, shown in FIG. 3A and described above) at an angle of 130 counter-clockwise degrees from home axis $A_H$. Similarly, posterior-lateral distance $DLP_X$ extends from centroid $C_X$ toward the posterior-lateral "corner" of periphery $200_X$ (i.e., toward posterior-lateral corner arc 214, shown in FIG. 3A and described above) at an angle of 120 clockwise degrees from home axis $A_H$. The posterior-lateral and posterior-medial corners are defined in a similar fashion as the anterior-lateral and anterior-medial corners, described in detail above. Moreover, while the asymmetric posterior-medial and posterior lateral growth among consecutive sizes is described below with respect to distances $DLP_X$, $DMP_X$, such growth occurs in the entire area occupied by the posterior-medial and posterior-lateral corners.

Figure 2C:
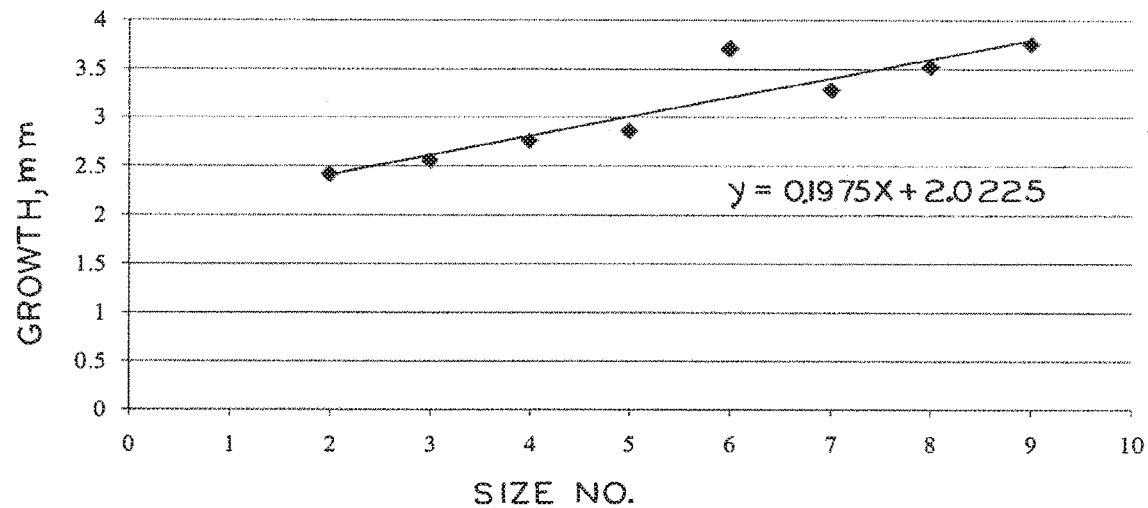
FIG. 2C is a graph illustrating the asymmetric growth of the posterior-medial compartment for the tibial baseplates shown in FIG. 2A.
Figure 2D:
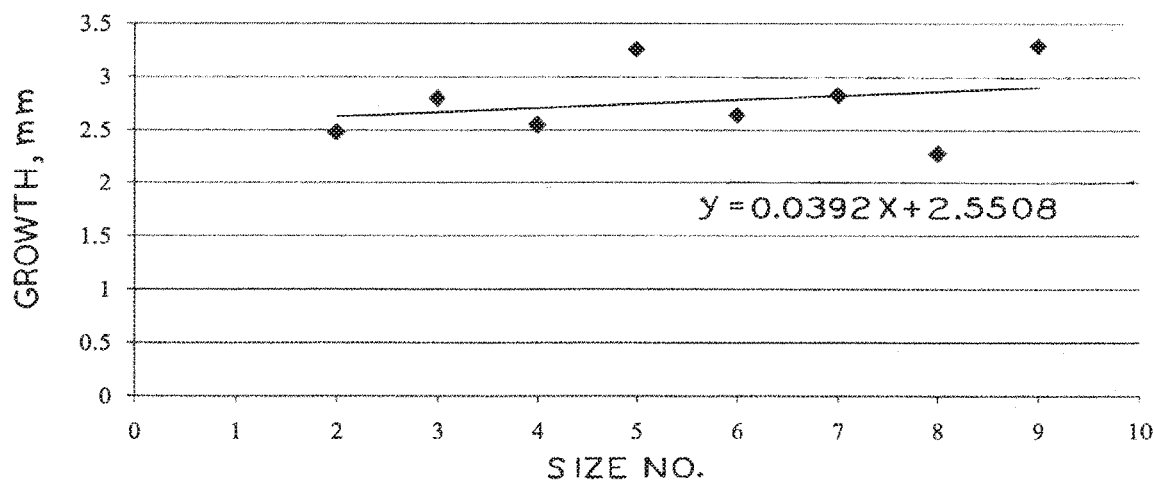
FIG. 2D is a graph illustrating the asymmetric growth of the posterior-lateral compartment for the tibial baseplates shown in FIG. 2A.

As illustrated in FIG. 2A and shown in Table 6 below, lateral- and medial-posterior distances $DLP_X$, $DMP_X$ do not grow linearly as smallest size 1/A progresses among consecutive sizes to eventually reach largest size 9/J. Rather, lateral- and medial-posterior distances $DLP_X$, $DMP_X$ exhibit an increase in the magnitude of growth as the sizes progress consecutively from size 1/A to size 9/J. This non-linear, asymmetric growth is illustrated in the graphs of FIGS. 2C and 2D and in Table 6 below.

TABLE 6

Growth of the Posterior-Medial and Posterior-Lateral Corners of Baseplate Periphery (FIGS. 2A and 2B)

| Size (X) | Growth in medial-posterior distance $DMP_x$ from centroid ($C_x$), compared to next-smaller size, mm | Growth in lateral-posterior distance ($DLP_x$) from centroid ($C_x$), compared to next-smaller size, mm |
|---|---|---|
| 1 | — | — |
| 2 | 2.42 | 2.48 |
| 3 | 2.56 | 2.8 |
| 4 | 2.76 | 2.55 |
| 5 | 2.86 | 3.26 |
| 6 | 3.71 | 2.64 |
| 7 | 3.28 | 2.83 |
| 8 | 3.52 | 2.28 |
| 9 | 3.76 | 3.29 |

In FIG. 2C, the amount of growth in $DMP_X$ is plotted against size no. X. As illustrated, the family of tibial baseplates 12 illustrated in FIG. 2A exhibit a steadily increasing growth in $DMP_X$, with nearly 20% average increase in growth from one size to the next consecutive size (as represented by the slope of the linear trend line having equation y=0.1975x+2.0225).

In FIG. 2D, the amount of growth in $DLP_X$ is plotted against size no. X, and illustrates a smaller, but still positive growth increase across baseplate sizes. More specifically, the family of tibial baseplates 12 illustrated in FIG. 2A exhibit a nearly 4% average increase in growth from one size to the next consecutive size (as represented by the slope of the linear trend line having equation y=0.0392x+2.5508).

As used herein, a "family" of prostheses refers to a set or kit of prostheses sharing common geometrical and/or performance characteristics. For example, the family of nine tibial baseplates whose peripheries $200_X$ are shown in FIG. 2A share a common asymmetry as described herein, such that each tibial baseplate is adapted to provide substantial tibial coverage, facilitate proper implant rotation and avoid impingement with various soft tissues of the knee. Typically, a family of prostheses includes a plurality of differently-sized components, with consecutively larger/smaller components sized to accommodate a variety of differently-sized bones. In the exemplary embodiments of the present disclosure, a size "1" or "A" prosthesis is the smallest prosthesis of the family, a size "9" or "J" prosthesis is the largest prosthesis of the family, and each of the intermediate sizes "2" or "B" through "8" or "H" are consecutively larger sizes.

Advantageously, in the family or kit of prosthesis peripheries shown in FIG. 2A, each tibial baseplate 12 (FIG. 1A) having periphery $200_X$ provides a close match to a particular subset of patient tibias T having a unique size and shape. Particular features of periphery $200_X$ have been designed with non-linear growth which is calculated to provide the closest possible fit for the largest number of particular natural geometries found in anatomic tibias T, as described in detail herein. This close fit allows for maximum coverage of the resected proximal tibial periphery $200_X$, by accommodating the non-linear changes which may occur across anatomic tibial periphery sizes. Lateral- and medial-posterior distances $DLP_X$, $DMP_X$ are exemplary non-linear growth parameters found in a family of tibial baseplates 12, and are reflective of non-linear growth in mediolateral extent $DML_X$ and anteroposterior extents $DAPM_X$ and $DAPL_X$ across the various sizes.

3. PCL Cutout Aligned with Home Axis and Associated Technique

In the illustrated embodiment, tibial plateau 18 includes PCL cutout 28 disposed between compartments 20, 22, as described above. PCL cutout leaves PCL attachment point $C_P$ accessible, thereby allowing the PCL to pass therethrough during and after implantation of tibial baseplate 12. Tibial bearing component 14 (FIG. 5) may similarly include cutout 30.

Thus, the illustrated embodiment of tibial prosthesis 10 is adapted for a cruciate retaining (CR) surgical procedure, in which the posterior cruciate ligament is not resected during implantation of tibial prosthesis 10. Further, as noted above, home axis $A_H$ includes reference to PCL attachment point $C_P$ when tibial baseplate 12 is mounted upon tibia T. In order to facilitate alignment of home axis $A_H$ with respect to tibial baseplate 12 and tibia T, alignment indicia 70A, 70P (FIGS. 4A and 4B) may be marked on proximal surface 34 and/or peripheral wall 25. When tibial baseplate 12 is implanted (as described below), anterior alignment indicia 70A (FIGS. 4A and 4B) is aligned with anterior point $C_A$ at the "medial third" of the anterior tibial tubercle T, and posterior alignment indicia 70P is aligned with the natural PCL attachment point $C_P$ of tibia T.

However, it is contemplated that a prosthesis in accordance with the present disclosure may be made for a design in which the posterior cruciate ligament is resected during surgery, such as "posterior stabilized" (PS) or "ultra congruent" (UC) designs. The PS and UC designs may exclude PCL cutout 30 in bearing component 14, thereby obviating the need for PCL cutout 28 in tibial baseplate 12. Continuous material may instead occupy cutout 28 (as schematically shown in FIG. 3D). Moreover, it is contemplated that PCL cutouts 28, 30 may have any shape and/or size within the scope of the present disclosure. For example, PCL cutouts 28, 30 may be asymmetrical with respect to an anteroposterior axis. For purposes of the present disclosure "bisecting" an asymmetric PCL cutout with an anteroposterior axis refers to dividing such cutout into two equal areas for a given anteroposterior section of the anteroposterior axis 4. Tibial Bearing Component and Deep Flexion Enablement Turning again to FIG. 1A, tibial bearing component 14 includes lateral portion 39, medial portion 41, inferior surface 36 adapted to couple to tibial baseplate 12, and superior surface 38 adapted to articulate with condyles of a femoral component (such as femoral component 60 shown in FIG. 8 and described in detail below). Superior surface 38 includes lateral articular surface 40 in lateral portion 39 and medial articular surface 42 in medial portion 41, with eminence 44 (FIG. 5) disposed between articular surfaces 40, 42. Referring to FIG. 5, eminence 44 generally corresponds in shape and size with a natural tibial eminence of tibia T prior to resection.

Referring now to FIG. 1A, tibial plateau 18 of tibial baseplate 12 further includes a distal or bone contacting surface 35 and an opposing proximal or superior surface 34, with superior surface 34 having raised perimeter 24 and locking mechanism 26 formed between lateral and medial compartments 20, 22. Raised perimeter 24 and locking mechanism 26 cooperate to retain tibial bearing component 14 upon tibial baseplate 12, as described in detail below. Exemplary baseplate locking mechanisms are described in U.S. provisional patent application Ser. Nos. 61/367,374 and 61/367,375, both entitled TIBIAL PROSTHESIS and both incorporated by reference as stated above.

Inferior surface 36 of tibial bearing component 14 includes recess 46 at the periphery thereof and a tibial bearing locking mechanism (not shown) disposed between lateral and medial articular surfaces 40, 42. Exemplary bearing component locking mechanisms are disclosed in U.S. provisional patent application Ser. Nos. 61/367,374 and 61/367,375, both entitled TIBIAL PROSTHESIS. Recess 46 is sized and positioned to correspond with raised perimeter 24 of tibial plateau 18, and the tibial bearing locking mechanism cooperates with locking mechanism 26 of tibial plateau 18 to fix tibial bearing component 14 to tibial baseplate 12 in a desired position and orientation as described in detail below. However, it is contemplated that tibial bearing component 14 may be affixed to baseplate 12 by any suitable mechanism or method within the scope of the present disclosure, such as by adhesive, dovetail tongue/groove arrangements, snap-action mechanisms, and the like.

As best seen in FIGS. 1B, 5 and 8, the outer periphery of tibial bearing component 14 generally corresponds with the outer periphery of tibial plateau 18, except for the posteromedial extent of plateau 18 as compared with tibial bearing component 14. The anterolateral "corner" of tibial bearing component 14 defines radius $R_3$ (FIG. 5) having a generally common center with radius R2L of baseplate 12 in a transverse plane, i.e., radii R2L and $R_3$ are substantially coincident in a plan view. Similarly, the anteromedial "corner" of tibial bearing component 14 defines radius $R_4$ having a generally common center with radius R1R of baseplate 12 in a transverse plane, i.e., radii R1R and $R_4$ are substantially coincident in a plan view.

$R_3$ defines a slightly smaller radial length as compared to R2L, and $R_4$ defines a slightly smaller radial length as compared to R1R, such that the anterior portion of perimeter wall 54 of tibial bearing component 14 is set back from the anterior portion of peripheral wall 25 (i.e., from anterior edge 202 and adjacent arcs, as described above) of tibial baseplate 12. As with the above-described comparison between radii R2L and R1R, anteromedial radius $R_4$ is substantially larger than anterolateral radius $R_3$.

Given that medial portion 41 of tibial bearing component 14 has a lesser anteroposterior extent compared to medial compartment 22 of tibial plateau 18, medial portion 41 must be biased anteriorly in order for the anterior-medial "corners" of tibial bearing component 14 and tibial plateau 18 to coincide as shown in FIG. 5. In view of this anterior bias, it may be said that tibial bearing component 14 is asymmetrically oriented upon tibial plateau 18. More particularly, although lateral articular surface 40 is generally centered with respect to lateral compartment 20 of tibial plateau 18, medial articular surface 42 is anteriorly biased with respect to medial compartment 22 of tibial plateau 18 in order to leave chamfer 32 exposed at the posterior-lateral corner. This asymmetric mounting of tibial bearing component 14 upon tibial plateau 18 ensures a desired articular interaction between tibial prosthesis 10 and femoral component 60, as described in detail below.

Tibial plateau 18 of tibial baseplate 12 deviates from the periphery of tibial bearing component 14 in the posteromedial portion of each component, leaving medial portion 41 incongruent with medial compartment 22 of tibial baseplate 12. More particularly, tibial plateau 18 extends posteromedially to substantially cover the proximal resected surface of tibia T, as shown in FIG. 5 and described in above, while tibial bearing component 14 does not extend posteromedially beyond the superior terminus of chamfer 32 (i.e., tibial bearing component 14 does not "overhang" chamfer 32). In addition, tibial bearing component 14 includes chamfer 50 formed in peripheral wall 54, with chamfer 50 having a profile and geometrical arrangement corresponding with chamfer 32 of tibial plateau 18. More particularly, when tibial bearing component 14 is assembled to tibial baseplate 12 as shown in FIGS. 1B and 8, the anterior orientation or "bias" of the medial portion of tibial bearing component 14 (as described above) aligns chamfers 32, 50, which in turn cooperate to create a substantially continuous chamfer extending from tibia T to medial articular surface 42. Referring to FIG. 8, chamfers 32, 50 further cooperate to define void 52 formed between femur F and tibial plateau 18 when tibial prosthesis 10 is in a deep flexion orientation. In the illustrated embodiment of FIG. 8, the deep flexion orientation is defined by angle β between anatomic tibia axis $A_T$ and anatomic femoral axis $A_F$ of up to about 25 degrees to about 40 degrees, for example (i.e., about 140 degrees to 155 degrees of flexion or more).

Advantageously, void 52 cooperates with the "pulled back" or incongruent posterior medial edge 206 and posterior medial corner 224, as compared to a typical tibial periphery (described above), to allow the deep flexion orientation to be achieved without impingement of femoral component 60 and/or femur F upon tibial plateau 18 and/or tibial bearing component 14. Soft tissues in the region of void 52 are therefore also accommodated with little or no impingement on the surrounding components.

In addition, the relatively large size of tibial plateau 18 (covering a large proportion of the resected proximal surface of tibia T) also allows tibial bearing component 14 to be relatively large, so that tibial bearing component 14 provides sufficient non-articular surface area at chamfers 32, 50 and around the periphery of lateral and medial articular surfaces 40, 42 to allow relatively large-radius, rounded transitions between articular surfaces 40, 42 and peripheral wall 54 of tibial bearing component 14. These gradual, large-radius transitions prevent undue friction between tibial prosthesis 10 and any surrounding soft tissues which may remain in place after implantation of the prosthesis, such as the iliotibial (IT) band.

In certain ranges of prosthesis articulation, for example, the human iliotibial (IT) band may touch the anterolateral "corner", i.e., the portion of tibial bearing component 14 having radius $R_3$. Because the anterolateral extent of tibial bearing component 14 follows the anterolateral extent of tibial plateau 18 (as described above), the transition between lateral articular surface 40 and peripheral wall 54 at the point of contact between an IT band and tibial bearing component 14 can have a relatively large convex portion while still leaving sufficient concave space for articular surface 40. This large convex portion results in a large contact area if the IT band does contact tibial bearing component 14, which in turn results in relatively low pressures on the IT band. Further, the anterolateral "pull back" or incongruence between the anterior-lateral corner are 210 of periphery 200 and a typical tibial periphery, described in detail above, allows the corresponding anterior-lateral corner of bearing component 14 to maintain separation from the IT band through a wide range of flexion, and low contact pressures where contact does occur.

However, to any such contact between the IT band and tibial bearing component 14 may be avoided or minimized by designing periphery 200 such that anterior-lateral corner arc 210 and/or lateral edge arc 212 is brought away from the expected periphery of a typical tibia T (as calculated from anatomical data, described above). This extra spacing designed into periphery 200 provides extra clearance for the iliotibial band. In addition, this extra clearance assures that the substantial proportion of prospective patients lacking Gerdy's tubercle, which is an eminence located at the anterior-lateral portion of tibia T, will not experience any "overhang" of tibial plateau 18 beyond the anatomic periphery of resected tibia T.

Thus, generally speaking, tibial prosthesis 10 can be considered "soft tissue friendly" because the edges of tibial bearing component 14 and tibial plateau 18, including chamfers 32, 50, are smooth and rounded, so that any soft tissue coming into contact with these edges will be less likely to chafe or abrade.

Advantageously, the relatively large inferior/distal surface area of tibial plateau 18 facilitates a large amount of bone ingrowth where bone ingrowth material is provided in tibial baseplate 12. For example, baseplate 12 may also be constructed of, or may be coated with, a highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of implant [#] to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

5. Trial Tibial Components

Tibial prosthesis 10 may be provided in a variety of sizes and configurations to accommodate different bone sizes and geometries. The choice of one particular size may be planned preoperatively such as through preoperative imaging and other planning procedures. Alternatively, an implant size may be chosen, or a previous size choice modified, intraoperatively. To facilitate proper intraoperative selection of a particular size for tibial prosthesis 10 from among the family of sizes shown in FIG. 2A, and to promote proper orientation of the chosen prosthesis 10, tibial prosthesis 10 may be part of a kit including one or more template or "sizing" components.

Figure 6:
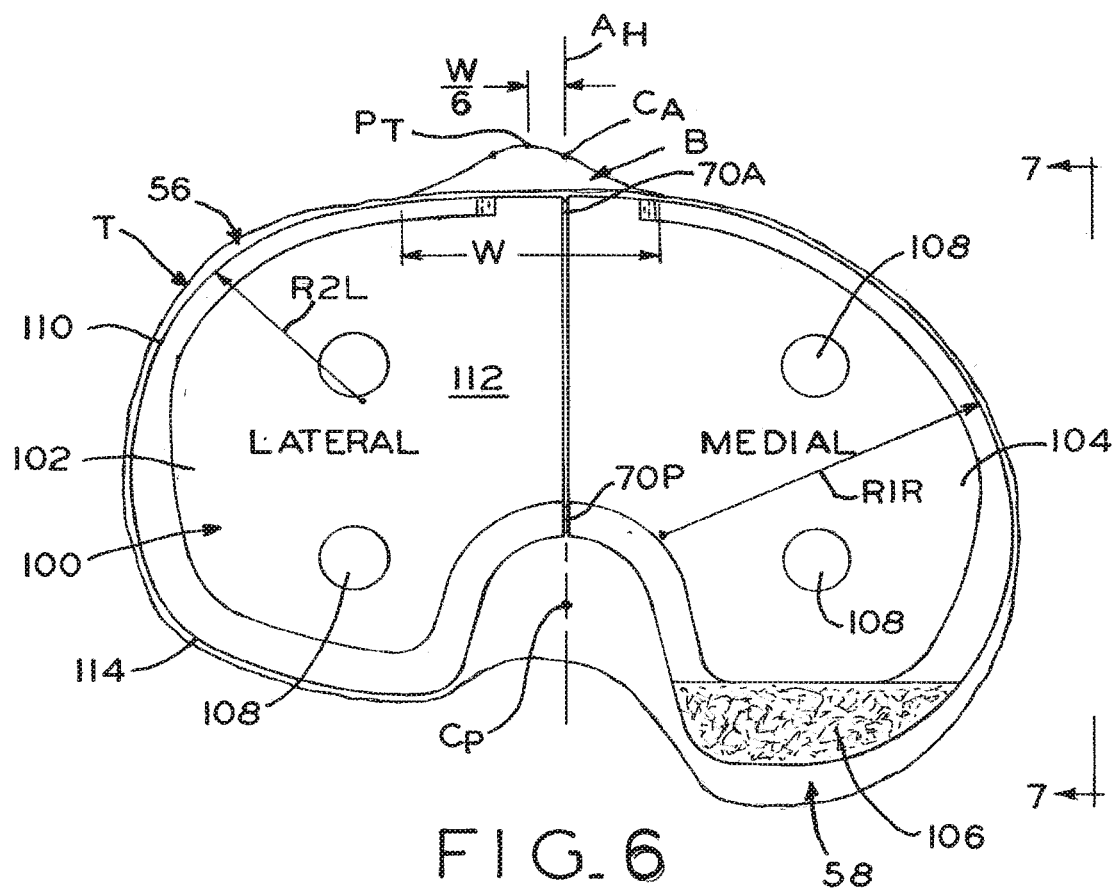
FIG. 6 is a top plan view of a resected proximal tibial surface with a properly sized tibial trial component thereon.
Figure 7:
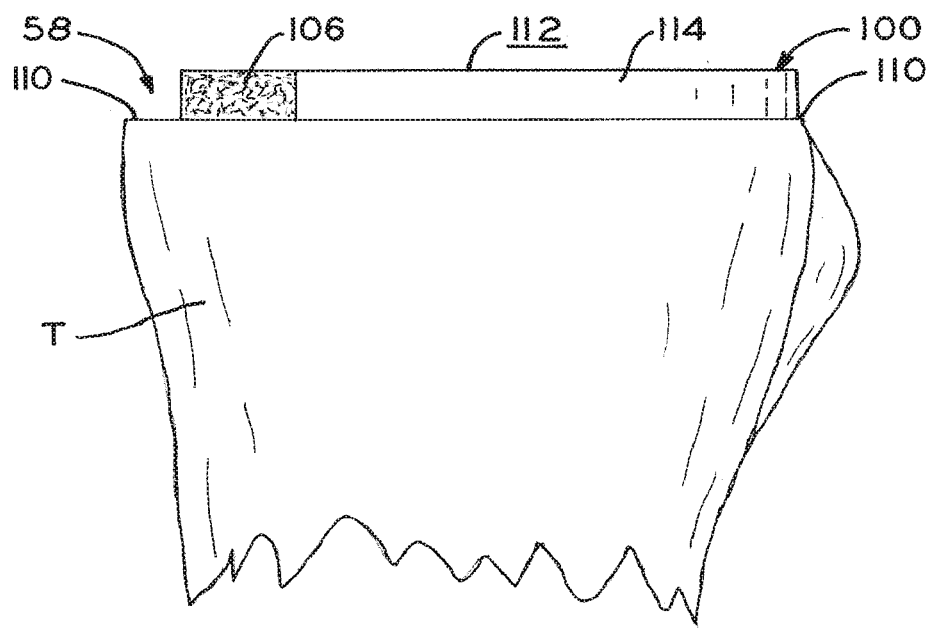
FIG. 7 is a side, elevation view of the tibia and trial component shown in FIG. 6.

Referring now to FIGS. 6 and 7, trial prosthesis 100 may be temporarily coupled to tibia T for intraoperative sizing evaluation of tibial prosthesis 10 and initial steps in the implantation of tibial prosthesis 10. Trial prosthesis 100 is one of a set of trial prostheses provided as a kit, with each trial prosthesis having a different size and geometrical configuration. Each trial prosthesis in the set of trial prostheses corresponds to a permanent prosthesis 10, such as sizes 1/A-9/J of tibial baseplate 12 as described above.

For example, as shown in FIG. 6, trial prosthesis 100 defines superior surface 112 generally corresponding in size and shape to proximal surface 34 of tibial plateau 18, and including lateral portion 102 and medial portion 104. Superior surface 112 is asymmetrical about home axis $A_H$, with lateral portion 102 having a generally shorter overall anteroposterior extent as compared to medial portion 104 (which includes void indicator 106, discussed below). In addition, the anterolateral "corner" of lateral portion 102 defines radius R2L, which is identical to radius R2L of tibial plateau 18, while the anteromedial "corner" of medial portion 104 defines radius R1R, which is identical to radius R1R of tibial plateau 18 and greater than radius R2L.

Moreover, perimeter wall 114 of trial prosthesis 100 is substantially identical to peripheral wall 25 of tibial plateau 18, and therefore defines periphery 200 with the same features and shapes of perimeter 200 described above with respect to tibial plateau 18. Thus, trial prosthesis 100 is asymmetrical about home axis $A_H$ in a similar manner to tibial plateau 18 of tibial baseplate 12, with the nature of this asymmetry changing across the various other sizes of tibial prosthesis provided in the kit including trial prosthesis 100.

In an alternative embodiment, a trial prosthesis may be provided which extends completely to the posterior-medial edge of the natural tibial resection periphery. Thus, such a trial would substantially completely cover the resected tibial surface, thereby aiding in determination of a proper rotational orientation of the trial (and, therefore, of the final tibial baseplate 12). In this alternative embodiment, the trial prosthesis lacks the posterior-medial "pull back" of tibial plateau 18, described above.

Trial prosthesis 100 includes void indicator 106 disposed at the posterior portion of medial portion 104, consuming a given posteromedial area of superior surface 34 and peripheral wall 25. Void indicator 106 indicates where void 52 (discussed above) will be located with respect to tibia T after implantation of tibial prosthesis 10. Void indicator 106 facilitates proper rotational and spatial orientation of trial prosthesis 100 on the resected proximal surface of tibia T by allowing a surgeon to visually match tibial bearing component 14 with trial prosthesis 100, as described in detail below. In the illustrated embodiment, void indicator 106 is an area of visual and/or tactile contrast with the remainder of tibial plateau 18. This contrast may include, for example, a contrasting color, texture, surface finish, or the like, or may be formed by a geometric discrepancy such as a step or lip, for example.

Referring specifically to FIG. 6, trial prosthesis 100 further includes a plurality of peg hole locators 108 corresponding to the proper location for peg holes in tibia T to receive pegs (not shown) extending inferiorly from tibial plateau 18 of tibial baseplate 12. Advantageously, peg hole locators 108 allow a surgeon to demarcate the proper center for peg holes in tibia T once the proper size and orientation for trial prosthesis 100 has been found, as discussed in detail below. Alternatively, peg hole locators 108 may be used as drill guides to drill appropriately positioned peg holes while trial prosthesis is still positioned on tibia T.

6. Tibial Prosthesis Implantation

In use, a surgeon first performs a resection of tibia T using conventional procedures and tools, as are well-known in the art. In an exemplary embodiment, a surgeon will resect the proximal tibia to leave a planar surface prepared for receipt of a tibial baseplate. This planar surface may define a tibial slope, which is chosen by the surgeon. For example, the surgeon may wish to perform a resection resulting in positive tibial slope in which the resected tibial surface slopes proximally from posterior to anterior (i.e., the resected surface runs "uphill" from posterior to anterior). Alternatively, the surgeon may instead opt for negative tibial slope in which the resected tibial surface slopes distally from posterior to anterior (i.e., the resected surface runs "downhill" from posterior to anterior). Varus or valgus slopes may also be employed, in which the resected surface slopes proximally or distally from medial to lateral. The choice of a tibial and/or varus/valgus slope, and the amount or angle of such slopes, may depend upon a variety of factors including correction of deformities, mimicry of the native/preoperative tibial slope, and the like.

In an exemplary embodiment, keel 16 (FIG. 4B) defines a 5-degree, anteriorly-extending angle with respect to bone-contacting surface 35 of tibial plateau 18. Tibial baseplate 12 is appropriate for use with a positive tibial slope of as little as zero degrees and as much as 9 degrees, and with a varus or valgus slope of up to 3 degrees. However, it is contemplated that a tibial baseplate made in accordance with the present disclosure may be used with any combination of tibial and/or varus/valgus slopes, such as by changing the angular configuration of the keel with respect to the bone-contacting surface.

With a properly resected proximal tibial surface, the surgeon selects trial prosthesis 100 from a kit of trial prostheses, with each prosthesis in the kit having a different size and geometrical configuration (as discussed above). Trial prosthesis 100 is overlaid on the resected surface of tibia T. If trial prosthesis 100 is appropriately sized, a small buffer zone 110 of exposed bone of resected tibia T will be visible around the periphery of trial prosthesis 100. Buffer 110 is large enough to allow a surgeon to rotate and/or reposition trial prosthesis 100 within a small range, thereby offering the surgeon some flexibility in the final positioning and kinematic profile of tibial prosthesis 10. However, buffer 110 is small enough to prevent trial prosthesis 100 from being rotated or moved to an improper location or orientation, or from being implanted in such as way as to produce excessive overhang of the edge of trial prosthesis 100 past the periphery of the resected tibial surface. In one exemplary embodiment, for example, trial prosthesis may be rotated from a centered orientation by up to +/−5 degrees (i.e., in either direction), though it is contemplated that such rotation may be as much as +/−10 degrees or +/−15 degrees.

To aid in rotational orientation, trial prosthesis may include anterior and posterior alignment indicia 70A, 70P, which are the same marks in the same location as indicia 70A, 70P provided on tibial plateau 18 as described above. The surgeon can align indicia 70A with anterior point $C_A$ and indicia 70P with PCL attachment point $C_P$, in similar fashion as described above, to ensure the anatomical and component home axes $A_H$ are properly aligned. Alternatively, a surgeon may use indicia 70A, 70P to indicate a desired deviance from alignment with home axis $A_H$. As noted above, deviation of up to 5 degrees is envisioned with the exemplary embodiments described herein. A surgeon may choose to orient indicia 70A, 70P to another tibial landmark, such as the middle of the patella or the medial end of tibial tubercle B.

Thus, the large coverage of trial prosthesis 100 (and, concomitantly, of tibial plateau 18) ensures that tibial baseplate 12 will be properly positioned and oriented on tibia T upon implantation, thereby ensuring proper kinematic interaction between tibial prosthesis 10 and femoral component 60. If buffer zone 110 is either nonexistent or too large, another trial prosthesis 100 is selected from the kit and compared in a similar fashion. This process is repeated iteratively until the surgeon has a proper fit, such as the fit illustrated in FIGS. 6 and 7 between trial prosthesis 100 and tibia T.

With the proper size for trial prosthesis 100 selected and its orientation on tibia T settled, trial prosthesis 100 is secured to tibia T, such as by pins, screws, temporary adhesive, or any other conventional attachment methods. Once trial prosthesis is so secured, other trial components, such as trial femoral components and trial tibial bearing components (not shown) may be positioned and used to articulate the leg through a range of motion to ensure a desired kinematic profile. During such articulation, void indicator 106 indicates to the surgeon that any impingement of femoral component 60 and/or femur F upon trial prosthesis 100 at void indicator 106 will not occur when tibial prosthesis 10 is implanted. Once the surgeon is satisfied with the location, orientation and kinematic profile of trial prosthesis 100, peg hole locators 108 may be used to demarcate the appropriate location of peg holes in tibia T for tibial baseplate 12. Such peg holes may be drilled in tibia T with trial prosthesis 100 attached, or trial prosthesis 100 may be removed prior to drilling the holes.

With tibia T prepared for receipt of tibial prosthesis 10, tibial baseplate 12 may be provided by the surgeon (such as from a kit or surgical inventory), and is implanted on tibia T, with pegs fitting into holes previously identified and demarcated using peg hole locators 108 of trial prosthesis 100. Tibial baseplate 12 is selected from the family of tibial baseplates illustrated in FIG. 2A to correspond with the trial component 100 chosen, which ensures that tibial plateau 18 will cover a large proportion of the resected proximal surface of tibia T, as trial prosthesis 100 did prior to removal. Tibial baseplate is affixed to tibia T by any suitable method, such as by keel 16 (FIG. 4B), adhesive, bone-ingrowth material, and the like.

With tibial baseplate 12 installed, tibial bearing component 14 may be coupled with tibial baseplate 12 to complete tibial prosthesis 10. However, once attached, tibial bearing component 14 does not fully cover tibial plateau 18 of tibial baseplate 12. Rather, tibial bearing component 14 leaves a posteromedial portion of tibial baseplate 12 uncovered to create void 52 (as shown in FIG. 8 and discussed above). Thus, a surgeon may wish to verify that this anterior-biased, "asymmetrical" orientation of medial articular surface 42 is proper prior to permanent affixation of tibial bearing component 14 to tibial baseplate 12.

To accomplish such verification, tibial bearing component 14 is placed side-by-side with trial prosthesis 100, with inferior surface 36 of tibial bearing component 14 in contact with superior surface 112 of trial prosthesis 100. Tibial bearing component 14 will substantially cover superior surface 112, but will not cover void indicator 106. Put another way, peripheral wall 54 of tibial bearing component 14 will trace perimeter wall 114 of tibial trial prosthesis 100, excluding the posteromedial area defined by void indicator 106. If inferior surface 36 of tibial bearing component 14 is a match with superior surface 112 of trial prosthesis 100 except for void indicator 106 (which is left uncovered by tibial bearing component 14), then tibial bearing component 14 is the proper size component and may be confidently installed upon tibial plateau 18 of tibial baseplate 12.

Tibial baseplate 12 may then be implanted upon the proximal surface of tibia T in accordance with accepted surgical procedures. Exemplary surgical procedures and associated surgical instruments are disclosed in "Zimmer LPS-Flex Fixed Bearing Knee, Surgical Technique," "NEXGEN COMPLETE KNEE SOLUTION, Surgical Technique for the CR-Flex Fixed Bearing Knee" and "Zimmer NexGen Complete Knee Solution Extramedullary/Intramedullary Tibial Resector, Surgical Technique" (collectively, the "Zimmer Surgical Techniques"), copies of which are submitted on even date herewith, the entire disclosures of which are hereby expressly incorporated by reference herein.

When the surgeon is satisfied that tibial bearing component 14 is properly matched and fitted to the installed tibial baseplate 12, bearing component 14 is secured using locking mechanism 26 and the corresponding tibial bearing locking mechanism an appropriate instrumentation (not shown). Proper location and rotational orientation of tibial bearing component 14 upon tibial plateau 18 is ensured by raised perimeter 24 cooperating with recess 46, and locking mechanism 26 cooperating with the corresponding tibial bearing locking mechanism (not shown). Such proper orientation results in medial articular surface 42 being generally anteriorly disposed with respect to medial compartment 22 of tibial plateau 18.

Femoral component 60 may be affixed to a distal end of femur F, if appropriate, using any conventional methods and/or components. Exemplary surgical procedures and instruments for such affixation are disclosed in the Zimmer Surgical Techniques, incorporated by reference above. Femur F and tibia T may then be articulated with respect to one another to ensure that neither femur F nor femoral component 60 impinges upon tibial baseplate 12 and/or tibial bearing component 14 in deep flexion, such as at a flexion angle β of 155° as shown in FIG. 8. When the surgeon is satisfied with the location, orientation and kinematic profile of tibial prosthesis 10, the knee replacement surgery is completed in accordance with conventional procedures.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial baseplate comprising:
    a distal surface comprising a bone contacting surface;
    a proximal surface comprising a tibial bearing engagement surface generally opposite the distal surface; and
    a peripheral wall extending between the distal and the proximal surface, the peripheral wall defining:
    an anterior edge;
    a lateral periphery including:
        a lateral edge defining a substantially perpendicular tangent with respect to the anterior edge,
        an anterior-lateral corner traversing an angular sweep between the anterior edge and the lateral edge to define an anterior-lateral corner edge length, and
        a posterior-lateral corner extending away from the lateral edge and the anterior-lateral corner; and
    a medial periphery, wherein the medial periphery is asymmetric with respect to the lateral periphery about an anteroposterior axis, the medial periphery including:
        a medial edge defining a substantially perpendicular tangent with respect to the anterior edge,
        an anterior-medial corner traversing an angular sweep between the anterior edge and the medial edge to define an anterior-medial corner edge length that is longer than the anterior-lateral corner edge length, in which the angular sweep between the anterior edge and the medial edge is similar to the angular sweep between the anterior edge and the lateral edge, and
        a posterior-medial corner extending away from the medial edge and the anterior-medial corner.

2. The tibial baseplate of claim 1, wherein:
    the lateral edge comprises a lateral edge arc defining a lateral edge radius, the anterior-lateral corner comprises an anterior-lateral corner arc defining an anterior-lateral corner radius, and
    the lateral edge radius is larger than the anterior-lateral corner radius by at least 42%.

3. The tibial baseplate of claim 2, wherein the lateral edge radius is larger than the anterior-lateral corner radius by up to 142%.

4. The tibial baseplate of claim 1, wherein:
    the lateral edge comprises a lateral edge arc defining a lateral edge radius, the posterior-lateral corner comprises a posterior-lateral corner arc defining a posterior-lateral corner radius, and
    the lateral edge radius is larger than the posterior-lateral corner radius by at least 198%.

5. The tibial baseplate of claim 4, wherein the lateral edge radius is larger than the posterior-lateral corner radius by up to 324%.

6. The tibial baseplate of claim 1, wherein:
    the medial edge comprises a medial edge arc defining a medial edge radius,
    the anterior-medial corner comprises an anterior-medial corner arc defining an anterior-medial corner radius, and
    the medial edge radius is larger than the anterior-medial corner radius by up to 74%.

7. The tibial baseplate of claim 1, wherein:
    the medial edge comprises a medial edge arc defining a medial edge radius,
    the posterior-medial corner comprises a posterior-medial corner arc defining a posterior-medial corner radius, and
    the medial edge radius is larger than the posterior-medial corner radius by up to 61%.

8. The tibial baseplate of claim 1, wherein:
    the anterior-medial corner defines an anterior-medial corner arc defining an anterior-medial corner radius, the anterior-lateral corner defines an anterior-lateral corner arc defining an anterior-lateral corner radius,
    the anterior-medial corner radius is different from the anterior-lateral corner radius.

9. The tibial baseplate of claim 1, wherein the lateral periphery defines an arcuate anterior section between the anterior edge and the anterior-lateral corner.

10. The tibial baseplate of claim 1, wherein:
    the lateral periphery defines a plurality of adjacent lateral arcs,
    the medial periphery defines a plurality of adjacent medial arcs, the plurality of adjacent lateral arcs are greater in number as compared to the plurality of adjacent medial arcs.

11. The tibial baseplate of claim 10, wherein the plurality of adjacent lateral arcs comprises at least five adjacent lateral arcs.

12. The tibial baseplate of claim 10, wherein the plurality of adjacent medial arcs comprises up to three adjacent lateral arcs.

13. The tibial baseplate of claim 1, wherein:
    the anterior-lateral corner comprises an anterior-lateral corner arc defining an anterior-lateral corner radius, and
    the anterior-medial corner comprises an anterior-medial corner arc defining an anterior-medial corner radius,
    the anterior-medial corner radius is larger than the anterior-lateral corner radius.

14. The tibial baseplate of claim 1, wherein the tibial baseplate is sized and shaped to cover between about 60% and about 90% of a resected proximal surface of a tibia to create a buffer zone on all sides between a perimeter of a surface of the tibia and the peripheral wall.

15. The tibial baseplate of claim 1, wherein:
    the anterior-lateral corner comprises an anterior-lateral corner arc defining an anterior-lateral corner radius having a first radius center, and
    the anterior-medial corner comprises an anterior-medial corner arc defining an anterior-medial corner radius having a second radius center,
    the tibial baseplate in combination with a tibial bearing component is mountable to the tibial baseplate, the tibial bearing component comprising:
    a lateral portion defining an anterior-lateral bearing corner defining a third radius having a third radius center, the third radius center is substantially coincident with the first radius center in a transverse plane when the tibial bearing component is mounted to the tibial baseplate, the third radius is smaller than the anterior-lateral corner radius; and a medial portion defining an anterior-medial bearing corner defining a fourth radius having a fourth radius center, the fourth radius center is substantially coincident with the second radius center in the transverse plane when the tibial bearing component is mounted to the tibial baseplate, the fourth radius is smaller than the anterior-medial corner radius, the fourth radius substantially larger than the third radius.

16. The tibial baseplate of claim 1, wherein the anteroposterior axis is aligned with a home axis when the tibial baseplate is mounted to a tibia, the home axis defined as a line extending from a posterior point at a geometric center of an attachment area between a posterior cruciate ligament and the tibia, to an anterior point disposed on an anterior tubercle of the tibia, the tubercle having a tubercle width, the anterior point disposed on the tubercle at a location medially spaced from a midpoint of the tubercle by an amount equal to W/6.

17. The tibial baseplate of claim 1, wherein:
the tibial baseplate includes a PCL cutout area generally opposite the anterior edge and between the lateral periphery and the medial periphery, and
the anteroposterior axis bisects the anterior edge and bisects the PCL cutout area.

18. The tibial baseplate of claim 1, wherein:
the medial periphery cooperates with the anteroposterior axis to bound a medial surface area,
the lateral periphery cooperates with the anteroposterior axis to bound a lateral surface area, and
the medial surface area is larger than the lateral surface area.

\* \* \* \* \*